United States Patent [19]

Okano et al.

[11] Patent Number: 5,037,827
[45] Date of Patent: Aug. 6, 1991

[54] GLYCERIN DERIVATIVE AND ITS PHARMACOLOGICAL USE

[75] Inventors: Kazuo Okano; Osamu Asano; Naoyuki Shimomura; Tetsuya Kawahara; Shinya Abe; Shuhei Miyazawa, all of Ibaraki, Japan; Mitsuaki Miyamoto, Waltham, Mass.; Hiroyuki Yoshimura, Ibaraki, Japan; Koukichi Harada, Ibaraki, Japan; Junsaku Nagaoka, Ibaraki, Japan; Tsutomu Kawata, Waltham, Mass.; Tsutomu Yoshimura, Ibaraki, Japan; Hiromasa Suzuki, Ibaraki, Japan; Shigeru Souda, Ibaraki, Japan; Yoshimasa Machida, Ibaraki, Japan; Kouichi Katayama, Ibaraki, Japan; Isao Yamatsu, Ibaraki, Japan

[73] Assignee: Eisai Co., Ltd., Tokyo, Japan

[21] Appl. No.: 373,350

[22] Filed: Jun. 29, 1989

[30] Foreign Application Priority Data

Jul. 4, 1988 [JP] Japan .................. 63-166386

[51] Int. Cl.$^5$ .................. A61K 31/495; A61K 31/44; C07D 413/00; C07D 401/00
[52] U.S. Cl. .................................. 514/252; 514/218; 514/237.2; 514/318; 514/336; 514/340; 514/341; 514/343; 514/921; 540/575; 544/124; 544/360; 546/193; 546/194; 546/268; 546/275; 546/281; 546/283; 546/284; 546/309; 546/335; 546/336; 546/337
[58] Field of Search ............... 540/575; 544/124, 360; 546/193, 194, 281, 309, 336, 337; 514/218, 237.2, 252, 318, 341

[56] References Cited

U.S. PATENT DOCUMENTS 4,737,518 4/1988 Nomura et al. .................. 514/476

FOREIGN PATENT DOCUMENTS 0147768 12/1984 European Pat. Off. .
0157609 3/1985 European Pat. Off. .
0208932 6/1986 European Pat. Off. .
0158172 8/1985 Japan .
0243047 12/1985 Japan .
1293954 12/1986 Japan .

OTHER PUBLICATIONS

Barner et al., Chem. Abst. 104-88939n (1986).
Nomura et al., Chem. Abst. 104-88143y (1986).

Primary Examiner—Cecilia Shen
Attorney, Agent, or Firm—Birch, Stewart, Kolasch & Birch

[57] ABSTRACT

A glycerin derivative having the following formula (I) or (I') and a pharmacologically acceptable salt thereof are useful to treat diseases caused by the platelet activating factor.

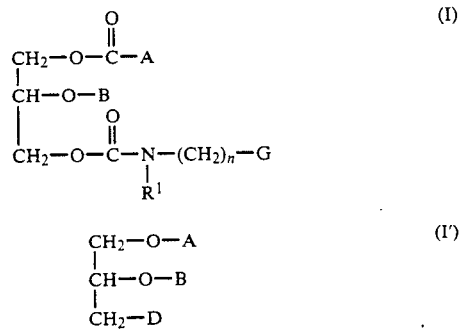

30 Claims, No Drawings

GLYCERIN DERIVATIVE AND ITS PHARMACOLOGICAL USE

This invention relates to a novel glycerin derivative and its pharmacological use.

PRIOR ARTS

The platelet activating factor (hereinafter referred to as PAF) has recently attracted attention and the correlation between it and various diseases is now being elucidated. In particular, it is supposed that PAF exerts an influence on an inflammation, DIC, endotoxin shock, asthma, gastrointestinal ulcer, nephritis, hepatitis and rejections in the transplantation of organs.

Under these circumstances, investigations are in progress for the purpose of finding compounds having a PAF-inhibiting effect. Glycerol derivatives described in, for example, Japanese Patent Laid-Open Nos. 158172/1985, 293954/1986 and 243047/1985 are among them. However, no satisfactory PAF inhibitors have been developed as yet.

Under these circumstances, the inventors have long made intensive investigations for the purpose of finding glycerol derivatives which are excellent in not only a PAF-inhibiting effect but also the persistence of this effect and the stability of the compounds themselves.

SUMMARY OF THE INVENTION

The invention provides a glycerin derivative having the following formula (I) or (I') and a pharmacologically acceptable salt thereof:

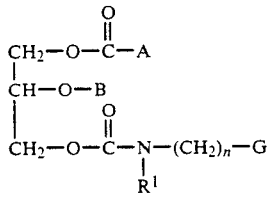  (I)

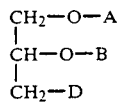  (I')

where in the formula (I): A represents:

(1) a group of the formula:

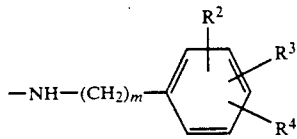

in which m represents an integer of 0 to 6, and $R^2$, $R^3$ and $R^4$ may be the same or different from one another and each represent a hydrogen atom or a lower alkoxy group, (2) a group of the formula:

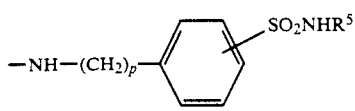

in which p represents an integer of 0 to 6 and $R^5$ represents a hydrogen atom, an alkyl group, a cycloalkyl group, a cycloalkylalkyl group, an aryl group or an arylalkyl group, (3) a group of the formula:

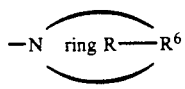

in which the ring R may comprise a nitrogen atom or oxygen atom in addition to carbon atoms, $R^6$ represents a hydrogen atom or a hydroxyl group, an alkyl group, an alkoxy group, an aryl group, a group of the formula: —$COR^7$ ($R^7$ being an alkyl group, an alkoxy group or a cycloalkyl group) or a group of the formula:

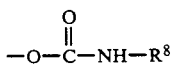

($R^8$ being a hydrogen atom or an alkyl group), (4) a group of the formula: —NH—$(CH_2)_q$—$R^9$ in which q represents an integer of 0 to 6 and $R^9$ represents an aryl group or a heteroaryl group, (5) a group of the formula: —NH—$(CH_2)_r$—$OR^{10}$ in which r represents an integer of 0 to 6 and $R^{10}$ represents an alkyl group, (6) a group of the formula:

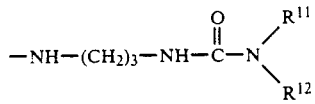

in which s represents an integer of 0 to 20, and $R^{11}$ and $R^{12}$ may be the same or different from each other and each represent a hydrogen atom or a lower alkyl group, (7) a group of the formula:

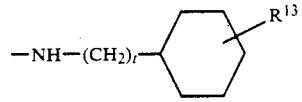

in which t represents an integer of 0 to 6 and $R^{13}$ represents a hydrogen atom or a lower alkoxycarbonyl group, (8) a group of the formula:

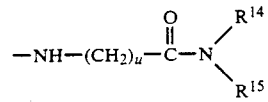

in which u represents an integer of 0 to 6 and $R^{14}$ and $R^{15}$ may be the same or different from each other and each represent a hydrogen atom or a lower alkyl group of $R^{14}$ and $R^{15}$ may be combined to form a ring which may comprise an oxygen atom, (9) a group of the formula: —NH—$(CH_2)_v$—O—$(CH_2)_w$—O—$(CH_2)_x$—H in which v represents an integer of 1 to 10, w represents an integer of 1 to 10 and x represents an integer of 1 to 10,

(10) a group of the formula:

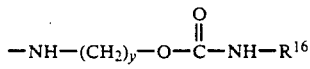

in which y represents an integer of 0 to 6 and $R^{16}$ represents a hydrogen atom or an alkyl group, or

(11) a group of the formula:

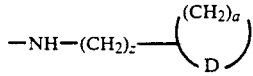

in which z represents an integer of 0 to 6, a represents an integer of 3 or 4 and D represents an oxygen atom, a sulfur atom or a nitrogen atom, B represents a lower alkyl group or an arylalkyl group, $R^1$ represents an acyl group, n represents an integer of 0 to 3, and G represents a group of the formula:

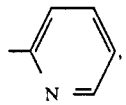

where in the formula (I'): A refers to the group indicated by formula (1),

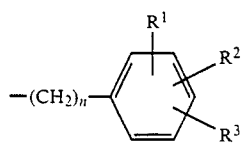

Formula (1)

(in the above formula, n refers to 0 or an integer from 1-6, and $R^1$, $R^2$ and $R^3$ refer to identical or different hydrogen atoms or alkoxy groups), the group indicated by formula (2),

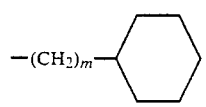

Formula (2)

(in the above formula, m refers to 0 or an integer from 1-6), or the group indicated in formula (3),

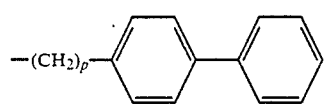

Formula (3).

B refers to an alkyl group or aryl alkyl group.

D refers to the group indicated with the formula $-Y-(CH_2)_q-G$ [in the above formula, Y refers to the group indicated by the formula

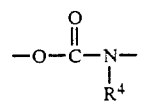

(in the above formula, $R^4$ refers to an aryl group or the group indicated by the formula

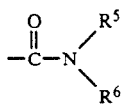

(in the above formula, $R^5$ and $R^6$ refer to identical or different hydrogen atoms or low order alkyl groups)), the group indicated by the formula

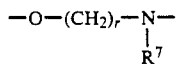

(in the above formula, r refers to an integer from 1-3 and $R^7$ refers to an acyl group), the group indicated by the formula

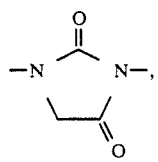

or the group indicated by the formula

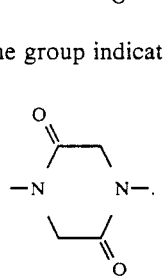

q refers to 0 or an integer from 1-3.

G refers to the group indicated by the formula

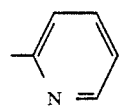

or the group indicated by the formula

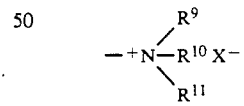

(in the formula, $R^9$, $R^{10}$ and $R^{11}$ refer to identical or different low order alkyl groups, and X refers to a pharmacologically allowable anion)].

In the invention the glycerin derivative having the formula (I) and a pharmacologically acceptable salt thereof are preferable. In particular the salt is more preferable. The pyridinium salt is most preferable.

It is preferred that the glycerin derivative has the formula (I), A is (3), B is a lower alkyl, R1 is an acyl group, n is 1 and G is 2-pyridyl.

The glycerin derivative and a pharmacologically acceptable salt thereof is preferred when the formula is (I), G is a pyridinium salt in which the nitrogen of the pyridyl for G in the formula (I) is quaternarized.

The glycerin derivative and a pharmacologically acceptable salt thereof having the the formula is (I) and for G a pyridinium salt having the formula:

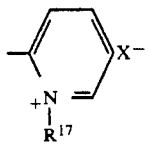

in which R17 is a lower alkyl and X is a pharmacologically acceptable anion such as a halogen. Chlorine and bromine are more preferable to the effect.

In the glycerin derivative of the formula (I) and a pharmacologically acceptable salt thereof, it is preferred that the glycerin derivative has the formula (I), A is (3), R6 is —OCO—NHR8, R8 is hydrogen or an alkyl, B is a lower alkyl, R1 is an acyl group and n is 1. In the formula (I), A is (3), the ring R of (3) is pyperidiene, R6 is —OCO—NHR8, R8 is hydrogen or an alkyl, B is methyl, R1 is an acyl group and n is 1. R1 may be a lower alkanoyl or an aroyl, substituted or not. The alkyl for R8 may have 14 to 22, more preferably 16 to 20, in particular 18. It is preferred that R1 is acetyl, benzoyl or a benzoyl having a substituent(s), in particular o-, m- or p-alkoxybenzoyl such as o-, m- or p-methoxybenzoyl. Most preferably is R1 o-methoxybenzoyl.

When the glycerin derivative has the formula (I) and A is 2), it is preferred that p is 1 and R5 is an alkyl having 14 to 22 carbon atoms. Also it is preferably that p is 1, R5 is an alkyl having 14 to 22 carbon atoms, B is methyl, R1 is o-, m- or p-methoxybenzoyl and n is 1.

When the glycerin derivative has the formula (I) and A is (10), it is preferably that B is methyl, R1 is o-, m- or p-methoxybenzoyl and n is 1.

The most preferably compound of the formula (I) is selected from the following five:

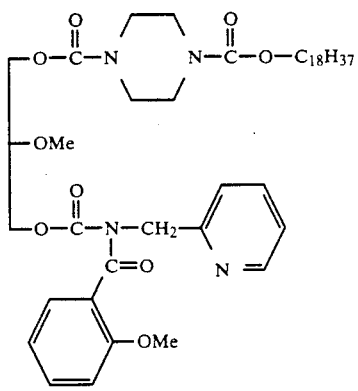
(1)

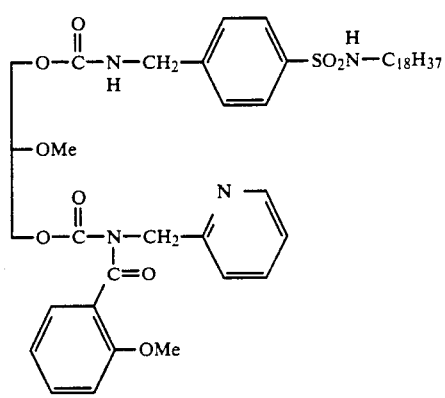
(2)
(3)

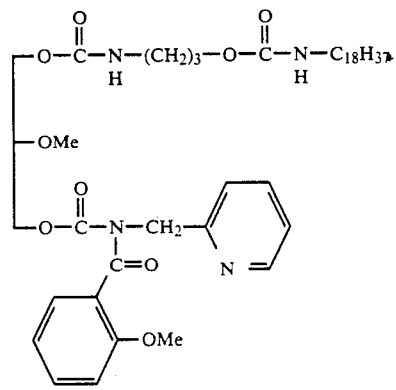
(4)

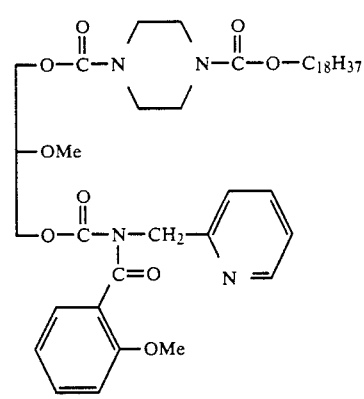

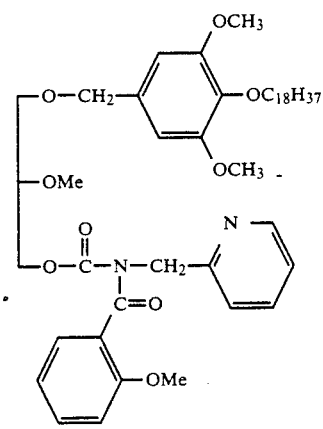
(5)

The salt of the glycerin derivative is more effective, especially having a pyridinium salt having the formula for G as defined above in which R17 is ethyl and X is chlorine.

It is preferable in the formula (I') that A is (1), R1 and R3 each are methoxy, R2 is an alkoxy having 14 to 22, B is methyl, D is —OCO—NR4—(CH2)q—G, R4 is o-, m- or p-methoxybenzoyl, q is 1, G is pyridium having the formula:

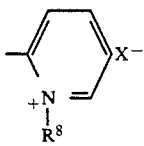

R8 is a lower alkyl and X is a halogen.

The invention will be explained below more in details in reference to the two embodiments (I) and (I').

GLYCERIN DERIVATIVE (I)

The glycerol derivatives of the above general formula (I) are characterized in that they are excellent in not only a PAF-inhibiting effect but also the persistence of this effect and the stability of the compounds themselves.

Therefore, an object of the present invention is to provide new glycerol derivatives and pharmacologically acceptable salts of them having an excellent PAF-inhibiting effect. Another object of the present invention is to provide a process for producing them. A further object of the present invention is to provide medicines containing them.

The term "lower alkyl groups" in the definition of $R^{11}$, $R^{12}$, $R^{14}$, $R^{15}$, $R^{17}$ and B refers to straight-chain or branched alkyl groups having 1 to 6 carbon atoms, such as methyl, ethyl, n-propyl, n-butyl, isopropyl, isobutyl, n-heptyl, 1-ethylpropyl, isoamyl and n-hexyl groups.

The term "alkyl groups" in the definition of $R^5$, $R^6$, $R^7$, $R^8$, $R^{10}$ and $R^{16}$ refers to the above-described straight-chain or branched alkyl groups, i.e., straight-chain or branched lower alkyl groups having 1 to 6 carbon atoms, such as methyl, ethyl, n-propyl, n-butyl, isopropyl, isobutyl, n-heptyl, 1-ethylpropyl, isoamyl and n-hexyl groups as well as other alkyl groups such as heptyl, octyl, nonyl, decyl, undecyl, dodecyl, tridecyl, tetradecyl, pentadecyl, hexadecyl, heptadecyl, octadecyl, nonadecyl, eicosanyl, heneicosanyl, docosanyl, tricosanyl, tetracosanyl, pentacosanyl, hexacosanyl, heptacosanyl, octacosanyl, nonacosanyl and triacontanyl groups. Among them, alkyl groups having about 14 to 22 carbon atoms, particularly those having about 16 to 20 carbon atoms, are preferred.

The term "lower alkoxy groups" in the definition of $R^2$, $R^3$ and $R^4$ refers to lower alkoxy groups derived from the above-described lower alkyl groups, namely those having 1 to 6 carbon atoms. The lower alkoxy groups of "lower alkoxycarbonyl groups" in the definition of $R^{13}$ are those having 1 to 6 carbon atoms as described above. The term "alkoxy groups" in the definition of $R^6$ and $R^7$ refers to those derived from the above-described alkyl groups.

The term "aryl groups" in the definition of $R^5$, $R^6$ and $R^9$ refers to substituted or unsubstituted phenyl group, naphthyl group, fluorenyl group, etc. such as a pheny group, a group of the formula:

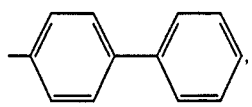

a group of the formula

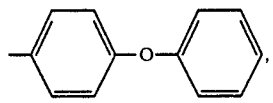

a group or the formula:

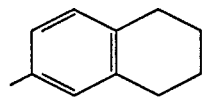

and a group of the formula:

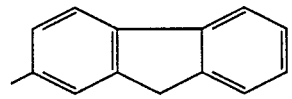

which may be substituted with a lower alkyl group, a halogen atom or the like.

The term "arylalkyl groups" in the definition of $R^5$ and B refers to arylalkyl groups derived from the above-described aryl groups.

The symbols m, p, q, r, t, u, y and z in the definition of A refer to integers of 0 to 6, preferably about 1 to 3, each representing the number of the methylene units.

The term "acyl groups" in the definition of $R^1$ refers to the residues of organic acids such as aliphatic saturated carboxylic acids, aliphatic unsaturated carboxylic acids, carbocylic carboxylic acids and heterocyclic carboxylic acids. They include, for example, lower alkanoyl groups such as formyl, acetyl, propionyl, butyryl, isobutyryl, valeryl, isovaleryl and pivaloyl groups; substituted or unsubstituted aroyl groups such as benzoyl, toluoyl and naphthoyl groups; heteroaroyl groups such as furoyl, nicotinoyl and isonicotinoyl groups; and cyclohexylcarbonyl group. Among them, preferred are lower alkanoyl groups such as acetyl and propionyl groups and substituted or unsubstituted benzoyl group and the most preferred are, for example, an acetyl group and o-, m- and p-methoxybenzoyl groups.

The group A comprises those of categories (1) to (11). Among them, a compound having a group of category (3) is the most preferred, and those having a group of category (2) and category (10) are next preferred.

Among the groups of category (3), those in which $R^6$ is a group of the formula:

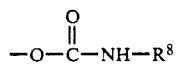

($R^8$ being a hydrogen atom or an alkyl group) are particularly preferred.

The alkyl group of $R^8$ is a straight-chain or branched alkyl group having 1 to 30 carbon atoms as described above, preferably one having about 14 to 22 carbon atoms and particularly one having about 16 to 20 carbon atoms.

The group

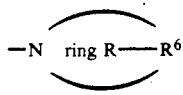

in the definition in category (3) is a ring which may comprise a nitrogen or oxygen atom in addition to carbon atoms. Preferred examples thereof include the following groups:

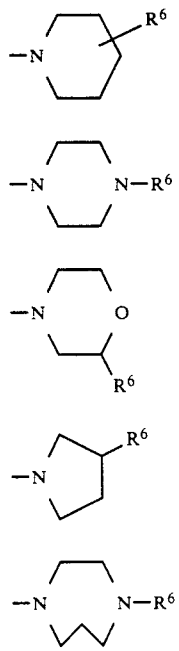

Among them, the most preferred is one having a piperidine ring (1).

The compounds of the present invention are glycerol derivatives of the above formula (I) and pharmacologically acceptable salts of them, such as hydrochlorides, hydrobromides, hydroiodides, sulfates and phosphates of them. Among them, quaternary salts of the above general formula wherein G represents

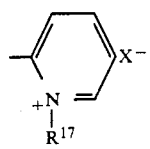

are the most preferred in the present invention.

$R^{17}$ is a lower alkyl group as described above. It has preferably about 1 to 3 carbon atoms and is most preferably an ethyl group.

$X^-$ is a pharmacologically acceptable anion. The anions are not particularly limited and typical examples of them are acid anions such as chloride, bromide, iodide, sulfate, nitrate, phosphate and acetate ions as well as a hydroxide ion.

The compounds of the present invention each have an asymmetric carbon atom in the molecule so that they include various stereoisomers. As a matter of course, all of the stereoisomers and mixtures of then are within the scope of the present invention.

Typical production processes of the present invention will now be described.

PRODUCTION PROCESS 1

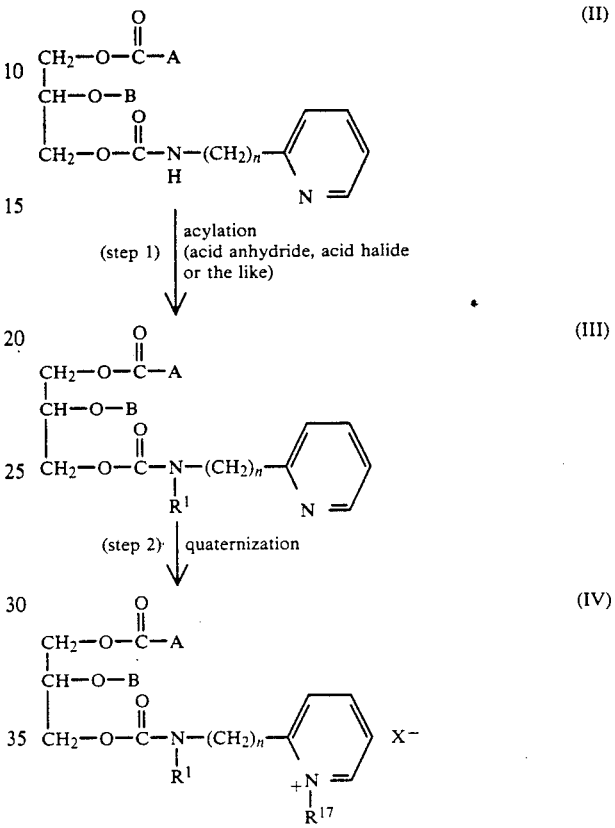

wherein A, B, n, $R^1$, $R^{17}$ and X are as defined above.

Step 1

In this step, a compound of the general formula (II) is acylated by an ordinary process to obtain a compound of the general formula (III).

In this acylation step, a reactive derivative of a carboxylic acid of the formula: $R^1OH$ ($R^1$ being an acyl group) such as anhydride or halide thereof is reacted with a compound of the general formula (II) to form an intended product of the general formula (III).

In the introduction of an acetyl group, desired results can be obtained when acetic anhydride is used.

This reaction is preferably conducted in the presence of a base.

The bases include alkali metal hydrides such as potassium hydride and sodium hydride; alkali metals such as metallic sodium; sodium alcoholates such as sodium methoxide; alkali hydroxides such as sodium hydroxide and potassium hydroxide; organic bases such as pyridine and triethylamine; and alkali carbonates such as potassium carbonate and sodium carbonate.

This reaction is conducted in a solvent selected from the group consisting of ethers such as tetrahydrofuran and diethyl ether; ketones such as acetone and methyl ethyl ketone; benzenoid solvents such as benzene and toluene; acetonitrile; dimethylformamide; dimethyl sulfoxide; and hexamethylphosphoric triamide.

The reaction temperature is suitably selected in the range of −78° C. to the boiling point of the solvent.

Step 2

The compound of the general formula (III) produced in the step 1 is quaternixed by an ordinary process to form a compound (IV) of the present invention. In this step, the compound of the general formula (III) is reacted with a compound of the general formula: $R^{17}$—X ($R^{17}$ and X being as defined above) to easily form an intended product (IV) of the present invention. When a hydrohalide thereof is to be produced, it is reacted with a compound of the formula: $R^{17}$—Hal.

This reaction is conducted preferably in nitrogen while shielding light. It is conducted without using any solvent or in a solvent selected from the group consisting of alcohols such as methanol and ethanol; ethers such as tetrahydrofuran and diethyl ether; ketones such as acetone and methyl ethyl ketone; benzenoid solvents such as benzene and toluene; acetonitrile; dimethylformamide; dimethyl sulfoxide; and hexamethylphosphoric triamide.

The reaction temperature is suitably selected in the range from a temperature realized by cooling with ice to the boiling point of the solvent.

The compounds of the general formula (II) used as the starting compound in the process of the present invention can be produced by, for example, any of the processes described below. These processes can be applied to any of the groups A of categories (1) to (11) except for those of category (3).

PRODUCTION PROCESS (I)

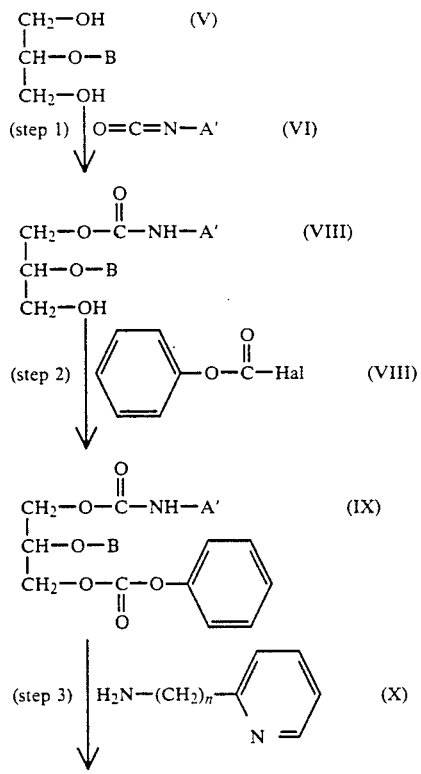

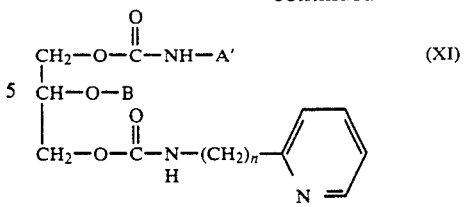

wherein B and n are as defined above, Hal represents a halogen atom and A′ represents a group formed by removing —NH— from group (1), (2), (4), (5), (6), (7), (8), (9), (10) or (11) in the definition of A.

Step 1

A compound of the general formula (V) is reacted with an isocyanate of the general formula (VI) in the presence of a base to form a compound of the general formula (VII).

The bases usable herein include pyridine, 4-(N,N-dimethylamino)pyridine and quinoline.

This reaction is conducted without using any solvent or in a solvent selected from the group consisting of ethers such as tetrahydrofuran and diethyl ether; and benzenoid solvents such as benzene, toluene and xylene.

The reaction temperature is suitably selected in the range from a temperature realized by cooling with ice to the boiling point of the solvent.

The isocyanate O=C=N—A′ used in this step can be produced by reacting a compound of the formula: A′—NH₂, such as 3,4,5-trimethoxyaniline, with phosgene, oxalyl dichloride or trichloromethyl chloroformate. The reaction is conducted usually in an inert organic solvent such as benzene, toluene or ethyl acetate.

The reaction temperature is suitably selected in the range from a temperature realized by cooling with ice to the boiling point of the solvent.

Step 2

In this step, a compound of the general formula (VII) is reacted with a phenyl haloformate in the presence of a base to form a compound (IX).

The bases usable herein include pyridine and triethylamine.

The reaction is conducted without using any solvent or in a solvent selected from the group consisting of chlorohydrocarbon solvents such as chloroform and methylene chloride; ethers such as tetrahydrofuran and diethyl ether; ketones such as acetone and methyl ethyl ketone; benzenoid solvents such as benzene and toluene; acetonitrile; dimethylformamide; dimethyl sulfoxide and hexamethylphosphoric triamide.

The reaction temperature is suitably selected in the range from −78° C. to the boiling point of the solvent.

Step 3

In this step, a compound of the general formula (IX) is reacted with an amine of the general formula (X) to form a compound of the general formula (XI). When n is 1, the compound (X) is 2-(aminomethyl)pyridine.

The reaction is conducted without using any solvent or in a solvent selected from the group consisting of chlorohydrocarbon solvents such as chloroform and methylene chloride; ethers such as tetrahydrofuran and diethyl ether; ketones such as acetone and methyl ethyl ketone; benzenoid solvents such as benzene and toluene;

acetonitrile; dimethylformamide; dimethyl sulfoxide; and hexamethylphosphoric triamide.

The reaction temperature is suitably selected in the range from a temperature realized by cooling with ice to the boiling point of the solvent.

The compounds of the general formula (XI) formed in this step correspond to those of the general formula (II) except when A is a group of category (3) in the definition of A in the general formula (I).

PRODUCTION PROCESS (II)

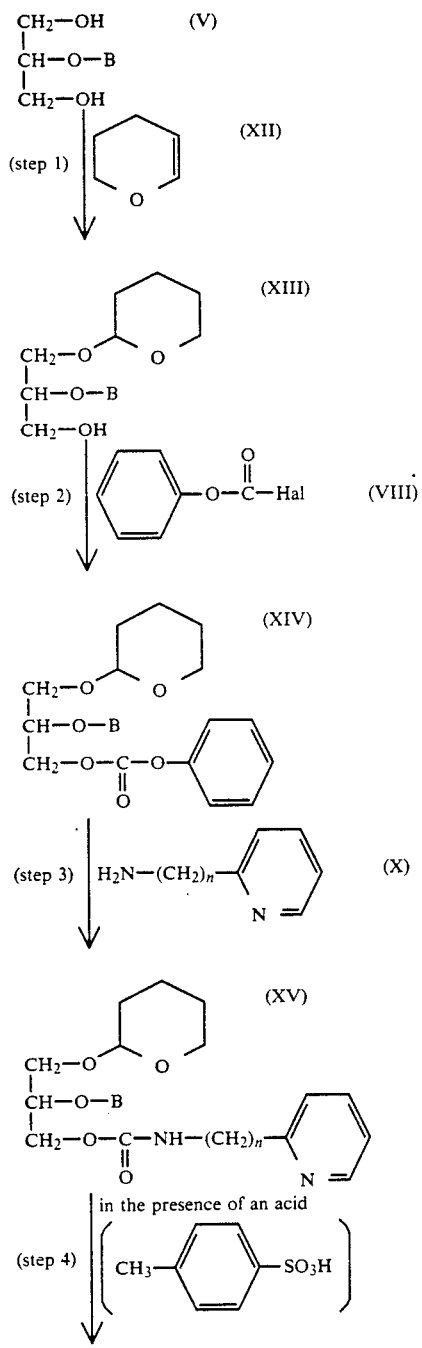

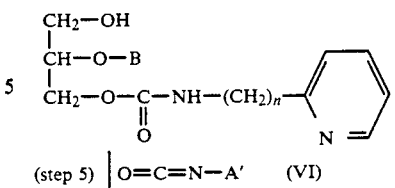

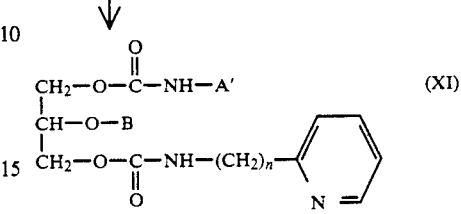

wherein B, A', n and Hal are as defined above.

Step 1

A compound of the general formula (V) is reacted with dihydropyran (XII) in the presence of an acid to form a compound of the general formula (XIII).

The acids usable herein include p-toluenesulfonic acid and pyridinium p-toluenesulfonate.

The reaction is usually conducted in a chlorocarbon solvent such as dichloromethane or chloroform, an ether such as tetrahydrofuran or diethyl ether, a benzenoid solvent such as benzene or toluene, or hexane.

The reaction temperature is suitably selected in the range from a temperature realized by cooling with ice to the boiling point of the solvent.

Step 2

A compound of the general formula (XIII) is reacted with a phenyl haloformate in the presence of a base to form a compound of the general formula (XIV).

The bases usable herein include pyridine and triethylamine.

The reaction is conducted without using any solvent or in a solvent selected from the group consisting of chlorohydrocarbon solvents such as chloroform and dichloromethane; ethers such as tetrahydrofuran and diethyl ether; ketones such as acetone and methyl ethyl ketone; benzenoid solvents such as benzene and toluene; acetonitrile; dimethylformamide; dimethyl sulfoxide; and hexamethylphosphoric triamide.

The reaction temperature is suitably selected in the range from $-78°$ C. to the boiling point of the solvent.

Step 3

A compound of the general formula (XIV) is reacted with an amine of the general formula (X) to form a compound of the general formula (XV).

The reaction is conducted without using any solvent or in a solvent selected from the group consisting of chlorohydrocarbon solvents such as chloroform and dichloromethane; ethers such as tetrahydrofuran and diethyl ether; ketones such as acetone and methyl ethyl ketone; benzenoid solvents such as benzene and toluene; acetonitrile; dimethylformamide; dimethyl sulfoxide; and hexamethylphosphoric triamide.

The reaction temperature is suitably selected in the range from a temperature realized by cooling with ice to the boiling point of the solvent.

Step 4

A compound of the general formula (XV) is reacted with water or an alcohol such as methanol or ethanol in the presence of an acid to form a compound of the general formula (XVI).

The acids include p-toluenesulfonic acid, acetic acid, pyridinium p-toluenesulfonate and hydrochloric acid.

The reaction is conducted without using any solvent or in a solvent selected from the group consisting of alcohols such as methanol and ethanol; water; ethers such as tetrahydrofuran and diethyl ether; ketones such as acetone and methyl ethyl ketone; benzenoid solvents such as benzene and toluene; acetonitrile; dimethylformamide; dimethyl sulfoxide; and hexamethylphosphoric triamide.

The reaction temperature is suitably selected in the range from a temperature realized by cooling with ice to the boiling point of the solvent.

Step 5

An isocyanate represented by the general formula: $O=C=N-A'$ (VI) is reacted with a compound of the general formula (XVI) in the present of a base by an ordinary process to form a compound of the general formula (XI):

The bases include pyridine, 4-(N,N-dimethylamine)-pyridine and quinoline.

The reaction is conducted without using any solvent or in a solvent selected from the group consisting of ethers such as tetrahydrofuran and diethyl ether; and benzenoid solvents such as benzene and toluene.

The reaction temperature is suitably selected in the range from a temperature realized by cooling with ice to the boiling point of the solvent,

PRODUCTION PROCESS (III)

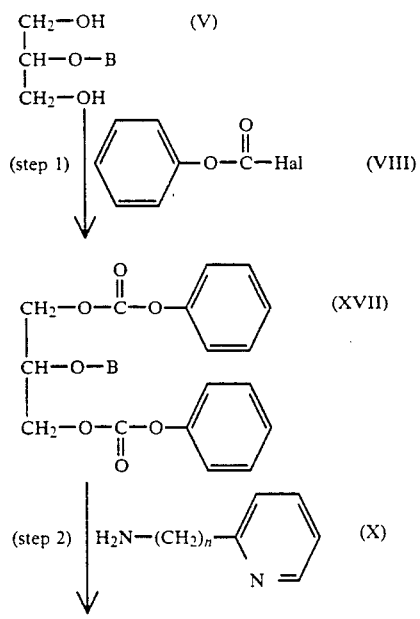

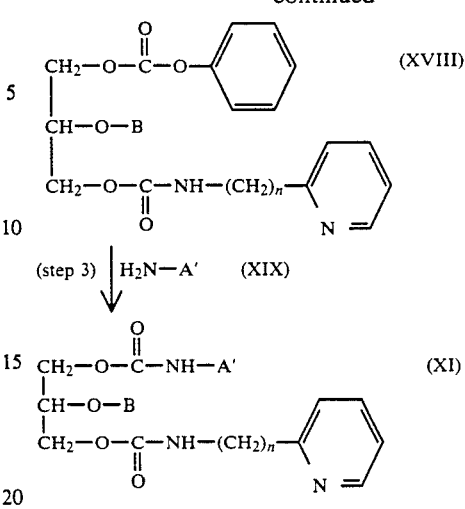

wherein A', n, B and Hal are as defined above.

Step 1

A glycerol derivative of the general formula (V) is condensed with a phenyl haloformate (VIII) by an ordinary process to form a compound of the general formula (XVIII).

The reaction is preferably conducted in the presence of a base such as an amine, e.g. triethylamine or pyridine, an alkali metal hydride, e.g. sodium hydride or potassium hydride, an alkali metal, e.g. metallic sodium, or an alkali hydroxide, e.g. sodium hydroxide or potassium hydroxide.

The reaction is conducted without using any solvent or in a solvent selected from the group consisting of ethers such as tetrahydrofuran and dioxane; halogenated solvents such as methylene chloride and chloroform; benzenoid solvents such as benzene, toluene and xylene; dimethylformamide; and dimethyl sulfoxide.

The reaction temperature is suitably selected in the range from a temperature realized by cooling with ice to the boiling point of the solvent.

Step 2

The dicarbonate (XVII) formed in the above-described step 1 is reacted with an amine of the general formula (X) to form a compound of the general formula (XVIII).

The reaction is conducted without using any solvent or in a solvent selected from the group consisting of halogenated solvents such as chloroform and methylene chloride; ethers such as tetrahydrofuran; and benzenoid solvents such as benzene and toluene.

The reaction temperature is suitably selected in the range from room temperature to the boiling point of the solvent.

Step 3

The carbamoyl derivative (XVIII) formed in the above-described step 2 is reacted with an amine of the general formula: $H_2N-A'$ (XIX) to form a compound of the general formula (XI).

The reaction is conducted without using any solvent or in a solvent selected from the group consisting of halogenated solvents such as chloroform and methylene chloride; ethers such as tetrahydrofuran; and benzenoid solvents such as benzene and toluene.

The reaction temperature is suitably selected in the range from room temperature to the boiling point of the solvent.

PRODUCTION PROCESS 2

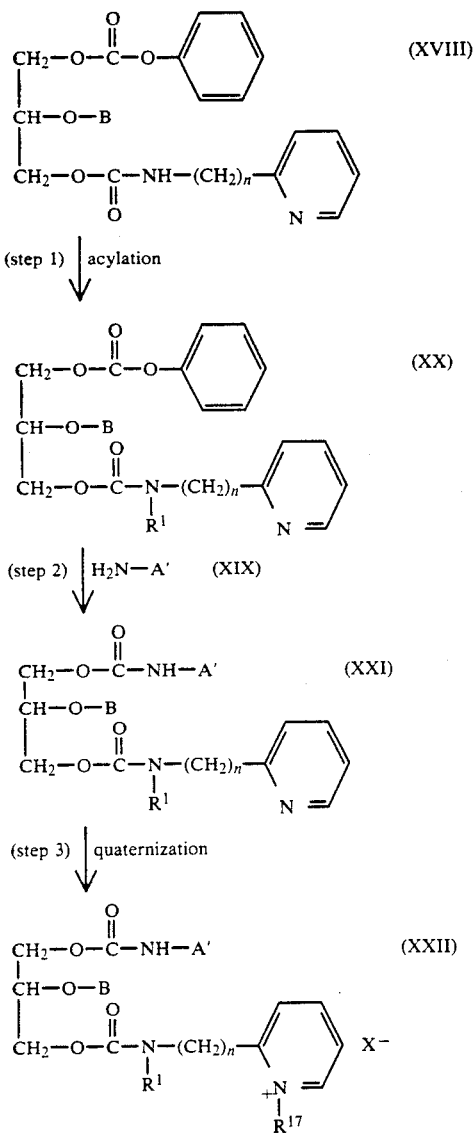

wherein $R^{17}$, n, A', B, $R^1$ and X are as defined above.

Step 1

A compound of the general formula (XVIII) is acylated by an ordinary process to form a compound of the general formula (XX).

In the acylation, for example, a reactive derivative of a carboxylic acid of the formula: $R^1OH$ ($R^1$ being an acyl group) such as an anhydride or halide thereof is reacted with a compound of the general formula (XVIII) to form a compound of the general formula (III) which is one of the intended products.

When an acetyl group is to be introduced, acetic anhydride is preferably used to obtain good results.

The reaction is conducted preferably in the presence of a base.

Step 2

A compound of the general formula (XX) is reacted with an amine of the general formula: $H_2N-A'$ to form a compound of the general formula (XXI).

The reaction is conducted without using any solvent or in a solvent selected from the group consisting of halogenated solvents such as chloroform and methylene chloride; ethers such as tetrahydrofuran; and benzenoid solvents such as benzene and toluene.

The reaction temperature is suitably selected in the range from room temperature to the boiling point of the solvent.

Step 3

The quaternization is conducted by the same process as that in the step 2 of the production process 1.

PRODUCTION PROCESS 3

When A in the general formula (I) is a group of the formula:

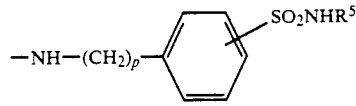

wherein p and $R^5$ are as defined above, the intended product can be formed also by the following process:

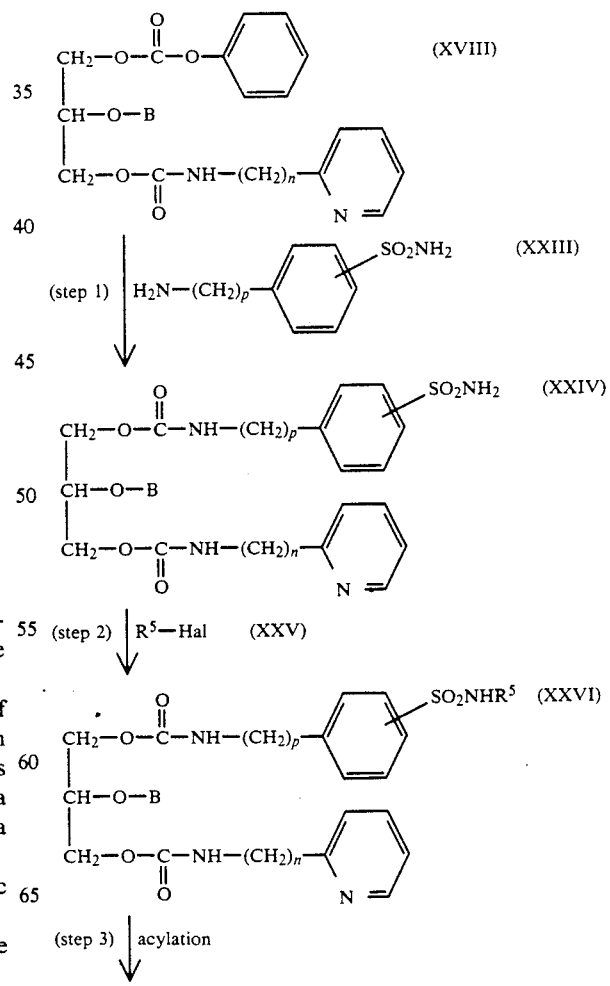

-continued $$CH_2-O-\overset{O}{\underset{\|}{C}}-NH-(CH_2)_p-\underset{}{\underset{}{\bigcirc}}^{SO_2NHR^5} \quad (XXVII)$$
$$CH-O-B$$
$$CH_2-O-\underset{\|}{\underset{O}{C}}-\underset{|}{\underset{R^1}{N}}-(CH_2)_n-\underset{N=}{\bigcirc}$$

(step 4) ↓ quaternization $$CH_2-O-\overset{O}{\underset{\|}{C}}-NH-(CH_2)_p-\underset{}{\underset{}{\bigcirc}}^{SO_2NHR^5} \quad (XXVIII)$$
$$CH-O-B$$
$$CH_2-O-\underset{\|}{\underset{O}{C}}-\underset{|}{\underset{R^1}{N}}-(CH_2)_n-\underset{\underset{|}{+N=}}{\bigcirc} \quad X^-$$
$$\phantom{CH_2-O-C-N-(CH_2)_n-N}R^{17}$$

wherein $R^{17}$, n, $R^5$, p, B, $R^1$, Hal and X are as defined above.

Step 1

A compound of the general formula (XVIII) is reacted with a sulfamoylphenylalkylamine (XXIII) to form a compound of the general formula (XXIV).

The reaction is conducted without using any solvent or in a solvent selected from the group consisting of halogenated solvents such as chloroform and methylene chloride; ethers such as tetrahydrofuran; and benzenoid solvents such as benzene and toluene.

The reaction temperature is suitably selected in the range from room temperature to the boiling point of the solvent.

Step 2

The compound of the general formula (XXIV) formed in the step 1 is reacted with an alkyl halide of the general formula (XXV) to form a compound of the general formula (XXVI).

The reaction is preferably conducted in the presence of a base selected from the group consisting of alkali carbonates such as potassium carbonate; alkali hydroxides such as sodium hydroxide and potassium hydroxide; amines such as triethylamine and pyridine; and alkali metal hydrides such as sodium hydride and potassium hydride.

The reaction is conducted without using any solvent or in a solvent selected from the group consisting of ethers such as tetrahydrofuran and dioxane; halogenated solvents such as methylene chloride and chloroform; benzenoid solvents such as benzene and toluene; dimethylformamide and dimethyl sulfoxide.

The reaction temperature is suitably selected in the range from a temperature realized by cooling with ice to the boiling point of the solvent.

Step 3

The compound of the general formula (XXVI) formed in the step 2 is acylated into a compound of the general formula (XXVII) by an ordinary process.

In the acylation, or example, a reactive derivative of a carboxylic acid of the formula: $R^1OH$ ($R^1$ being an acyl group) such as an anhydride or halide thereof is reacted with a compound of the general formula (XXVI) to form a compound of the general formula (XXVII).

When an acetyl group is to be introduced, acetic anhydride is preferably used to obtain good results.

The reaction is preferably conducted in the presence of a base such as an amine, e.g. triethylamine or pyridine, an alkali metal hydride, e.g. sodium hydride or potassium hydride, an alkali metal, e.g. metallic sodium, or an alkali hydroxide, e.g. sodium hydroxide or potassium hydroxide.

The reaction is conducted without using any solvent or in a solvent selected from the group consisting of ethers such as tetrahydrofuran; halogenated solvents such as methylene chloride and chloroform, benzenoid solvents such as benzene and toluene; dimethylformamide; and dimethyl sulfoxide.

The reaction temperature is suitably selected in the range from a temperature realized by cooling with ice to the boiling point of the solvent.

Step 4

The compound of the general formula (XXVII) formed in the step 3 is quaternized into a compound (XXVIII) of the present invention by an ordinary process. In this step, the compound of the general formula (XXVII) is reacted with a compound of the general formula: $R^{17}$—X ($R^{17}$ and X being as defined above) to easily form the intended compound (XXVIII) of the present invention. When its hydrohalide is to be produced, $R^{17}$—Hal ($R^{17}$ being hydrogen) is used.

The reaction is conducted preferably in nitrogen while shielding light. The reaction is conducted without using any solvent or in a solvent selected from the group consisting of alcohols such as methanol and ethanol; ethers such as tetrahydrofuran and diethyl ether; ketones such as acetone and methyl ethyl ketone; benzenoid solvents such as benzene and toluene; acetonitrile; dimethylformamide; dimethyl sulfoxide; and hexamethylphosphoric triamide.

The reaction temperature is suitably selected in the range from a temperature realized by cooling with ice to the boiling point of the solvent.

PRODUCTION PROCESS 4

When A in the general formula (I) is a group of category (10)

$$-NH-(CH_2)_y-O-\overset{O}{\underset{\|}{C}}-NH-R^{16}$$

(y being a number of 0 to 6 and $R^{16}$ being a hydrogen atom or an alkyl group), the compound can be produced also by the following process:

$$CH_2-O-\overset{O}{\underset{\|}{C}}-O-\underset{}{\underset{}{\bigcirc}} \quad (XVIII)$$
$$CH-O-B$$
$$CH_2-O-\underset{\|}{\underset{O}{C}}-NH-(CH_2)_n-\underset{N=}{\bigcirc}$$

(step 1) ↓ $H_2N-(CH_2)_y-OH$    (XXIX)

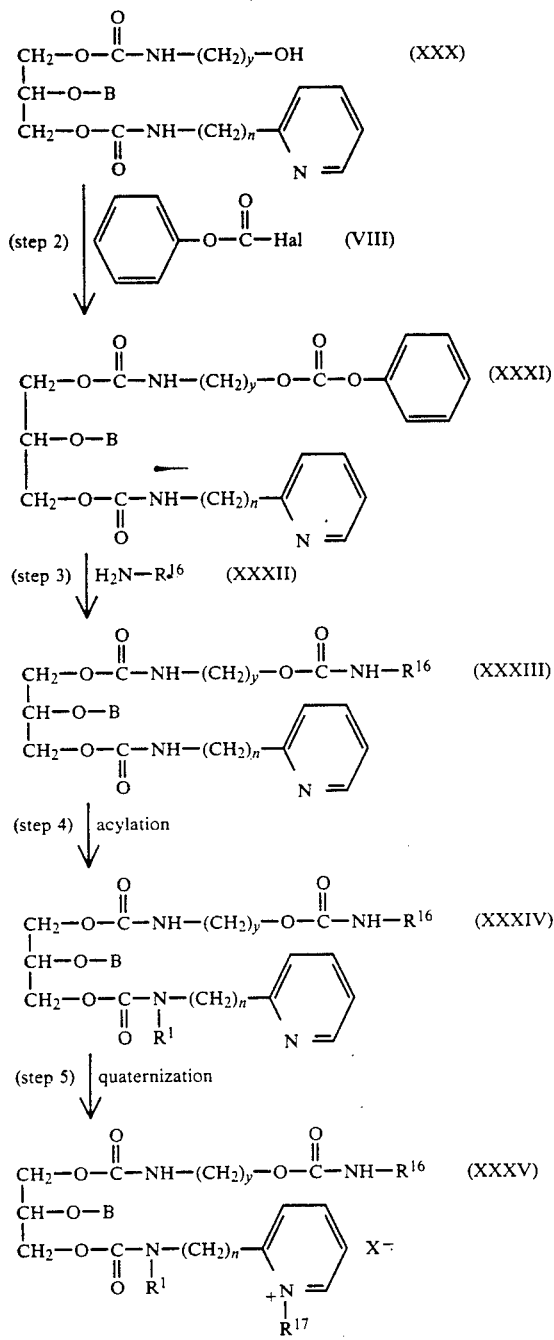

wherein $R^{17}$, n, $R^1$, y, $R^{16}$, B and Hal are as defined above.

Step 1

A carbamoyl derivative (XVIII) is reacted with an amine of the general formula (XXIX) to form a compound of the general formula (XXX).

The reaction is conducted without using any solvent or in a solvent selected from the group consisting of halogenated solvents such as chloroform and methylene chloride; ethers such as tetrahydrofuran; and benzenoid solvents such as benzene and toluene.

The reaction temperature is suitably selected in the range from room temperature to the boiling point of the solvent.

Step 2

The compound of the general formula (XXX) is condensed with a phenyl haloformate (VIII) by an ordinary process to form a compound of the general formula (XXXI).

The reaction is conducted preferably in the presence of a base such as an amine, e.g. triethylamine or pyridine, an alkali metal hydride, e.g. sodium hydride or potassium hydride, an alkali metal, e.g. metallic sodium, or an alkali hydroxide, e.g. sodium hydroxide or potassium hydroxide.

The reaction is conducted without using any solvent or in a solvent selected from the group consisting of ethers such as tetrahydrofuran and dioxane; halogenated solvents such as methylene chloride and chloroform; benzenoid solvents such as benzene, toluene and xylene; dimethylformamide; and dimethyl sulfoxide.

The reaction temperature is suitably selected in the range from a temperature realized by cooling with ice to the boiling point of the solvent.

Step 3

The carbamoyl derivative (XXXI) formed in the above-described step 2 is reacted with an amine of the general formula (XXXII) to form a compound of the general formula (XXXIII).

The reaction is conducted without using any solvent or in a solvent selected from the group consisting of halogenated solvents such as chloroform and methylene chloride; ethers such as tetrahydrofuran; and benzenoid solvents such as benzene and toluene.

The reaction temperature is suitably selected in the range from room temperature to the boiling point of the solvent.

Step 4

The compound of the general formula (XXXIII) formed in the step 3 is acylated into a compound of the general formula (XXXIV) by an ordinary process.

In the acylation, for example, a reactive derivative of a carboxylic acid of the formula: $R^1OH$ ($R^1$ being an acyl group) such as an anhydride or halide thereof is reacted with a compound of the general formula (XXXIII) to form a compound of the general formula (XXXIV).

When an acetyl group is to be introduced, acetic anhydride is preferably used to obtain good results.

The reaction is conducted preferably in the presence of a base such as an amine, e.g. triethylamine or pyridine, an alkali metal hydride, e.g. sodium hydride or potassium hydride, an alkali metal, e.g. metallic sodium, or an alkali hydroxide, e.g. sodium hydroxide or potassium hydroxide.

The reaction is conducted without using any solvent or in a solvent selected from the group consisting of ethers such as tetrahydrofuran; halogenated solvents such as methylene chloride and chloroform; benzenoid solvents such as benzene and toluene; dimethylformamide; and dimethyl sulfoxide.

The reaction temperature is suitably selected in the range from a temperature realized by cooling with ice to the boiling point of the solvent.

Step 5

The compound of the general formula (XXXIV) formed in the step 4 is quaternized into a compound (XXXV) of the present invention. In this step, the compound of the formula (XXXIV) is reacted with a compound of the general formula: $R^{17}$—X ($R^{17}$ and X being as defined above) to easily obtain a compound (XXXV), an intended product of the present invention. When its hydrohalide is to be produced, $R^{17}$—Hal ($R^{17}$ being hydrogen) is used.

The reaction is conducted preferably in nitrogen while shielding light. The reaction is conducted without using any solvent or in a solvent selected from the group consisting of alcohols such as methanol and ethanol; ethers such as tetrahydrofuran and diethyl ether; ketones such as acetone and methyl ethyl ketone; benzenoid solvents such as benzene and toluene; acetonitrile; dimethylformamide; dimethyl sulfoxide; and hexamethylphosphoric triamide.

The reaction temperature is suitably selected in the range from a temperature realized by cooling with ice to the boiling point of the solvent.

The compound of the general formula (XXXIII) used in the production process 4 can be directly formed also from a compound of the general formula (XXX) by the following process:

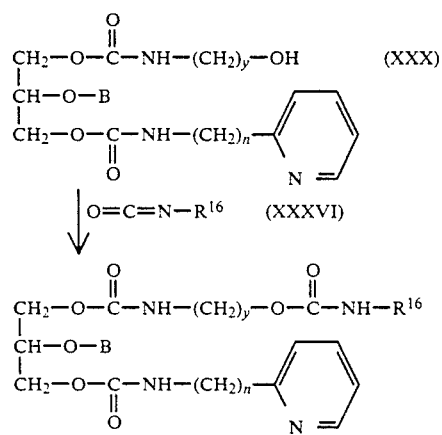

wherein $R^{16}$, n, y and B are as defined above.

In this process, the compound of the general formula (XXXIII) can be obtained by reacting the compound of the general formula (XXX) with the compound of the general formula (XXXVI).

The reaction is conducted preferably in the presence of an amine such s triethylamine or pyridine.

The reaction is conducted without using any solvent or in a solvent selected from the group consisting of ethers such as tetrahydrofuran; halogenated solvents such as methylene chloride and chloroform; and benzenoid solvents such as benzene and toluene.

The reaction temperature is suitably selected in the range from a temperature realized by cooling with ice to the boiling point of the solvent.

PRODUCTION PROCESS 5

When A in the general formula (I) is a group of category (3)

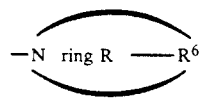

($R^6$ and the ring R are as defined above), the compound can be produced also by the following process:

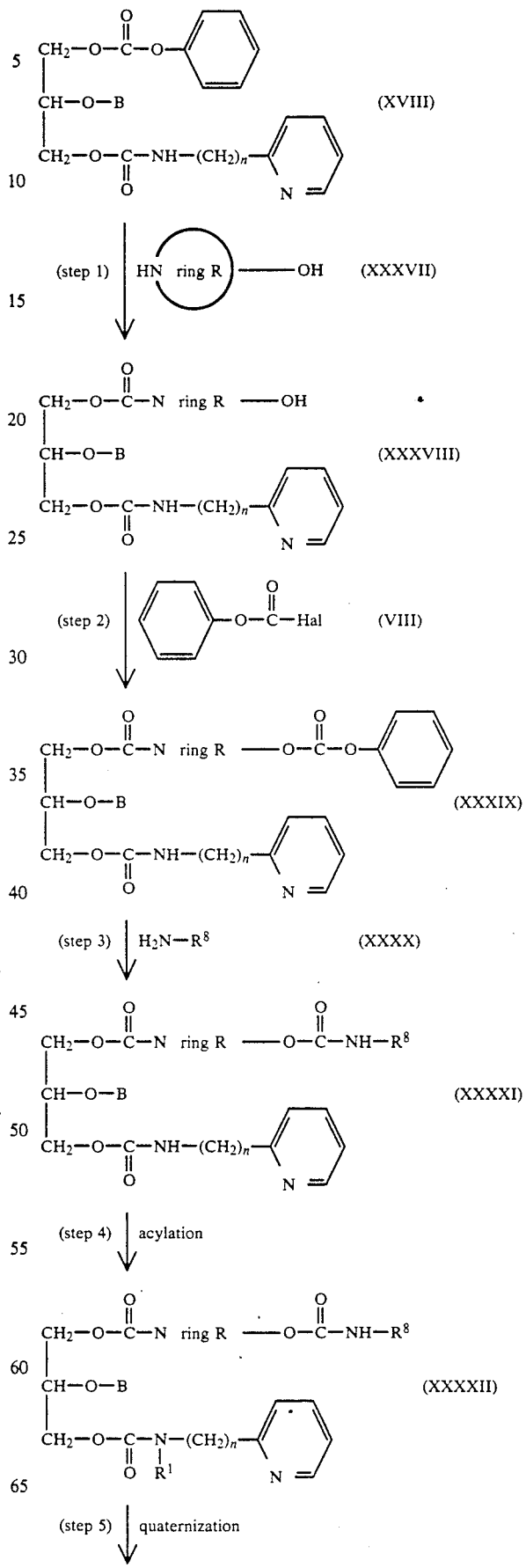

-continued

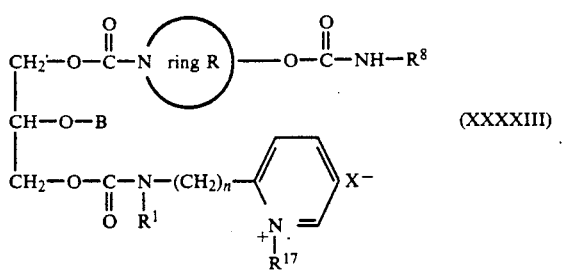

(XXXXIII)

wherein $R^{17}$, X, $R^1$, n, $R^8$, ring R, B and Hal are as defined above.

Step 1

A compound of the general formula (XVIII) is reacted with a cyclic amine of the general formula (XXXVII) to form a compound of the general formula (XXXVIII).

The reaction is conducted without using any solvent or in a solvent selected from the group consisting of chlorohydrocarbon solvents such as chloroform and methylene chloride; ethers such as tetrahydrofuran and diethyl ether; ketones such as acetone and methyl ethyl ketone; benzenoid solvents such as benzene and toluene; acetonitrile; dimethylformamide; dimethyl sulfoxide; and hexamethylphosphoric triamide.

The reaction temperature is suitably selected in the range from a temperature realized by cooling with ice to the boiling point of the solvent.

Step 2

The compound of the general formula (XXXVIIII) formed in the step 1 is reacted with a phenyl haloformate (VIII) in the presence of a base to form a compound of the general formula (XXXIX).

The bases usable herein include pyridine and triethylamine.

The reaction is conducted without using any solvent or in a solvent selected from the group consisting of chlorohydrocarbon solvents such as chloroform and methylene chloride; ethers such as tetrahydrofuran and diethyl ether; ketones such as acetone and methyl ethyl ketone; benzenoid solvents such as benzene and toluene; acetonitrile; dimethylformamide; dimethyl sulfoxide; and hexamethylphosphoric triamide.

The reaction temperature is suitably selected in the range from $-78°$ C. to the boiling point of the solvent.

Step 3

The compound of the general formula (XXXIX) formed in the step 2 is reacted with an amine of the general formula (XXXX) to form a compound of the general formula (XXXXI).

The reaction is conducted without using any solvent or in a solvent selected from the group consisting of chlorohydrocarbon solvents such as chloroform and methylene chloride; ethers such as tetrahydrofuran and diethyl ether; ketones such as acetone and methyl ethyl ketone; benzenoid solvents such as benzene and toluene; acetonitrile; dimethylformamide; dimethyl sulfoxide; and hexamethylphosphoric triamide.

The reaction temperature is suitably selected in the range from a temperature realized by cooling with ice to the boiling point of the solvent.

Step 4

The compound of the general formula (XXXXI) formed in the step 3 is acylated into a compound of the general formula (XXXXII) by an ordinary process.

In the acylation, for example, a reactive derivative of a carboxylic acid of the formula: $R^1OH$ ($R^1$ being an acyl group) such as an anhydride or halide thereof is reacted with a compound of the general formula (XXXXI) to form a compound of the general formula (XXXXII).

When an acetyl group is to be introduced, acetic anhydride is preferably used to obtain good results.

The reaction is conducted preferably in the presence of a base such as an amine, e.g. triethylamine or pyridine, an alkali metal hydride such as sodium hydride or potassium hydride, an alkali metal such as metallic sodium, or an alkali hydroxide such as sodium hydroxide or potassium hydroxide.

The reaction is conducted without using any solvent or in a solvent selected from the group consisting of ethers such as tetrahydrofuran; halogenated solvents such as methylene chloride and chloroform; benzene solvents such as benzene and toluene; dimethylformamide; and dimethyl sulfoxide.

The reaction temperature is suitably selected in the range from a temperature realized by cooling with ice to the boiling point of the solvent.

Step 5

The compound of the general formula (XXXXII) formed in the step 4 is quaternized into a compound (XXXXIII) of the present invention by an ordinary process. In particular, the compound of the general formula (XXXXII) is reacted with a compound of the general formula: $R^{17}$—X ($R^{17}$ and X being as defined above) to easily obtain a compound (XXXXIII), an intended product of the present invention. When a hydrohalide thereof is to be produced, $R^{17}$—Hal ($R^{17}$ being H) is used.

The reaction is conducted preferably in nitrogen while shielding light. The reaction is conducted without using any solvent or in a solvent selected from the group consisting of alcohols such as methanol and ethanol; ethers such as tetrahydrofuran and diethyl ether; ketones such as acetone and methyl ethyl ketone; benzenoid solvents such as benzene and toluene; acetonitrile; dimethylformamide; dimethyl sulfoxide; and hexamethylphosphoric triamide.

The reaction temperature is suitably selected in the range from a temperature realized by cooling with ice to the boiling point of the solvent.

The compound of the general formula (XXXXI) produced in the above-described production process 5 can be directly produced also from a compound of the general formula (XXXVIII) by the following process:

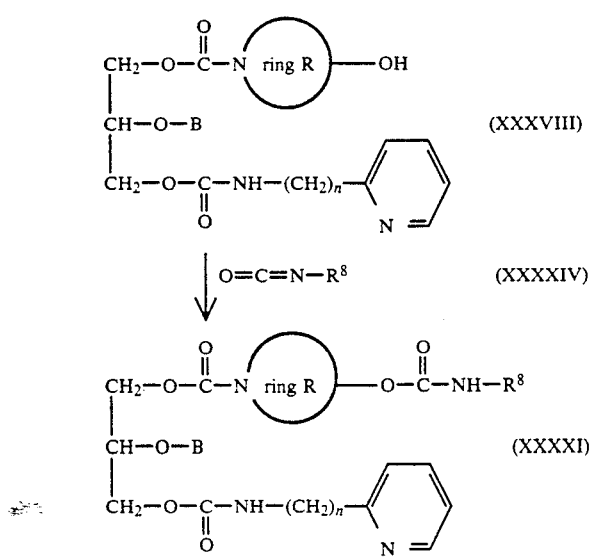

Namely, the compound of the general formula (XXXVIII) is reacted with an isocyanate of the general formula $O=C=N-R^8$ (XXXXIV) usually in the presence of a base to form the compound of the general formula (XXXXI).

The bases usable herein include pyridine, 4-(N,N-dimethylamino)pyridine and quinoline.

The reaction is conducted without using any solvent or in a solvent selected from the group consisting of ethers such as tetrahydrofuran and diethyl ether; and benzenoid solvents such as benzene and toluene.

The reaction temperature is suitably selected in the range from a temperature realized by cooling with ice to the boiling point of the solvent.

The isocyanate used in this step can be formed by the same process as that employed for the formation of the isocyanate in the step 1 of the production process 1-(i).

For facilitating the understanding of the process of the present invention, the process is illustrated as follows when n is 1 and A represents a group of the formula:

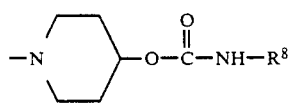

($R^8$ being a hydrogen atom or an alkyl group):

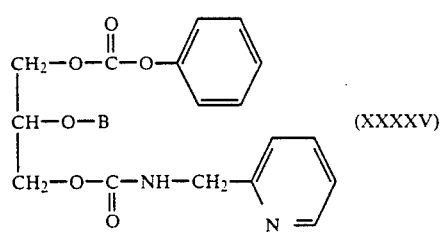

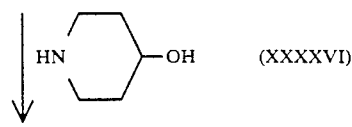

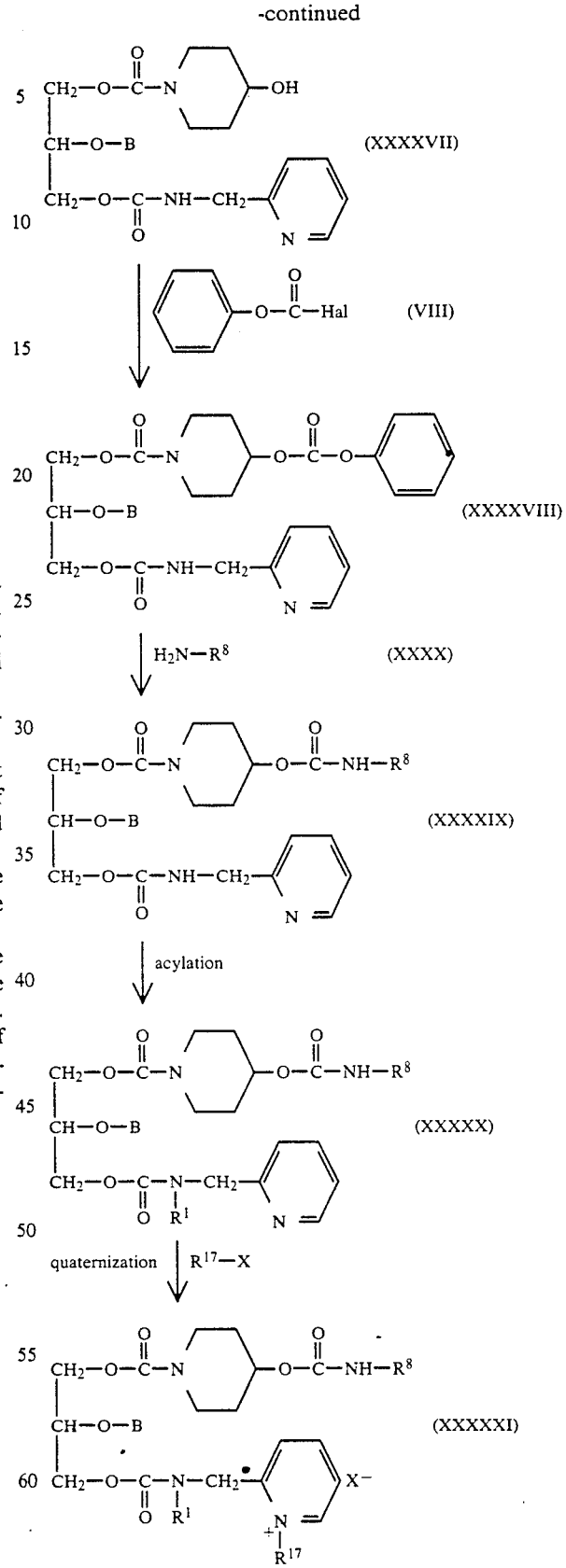

The compounds of the above general formula (XXXXIX) can be produced also by the following process:

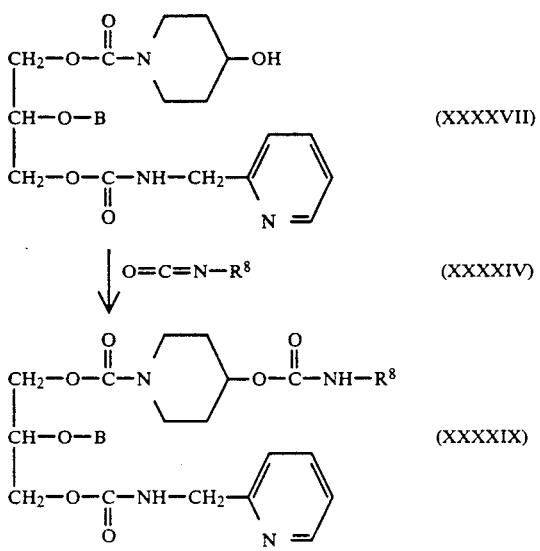

(XXXXVII)

(XXXXIV)

(XXXXIX)

GLYCERIN DERIVATIVE (I')

In other words, the glycerin derivative expressed in general formula (I') above has the characteristics of possessing superior PAF inhibitory action, demonstrating continuous action, and moreover, the compound itself is highly stable.

Therefore, the objective of this invention is to provide a new glycerin derivative or its pharmacologically allowable salt that possesses superior anti-PAF action, to provide a method for manufacturing these, and further, to provide a medical pharmaceutical that contains these.

The low order alkyl groups found in the definitions of B, $R^5$, $R^6$, $R^8$, $R^9$, $R^{10}$ and $R^{11}$ refer to straight-chain or branched alkyl groups having 1-6 carbons. Examples of such alkyl groups includes methyl, ethyl, n-propyl, n-butyl, isopropyl, isobutyl, n-peptyl, 1-ethylpropyl, isoamyl, or n-hexyl groups.

The alkoxy groups found in the definitions of $R^1$, $R^2$ and $R^3$ refer to low order alkoxy groups having 1-6 carbons which are derived from the above low order alkyl groups such as methoxy, ethoxy, propoxy and butoxy groups, as well as alkoxy groups derived from straight-chain or branched alkyl groups having 1-30 carbons. Preferably examples of alkoxy groups include methoxy, ethoxy and propoxy groups, as well as alkoxy groups having on the order of 14-22 carbons. In this case, the most preferably case is when $R^1$, $R^2$ and $R^3$ are all methoxy groups.

Examples of the acyl groups given in the definitions of $R^4$ and $R^7$ are organic residues such as aliphatic saturated carboxylic acids, aliphatic unsaturated carboxylic acids, homocyclic carboxylic acids or heterocyclic carboxylic acids. Specific examples of these include low order alkanoyl groups such as formyl, acetyl, propionyl, butyryl, isopeptyryl and pivaloyl groups, substituted or non-substituted aloyl groups such as benzoyl, toluoyl, and naphthtoyl groups, heteroaloyl groups such as furoyl, nicotinoyl and isonicotinoyl groups, and cyclohexyl carbonyl groups. From among these, preferable groups include low order alkanoyl groups such as acetyl and propionyl groups, as well as substituted or nonsubstituted benzoyl groups. Examples of the most preferably groups include acetyl groups and ortho, meta and parametoxybenzoyl groups.

X indicates a pharmacologically allowable anion. Although any anion is acceptable, typical examples include acidic anions such as chlorine ion, bromine ion, iodine ion, sulfate ion, nitrate ion, phosphate ion and acetate ion, as well as hydroxide ions.

Although the compound of this invention possesses asymmetric carbons within their molecules and contain various stereoisomers, in this invention, it goes without saying that each of the individual asymmetric carbons and stereoisomers as well as any combinations of such are included in this invention.

The following indicates typical manufacturing methods of the compound of this invention.

MANUFACTURING METHOD 1

In the case of D in formula (I') being a group having the formula $-Y-(CH_2)_q-G$ (in the formula, Y, q and G have the definitions that were given previously), the compound of this invention can be manufactured using, for example, the method indicated below.

(1) In the case Y is a group indicated by the formula

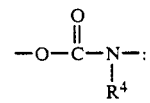

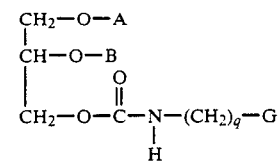

(II)

(Step 1)  Acylation
(Acid anhydride or acid halide expressed, for example, with the formula $R^4$—Hal (in the formula, Hal refers to a halogen atom).)

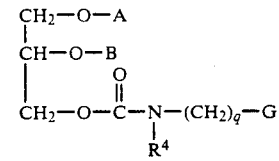

(III)

(In the formula, the definitions of A, B, q, G and $R^4$ are the same as those given previously.)

(2) In the case Y is a group indicated by the formula

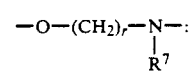

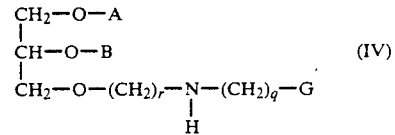

(IV)

(Step 2)  Acylation
(Acid anhydride or acid halide expressed, for example, with the formula $R^7$—Hal (in the formula, Hal refers to a halogen atom).)

-continued $$\begin{array}{c} CH_2-O-A \\ | \\ CH-O-B \\ | \\ CH_2-O-(CH_2)_r-N-(CH_2)_q-G \\ | \\ R^7 \end{array} \quad (V)$$

(In the formula, the definitions of A, B, r, q, G and $R^7$ are the same as those given previously.)

(3) In the case Y is a group indicated with the formula

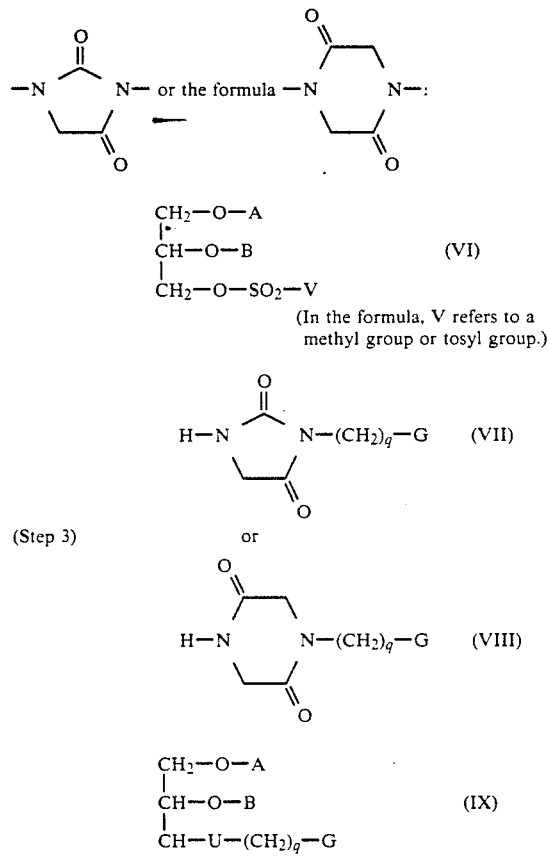

(In the formula, V refers to a methyl group or tosyl group.)

(Step 3)

(In the formula, U refers to a group indicated by the formula

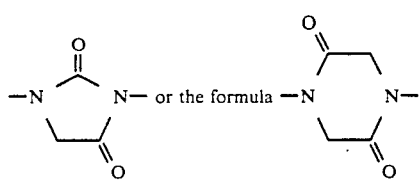

and the definitions of A, B, q and G are the same as those given previously.)

Step 1 and Step 2

These processes involve the procedure of acylation of the compounds expressed with general formulae (II) and (IV) using routine methods to obtain the respective corresponding compounds expressed with general formulae (III) and (V).

Acylation refers to the reaction of the compounds which are expressed with general formula (II) or general formula (IV) such as carboxyl reactive derivatives expressed with, for example, $R^4$—OH (in the formula, $R^4$ refers to an acyl group) or $R^7$—OH (in the formula, $R^7$ refers to an acyl group), or acid anhydrides or acid halides such as $R^4$—Hal or $R^7$—Hal, to form the compound expressed with general formula (III) or general formula (V), which is one of the target substances.

In the case of introduction of acetyl groups, in other words, in the case of $R^4$ or $R^7$ being an acetyl group, the use of acid anhydrides yields preferable results.

In addition, in the case $R^4$ is the group expressed with the formula

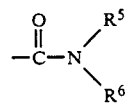

(in the formula, the definitions of $R^5$ and $R^6$ are the same as those given previously), the use of a carbamyl chloride such as one having the formula

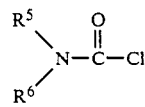

yields preferable results.

It is preferable that this reaction be allowed to react in the presence of base.

Examples of the base that is used include alkaline metal hydrides such as potassium hydride and sodium hydride, alkaline metals such as sodium metal, sodium alkoxides such as sodium methoxide, alkaline hydroxides such as sodium hydroxide and potassium hydroxide, organic bases such as pyridine and triethylamine, and alkaline carbonates such as potassium carbonate and sodium carbonate.

This reaction is conducted in the absence of a solvent or in the presence of a solvent which is selected from among, for example, ethers such as tetrahydrofuran and diethyl ether, ketones such as acetone and methylethyl ketone, benzene-based solvents such as benzene and toluene, acetonitrile, dimethyl formamide, dimethyl sulfoxide, or hexamethyl phosphate triamide.

The reaction temperature is suitably selected within a range from −78° C. to the boiling point of the solvent.

Step 3

This process involves the conducting of a substitution reaction in accordance with routine methods using the compound expressed with general formula (VI) to obtain the compound expressed with general formula (IX). In this substitution reaction, the target substance expressed with general formula (IX) is formed by reacting the anion, which is obtained by treating, for example, hydantoin derivative (VII) or diketopiperazine derivative (VIII) with base, with compound (VI).

Examples of the base that is used include alkaline metal hydrides such as potassium hydride and sodium hydride, alkaline metals such as sodium metal, and sodium alkoxides such as sodium methoxide.

This reaction is conducted in the presence of a solvent which is selected from ethers such as tetrahydrofuran and diethyl ether, dimethyl formamide, dimethyl sulfoxide, or hexamethyl phosphate triamide.

In the case of manufacturing the quaternary salt, compounds (III), (V) and (IX) which were manufactured by the methods described previously are formed into quaternary salts using, for example, the methods indicated below. Further, when compounds (III), (V) and (IX) are already in the form of quaternary salts, this procedure is of course not required.

(i) The case of manufacturing pyridinium salt is as indicated below:

(1) In the case Y is the group indicated with the formula

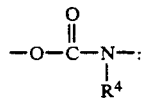

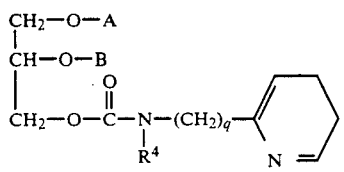 (X)

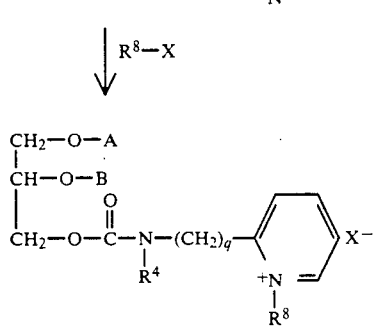 (XI)

(in this series of formulae, the definitions of A, B, R⁴, q, R⁸ and X are the same as those given previously.)

(2) In the case Y is the group indicated with the formula

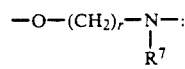

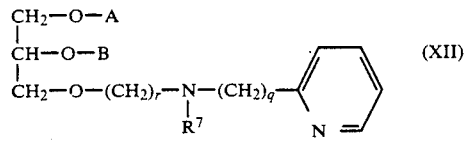 (XII)

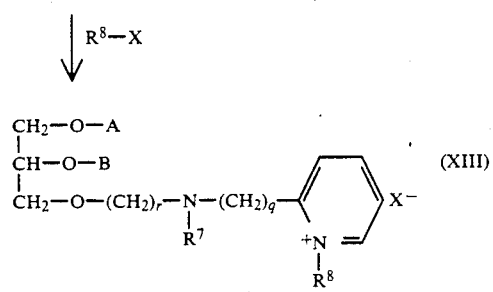 (XIII)

(In the above series of formulae, the definitions of A, B, R⁷, r, q, R⁸ and X are the same as those given previously.)

(3) In the case Y is the group indicated by the formula —U—:

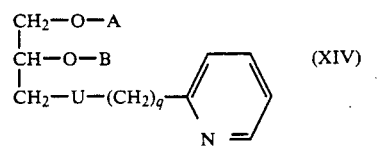 (XIV)

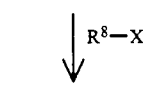

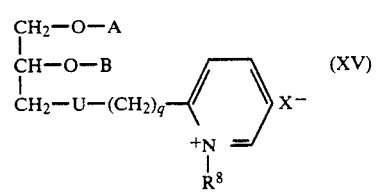 (XV)

(In the formula, the definitions of A, B, U, q, R⁸ and X are the same as those given previously.)

(ii) The case when G is the group indicated by the formula

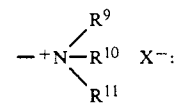

(1) The case when Y is the group indicated with the formula

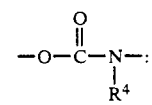

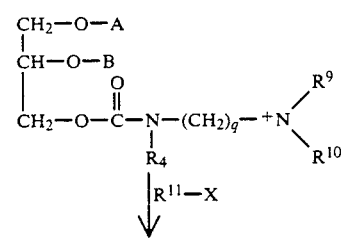 (XVI)

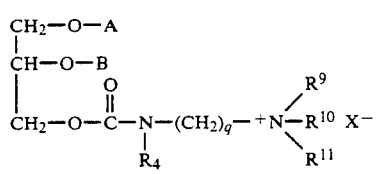 (XVII)

(In the above formula, the definitions of A, B, R⁴, q, R⁹, R¹⁰, R¹¹ and X are the same as those given previously.)

(2) In the case Y is the group indicated with the formula

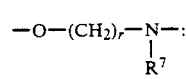

-continued

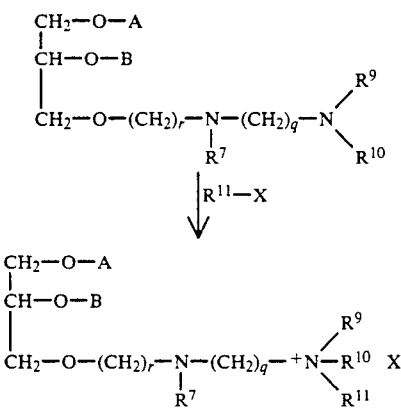

(In the formula, the definitions of A, B, $R^7$, q, $R^9$, $R^{10}$, $R^{11}$ and X are the same as those given previously.)

(3) In the case Y is the group indicated by the formula —U—:

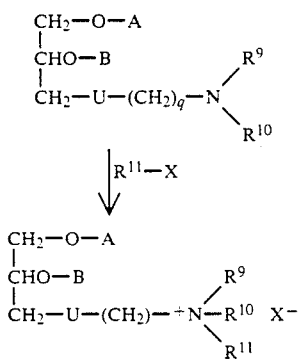

(In the previous formula, the definitions of A, B, U, q, $R^9$, $R^{10}$, $R^{11}$ and X are the same as those given previously.)

(QUATERNARY SALT FORMATION)

This process involves the conversion to a quaternary salt using routine methods of the compounds expressed with general formulae (X), (XII), (XIV), (XVI), (XVIII) and (XX) which were obtained in the processes described previously to obtain the respective compounds of this invention, namely (XI), (XIII), (XV), (XVII), (XIX) and (XXI). In other words, the compounds of this invention which are the target substances, namely (XI), (XIII), (XV), (XVII), (XIX) and (XXI), are easily obtained by reacting the compounds expressed with the general formulae (X), (XII), (XIV), (XVI), (XVIII) and (XX) with the compound expressed with the general formula $R^8$—X (in the formula, the definitions of $R^8$ and X are the same as those given previously) or the compound expressed with the general formula $R^{11}$—X (in the formula, the definitions of $R^{11}$ and X are the same as those given previously.) When forming into hydrohalogen salts, $R^8$—Hal or $R^{11}$—Hal are reacted.

The reaction is conducted in nitrogen gas, without light, without a solvent or with a chlorinated hydrocarbon solvent such as dichloromethane and chloroform or an aromatic solvent such as benzene and toluene.

The reaction temperature is suitably selected within a range from that of ice water to the boiling point of the solvent.

In addition, the compound indicated by general formula (II) which is used for the starting substance in these manufacturing methods can be manufactured according to, for example, the methods indicated below.

The compound expressed with general formula (II) which is used as the starting substance in Manufacturing Method 1 can be obtained according to, for example, the detailed manufacturing method indicated below.

(1) In the case D in formula (I') is the formula

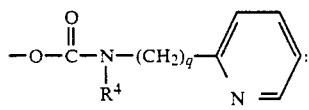

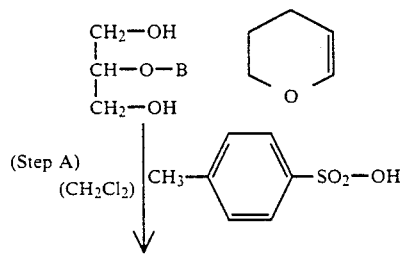

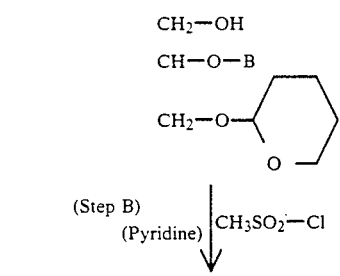

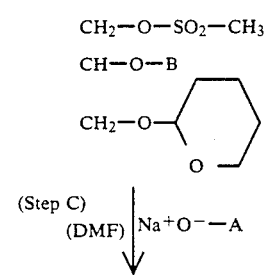

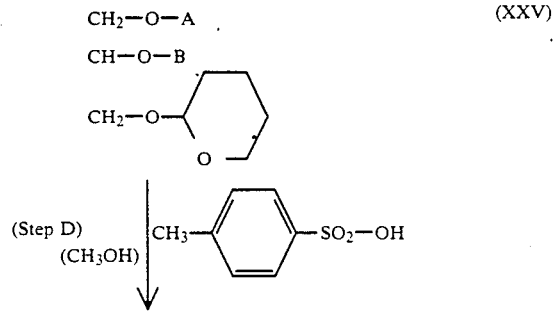

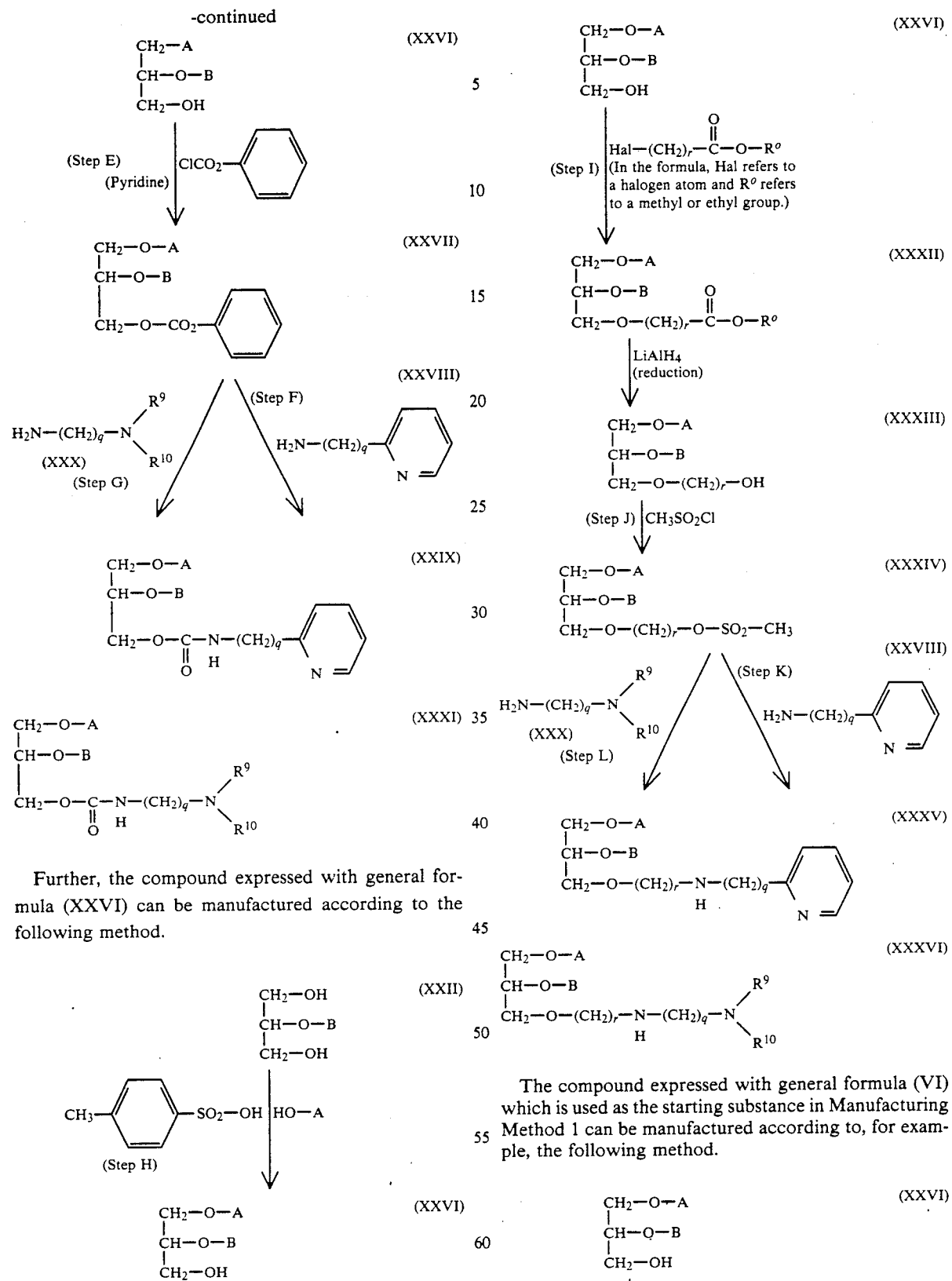

Further, the compound expressed with general formula (XXVI) can be manufactured according to the following method.

The starting substance (IV) used in Manufacturing Method 1 is manufactured according to, for example, the following type of manufacturing method.

The compound expressed with general formula (VI) which is used as the starting substance in Manufacturing Method 1 can be manufactured according to, for example, the following method.

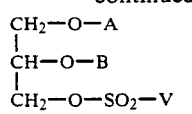

(In the formula, the definitions of A, B and V are the same as those given previously.)

The following is a brief explanation of each of the steps used at the time of manufacturing of the starting substances described previously.

Step A

The compound expressed with general formula (XXIII) can be obtained by reacting the compound expressed with general formula (XXII) and dihydropyran in the presence of acid.

Examples of the acid that is used include p-toluene sulfonic acid and pyridinium p-toluene sulfonic acid.

This reaction is normally conducted in a carbon chloride-based solvent such as dichloromethane or chloroform, ether such as tetrahydrofuran or diethyl ether, benzene-based solvent such as benzene or toluene, or a solvent such as hexane.

The reaction temperature is suitably selected within a range from that of ice water to the boiling point of the solvent.

Step B

The compound expressed with general formula (XXIV) can be obtained by reacting the compound expressed with general formula (XXIII) with methane sulfonyl chloride in the presence of base.

Examples of the base that is used include pyridine and triethylamine.

The reaction is normally conducted in a carbon chloride-based solvent such as dichloromethane or chloroform, ether such as tetrahydrofuran or diethyl ether, benzene-based solvent such as benzene or toluene, or a solvent such as hexane.

The reaction temperature is suitably selected within a range from that of ice water to the boiling point of the solvent.

Step C

The compound expressed with the general formula (XXV) can be obtained by reacting the compound expressed with general formula (XXIV) with the alkoxide or phenoxide Na+O−A that is formed by the treatment of alcohol or phenol AOH with base.

Examples of the base that is used include alkaline metal hydrides such as potassium hydride and sodium hydride, alkaline metals such as sodium metal, sodium alkoxides such as sodium methoxide, as well as potassium carbonate or sodium carbonate.

This reaction is conducted in a solvent which is selected from among ethers such as tetrahydrofuran and diethyl ether, as well as dimethyl formamide, dimethyl sulfoxide, or hexamethyl phosphate amide.

The reaction temperature is suitable selected within a range from that of ice water to the boiling point of the solvent.

Step D

The compound expressed with general formula (XXVI) can be obtained by treating the compound expressed with general formula (XXV) with acid.

Examples of the acid that is used include p-toluene sulfonic acid, hydrochloric acid, nitric acid, and trifluoroacetic acid.

This reaction is normally conducted in an alcohol-based solvent such as methanol or ethanol, a carbon chloride-based solvent such as dichloromethane or chloroform, ether such as tetrahydrofuran or diethyl ether, or a mixture of any of the above solvents with water.

The reaction temperature is suitably selected within a range from that of ice water to the boiling point of the solvent.

Step E

The compound expressed with general formula (XXVII) can be obtained by reacting the compound expressed with general formula *XXVI) in the presence of phenyl halogenogic acid and base.

Examples of the base that is used include pyridine and triethylamine.

This reaction is conducted in the absence of a solvent or in a solvent that is selected from among carbon chloride-based solvents such as chloroform and dichloromethane, ethers such as tetrahydrofuran and diethyl ether, benzene-based solvents such as benzene and toluene, acetonitrile, dimethyl formamide, dimethyl sulfoxide or hexamethyl phosphate triamide.

The reaction temperature is suitable selected within a range from −78° C. to the boiling point of the solvent.

Step F

The compound expressed with general formula (XXIX) can be obtained by reacting the compound expressed with general formula (XXVII) with the amine expressed with general formula (XXVIII).

This reaction is conducted in the absence of solvent or in a solvent which is selected from among carbon chloride-based solvents such as chloroform and dichloromethane, ethers such as tetrahydrofuran and diethyl ether, benzene-based solvents such as benzene and toluene, acetonitrile, dimethyl formamide, dimethyl sulfoxide or hexamethyl phosphate triamide.

The reaction temperature is suitable selected within a range from that of ice water to the boiling point of the solvent.

Step G

The compound expressed with general formula (XXXI) can be obtained by reacting the compound expressed with general formula (XX and VII) with the amine expressed with general formula (XXX).

The reaction is conducted in the absence of solvent or in a solvent which is selected from among carbon chloride-based solvents such as chloroform and dichloromethane, ethers such as tetrahydrofuran and diethyl ether, benzene-based solvents such as benzene and toluene, dimethyl sulfoxide, dimethyl formamide or hexamethyl phosphate triamide.

The reaction temperature is suitably selected within a range from below zero to the boiling point of the solvent.

Step H

The compound expressed with general formula (XXVI) can be obtained by reacting the compound expressed with general formula (XXII) with an alcohol HO-A in the presence of acid in a solvent.

Examples of the acid that can be used include p-toluene sulfonic acid and pyridinium p-toluene sulfonic acid.

Examples of the solvent which can be used in this reaction include a carbon chloride-based solvent such as chloroform or dichloromethane or a benzene-based solvent such as toluene or benzene.

The reaction temperature is suitably selected within a range from room temperature to the boiling point of the solvent.

Step I

The compound expressed with general formula (XXXII) can be obtained by reacting the compound expressed with general formula (XXVI) with halogenated ester in the presence of base.

Examples of the base that is used include alkaline metal hydrides such as potassium hydride and sodium hydride, alkaline metals such as sodium metal or sodium alkoxides such as sodium methoxide.

The reaction is conducted in a solvent selected from among ethers such as tetrahydrofuran and diethyl ether, dimethyl formamide, dimethyl sulfoxide, or hexamethyl phosphate triamide.

The reaction temperature is suitably selected within a range from that of ice water to the boiling point of the solvent.

Step J

The compound expressed with general formula (XXXIV) can be obtained by reacting the compound expressed with general formula (XXXIII) with methane sulfonyl chloride in the presence of base.

Examples of the base that is used include pyridine, triethylamine, potassium carbonate and sodium carbonate.

This reaction is normally conducted in a solvent which is selected from among carbon chloride-based solvents such as dichloromethane and chloroform, ethers such as tetrahydrofuran and diethyl ether, benzene-based solvents such as benzene and toluene, or solvents such as hexane.

The reaction temperature is suitably selected within a range from below zero to the boiling point of the solvent.

Step K

The compound expressed with general formula (XXXV) can be obtained by reacting the compound expressed with general formula (XXXIV) with the anion formed by the treatment of the amine expressed in general formula (XXVIII) with base.

Examples of the base that is used include alkaline metal hydrides such as potassium hydride and sodium hydride, alkaline metals such as sodium metal, sodium alkoxides such as sodium methoxide, potassium carbonate or sodium carbonate.

The reaction is conducted in a solvent which is selected from among ethers such as tetrahydrofuran and diethyl ether, dimethyl formamide, dimethyl sulfoxide or hexamethyl phosphate triamide.

The reaction temperature is suitably selected within a range from that of ice water to the boiling point of the solvent.

Step L

The compound expressed with general formula (XXXVI) can be obtained by reacting the compound expressed with general formula (XXXIV) with the anion formed by treating the amine expressed with general formula (XXX) with base.

Examples of the base that is used include alkaline metal hydrides such as potassium hydride and sodium hydride, alkaline metals such as sodium metal, or sodium alkoxides such as sodium methoxide.

The reaction is conducted in a solvent which is selected from among ethers such as tetrahydrofuran and diethyl ether, dimethyl formamide, dimethyl sulfoxide or hexamethyl phosphate triamide.

The reaction temperature is suitably selected within a range from that of ice water to the boiling point of the solvent.

Step M

The compound expressed with general formula (VI) can be obtained by reacting the compound expressed with general formula (XXVI) with methane sulfonyl chloride or p-toluene sulfonyl chloride in the presence of base.

Examples of the base that is used include pyridine and triethylamine.

This reaction is normally conducted in a solvent such as carbon chloride-based solvents such as dichloromethane and chloroform, ethers such as tetrahydrofuran and diethyl ether, or benzene-based solvents such as benzene and toluene.

The reaction temperature is suitably selected within a range from that of ice water to the boiling point of the solvent.

The invention provides a pharmaceutical composition which comprises a therapeutically effective amount of the glycerin derivative or a pharmacologically acceptable salt thereof as defined above and a pharmacologically acceptable carrier.

The invention moreove provides a method for treating a disease caused by platelet activating factors (PAF), which comprises administering a therapeutically effective amount of the glycerin derivative or a pharmacologically acceptable salt thereof as above to a human being suffering from the disease.

The invention is useful especially to the disease is one against which PAF receptor antagonist is effective, DIC, a shock, an anaphylactic shock or hemoribatic shock or allergic diseases.

The invention Provides the pharmacological use of the compound (I) and (I') of the invention in view of its improved PAF inhibiting effect.

It has been found also that the compounds of the present invention are excellent in both the persistence of the PAF inhibiting effect and the stability of the compounds themselves. Thus the present invention is quite valuable.

Therefore, the compounds of the present invention are effective for the treatment and prevention of all sorts of diseases caused by PAF.

Typical examples of the diseases on which the compounds of the present invention are effective include thrombosis, cerebral apoplexy (cerebral hemorrhage, cerebral thrombosis), myocardial infarction, angina pectoris, human disseminated intravascular coagulation (DIC), thrombophlebitis, glomerulonephritis, anaphylactic shock, hemorrhagic shock and allergic diseases.

The compound of the present invention can be used as an anti-PAF agent orally in the form of powder, granule, capsule or syrup or parenterally in the form of suppository, injection, external preparation or drip infusion. The compound of the present invention is usually preferably administered in the form of injection or drip infusion.

The dose which considerably varies depending on the kind of the disease, degree of the symptoms, age, etc. is about 0.01 to 10 mg/kg/h, preferably 0.03 to 5 mg/kg/h, when the compound is administered in the form of drip infusion.

In the intravenous injection of the compound of the invention for the PAF antagonist, the dose may range from 0.001 to 50 mg/kg, preferably from 0.001 to 30 mg/kg, more preferably from 0.001 to .5 mg/kg, most preferably from 0.003 to 3 mg/kg, per an adult per a day. This dose may be administered at once or in portions divided several times a day.

The preparations for the oral or parenteral administration are produced using an ordinary, pharmaceutically acceptable carrier by an ordinary process.

In the production of injection, drip infusion or the like, a pH regulator, buffering agent, stabilizer, solubilizer, etc. are added, if necessary, to the active ingredient, and subcutaneous injection, intramuscular injection, intravenous injection or drip infusion is prepared by an ordinary process wherein the mixture is freeze-dried, if necessary.

PHARMACOLOGICAL TEST AND EXAMPLE OF THE COMPOUND

The invention is supported by the below shown pharmacological tests and the examples of the compounds. Examples 1 to 15 and 25 fall within the scope of the glycerin derivative (I) and Examples 16 to 24 fall within that of (I').

The following experimental examples will further illustrate the effects of the present invention:

EXPERIMENTAL EXAMPLE 1

Effect on the agglutination caused by human PAF

Method

One part by volume of a 3.8% sodium citrate solution was added to 9 parts by volume of blood sampled from the forearm of a healthy male adult to whom had been administered no medicine for at least two weeks. A platelet-rich plasma (PRP) was prepared by centrifugation. The inhibition of the platelet agglutination was determined by an optical method of Born et al. with a Hematolaser II ® (a platelet agglutination meter of Niko Bioscience Co.). PAF was dissolved in Tyrode solution $[Ca^{++}(+)]$ to form a solution having the minimum concentration for causing the maximum agglutination. The test compound was dissolved in a physiological saline.

The agglutination inhibiting activity of the test compound was determined from the rate of inhibition of the maximum light transmittance (maximum agglutination rate) caused by PAF in control PRP. $IC_{50}$ was determined from the inhibition curve. The results are shown in Table 1.

The numeral in the column of the Test compound in Table 1 refers to the Example number of the compound.

Human PAF receptor binding assay

Method

The platelets were sampled from healthy males by an ordinary method and suspended in a binding buffer [10 mM phosphate-buffered saline (pH 7.0) containing 0.1 w/v % of BSA and 0.9 mM of $CaCl_2$] to form a suspension having a concentration of $10^8/460$ $\mu$l. 20 $\mu$l of a solution of the test compound in the binding buffer was placed in a polypropylene tube and then 460 $\mu$l of the platelet suspension was added thereto. The mixture was subjected to a vortex treatment and then incubated at 37° C. for 6 min. 20 $\mu$l of a solution of $^3H$—PAF in the binding buffer (final $^3H$—PAF concentration 0.6 to 1 nM) was added thereto and the mixture was incubated for 6 min. 3 ml of a washing solution (saline containing 0.1 w/v % of BSA) cooled with ice was added thereto to terminate the reaction The reaction mixture was filtered by suction through a glass filter (Whatman GF/C) The glass filter was dried and the radioactivity thereof was determined with a liquid scintillation counter.

The inhibition % was calculated according to the following equation and $IC_{50}$ was determined by interpolation from the FIGURE.

Inhibition % =

$$\frac{(\text{total binding}) - (\text{total binding with compound})}{(\text{total binding}) - (\text{non-specific binding})}$$

wherein:
total binding: dpm obtained when the concentration of the medicine or PAF is 0,
non-specific binding: dpm obtained when $10^{-5}$M of cold PAF was added.

The results are shown in Table 2.

EXPERIMENTAL EXAMPLE 3

Preventive effect against the lethal activity of PAF

Method

A physiological saline or the test compound was given to ICR male mice weighing around 30 g by intravenous injection. After 15 minutes, 100 $\mu$g/kg of PAF was given to them by intravenous injection. Life and death of them were examined after one hour and the survival rate was determined. The results are shown in Table 3.

Results

EXPERIMENTAL EXAMPLE 4

Action on the blood pressure drop induced by RAF

Method

Cannulae were inserted into the carotid and the jugular of each of $F_{344}$ rats anesthetized with Pento (50 mg/kg, i. p.). The blood pressure was determined at the carotid and 0.5 ml/kg of PAF or the test compound was given through the jugular. Three minutes after the injection of 0.5 $\mu$g/kg of PAF, the test compound was given and the antagonism thereof was evaluated. The results are shown in Table 4.

The recovery rate shown in Table 4 is the ratio of the blood pressure rise by the test compound to the drop thereof.

EXPERIMENTAL EXAMPLE 5

Determination of stability in aqueous solution

These compounds were unstable in a neutral or alkaline aqueous solution mainly due to the hydrolysis reaction of the N-acetyl or N-benzoyl group. The relationships between the pH and decomposition rate of several compounds were examined to find that they have the same pattern. The decomposition rate constant under conditions (pH 7.4, 37° C.) where they were relatively easily decomposed was determined and the stabilities of the compounds were compared with one another.

Method of experiment 9 parts by volume of a buffer solution (0.5M sodium phosphate, pH 7.4) was added to 1 part by volume of an aqueous sample solution (1 mg/ml) and the mixture was kept at 37° C. The sampling was conducted at appropriate time intervals and the residual rate of an unreacted compound was determined by reversed phase high-performance liquid chromatography. Since the decomposition rate of most of the compounds can be approximately represented by the first-order decomposition rate equation, the decomposition rate constant was determined by the least squares method. The results are shown in Table 5.

TABLE 1

| Test compound (Ex. No.) | Agglutination inhibiting activity IC$_{50}$ ($\mu$M) |
|---|---|
| 1 | 0.38 |
| 2 | 0.062 |
| 3 | 0.31 |
| 4 | 0.14 |
| 5 | 0.21 |
| 6 | 0.16 |
| 7 | 2.6 |
| 8 | 0.11 |
| 9 | 0.26 |
| 10 | 0.3 |
| 11 | 0.086 |
| 12 | 0.031 |
| 13 | 0.072 |
| 14 | 0.044 |
| 15 | 0.08 |
| 16 | 0.38 |
| 17 | 0.34 |
| 18 | 0.66 |
| 19 | 0.025 |
| 20 | 0.25 |
| 23 | 0.7 |

TABLE 2

| Test compound (Ex. No.) | PAF receptor antagonism IC$_{50}$ ($\mu$M) |
|---|---|
| 2 | 0.0089 |
| 3 | 0.30 |
| 4 | 0.0035 |
| 5 | 0.0019 |
| 6 | 0.00019 |
| 8 | 0.14 |
| 9 | 0.79 |
| 10 | 0.016 |
| 11 | 0.025 |
| 13 | 0.00025 |
| 14 | 0.00019 |
| 15 | 0.00019 |
| 16 | 3.5 |
| 17 | 3.5 |
| 18 | 0.00071 |
| 19 | 0.0022 |
| 20 | 0.0091 |

TABLE 3

| Test compound (Ex. No.) | Dose (mg/kg) | Survival rate | |
|---|---|---|---|
| 15 | 0.03 | 2/7 | 71.4 (%) |
| | 0.1 | 3/7 | 57.1 (%) |
| | 0.3 | 0/7 | 100 (%) |

TABLE 3-continued

| Test compound (Ex. No.) | Dose (mg/kg) | Survival rate | |
|---|---|---|---|
| 13 | 0.03 | 3/7 | 57.1 (%) |
| | 0.1 | 0/7 | 100 (%) |
| | 0.3 | 0/7 | 100 (%) |
| Control | — | 9/12 | 25 (%) |

Note

The survival rate is given by percentage.

The denominator of the fraction is the number of the mice and the numerator is the number of the dead mice.

TABLE 4

| Test compound (Ex. No.) | Dose (mg/kg, i.v.) | Recovery rate (%) |
|---|---|---|
| 1 | 1.0 | 21.7 |
| 2 | 0.1 | 97.4 |
| | 0.01 | 79.2 |
| 6 | 0.01 | 88.5 |
| 8 | 0.1 | 96.7 |
| | 0.01 | 70.1 |
| 10 | 0.1 | 59.6 |
| | 0.01 | 42.5 |
| 13 | 0.01 | 89.7 |
| 14 | 0.01 | 96.8 |
| 15 | 0.01 | 94.6 |
| 16 | 1.0 | 67.8 |
| 17 | 1.0 | 97.5 |
| 18 | 0.01 | 74.1 |
| 19 | 1.0 | 74.9 |
| 20 | 1.0 | 91.1 |

TABLE 5

| Test compound (Ex. No.) | Half-value period of disappearance due to hydrolysis at pH 7.4 at 37° C. (t$_{\frac{1}{2}}$, h) |
|---|---|
| 6 | 28.2 |
| 13 | 21.5 |
| 14 | 26.1 |
| 15 | 24.4 |
| 18 | 37.7 |
| 22 | infinite |
| 23 | 361 |

EXAMPLES

The following typical examples will further illustrate the present invention, which by no means limit the invention.

In the chemical structural formulae in the following examples, Me represents a methyl group, Et an ethyl group and Ph a phenyl group.

EXAMPLE 1

1-Ethyl-2-[N-acetyl-N-{2-methoxy-3-(3,4,5-trimethoxy)phenylcarbamoyloxypropoxy}carbonyl]aminomethylpyridinium iodide

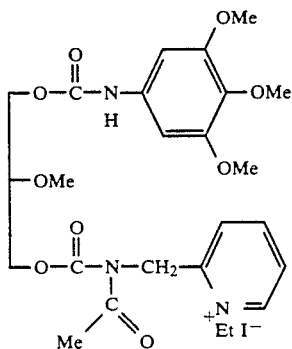

(1) Synthesis of
2-O-methyl-1-O-(3,4,5-trimethoxy)phenylcarbamoylglycerol

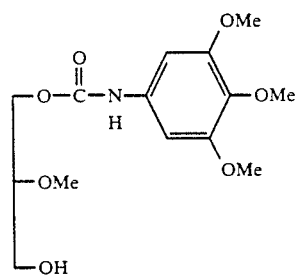

600 ml of a solution of 18.3 g of 3,4,5-trimethoxyaniline in toluene was added to 140 ml of a solution of 48 ml of trichloromethyl chloroformate in toluene and the mixture was refluxed for 3 h. After cooling, the solvent was distilled off and the residue was distilled under reduced pressure (115° C./1 mmHg) to obtain 15.53 g of 3,4,5-trimethoxyphenyl isocyanate.

4.1 g of this product was stirred together with 2.1 g of 2-methoxy-1,3-propanediol and 21 ml of pyridine at room temperature in a nitrogen atmosphere for 44 h. The solvent was distilled off and the residue was dissolved in chloroform, washed with dilute hydrochloric acid solution, water, a saturated aqueous solution of sodium hydrogencarbonate and water successively and then dried over magnesium sulfate. The solvent was removed and the residue was purified according to silica gel column chromatography (eluent: ethyl acetate/n-hexane=1/1) to obtain 2.55 g of the intended product.

$^1$H—NMR (90 MHz, CDCl$_3$)δ; 2.34(m, 1H), 3.36–3.94(m, 3H), 3.50(s, 3H), 3.80(s, 3H), 3.84(s, 6H), 4.32(m, 2H), 6.66(s, 2H), 6.80(m, 1H).

(2) Synthesis of
2-O-methyl-3-O-(2-pyridyl)methylcarbamoyl-1-O-(3,4,5-trimethoxy)phenylcarbamoylglycerol

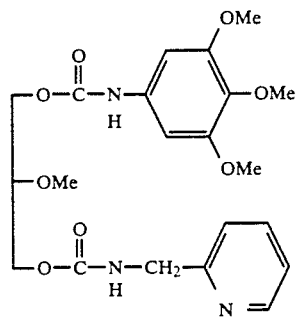

1.10 g of phenyl chloroformate was added dropwise to a mixture of 1.70 g of 2-O-methyl 1-O-(3,4,5-trimethoxy)phenylcarbamoylglycerol prepared in the above-described step (1), 0.95 g of pyridine and 60 ml of methylene chloride under cooling with ice and the obtained mixture was stirred for 30 min. The reaction solution was washed twice with a 1% aqueous sodium hydrogencarbonate solution and then with water and dried over magnesium sulfate. The solvent was distilled off and the obtained oil was dissolved in 80 ml of a solution of 2.38 g of 2-(aminomethyl)pyridine in chloroform and the solution was stirred at 80° C. for 48 h. After cooling, the solvent was distilled off and the residue was purified according to silica gel column chromatography (eluent: ethyl acetate/n-hexane=1/1) to obtain 1.41 g of the intended product.

$^1$H—NMR (90 MHz, CDCl$_3$)δ; 3.49(s, 3H), 3.52–3.92(m, 1H), 3.80(s, 3H), 3.85(s, 6H), 4.26(m, 4H), 4.50(d, J=5 Hz, 2H), 5.76–6.04(m, 1H), 6.67(s, 2H), 6.88(br, S, 1H), 7.06–7.32(m, 2H), 7.46–7.78(m, 1H), 8.52(m, 1H).

(3) Synthesis of
3-O-{N-acetyl-N-(2-pyridyl)methyl}carbamoyl-2-O-methyl-1-O-(3,4,5-trimethoxy)phenylcarbamoylglycerol

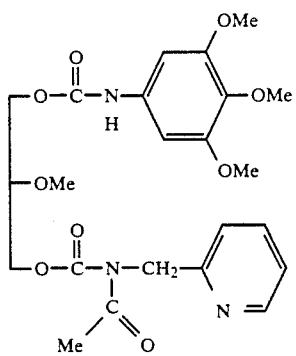

A mixture of 1.30 g of 2-O-methyl-3-O-(2-pyridyl)methylcarbamoyl-1-O-(3,4,5-trimethoxy)phenylcarbamoylglycerol prepared in the above-described step (2), 30 g of acetic anhydride and 30 ml of pyridine was stirred in a nitrogen atmosphere at 110° C. for 15 h. After cooling, the solvent was distilled off and the residue was purified by silica gel column chromatography (eluent: ethyl acetate/n-hexane=1/1) to obtain 0.87 g of the intended product.

¹H—NMR (90 MHz, CDCl₃)δ; 2.62(s, 3H), 3.34(s, 3H), 3.50(m, 1H), 3.81(x, 3H), 3.82(s, 6H), 3.90–4.18(m, 2H), 4.29(d, J=5 Hz, 2H), 5.12(s, 2H), 6.75(s, 2H), 6.98–7.30(m, 2H), 7.48–7.90(m, 2H), 8.36–8.54(m, 1H).

(4) Synthesis of 1-ethyl-2-[N-acetyl-N-{2-methoxy-3-(3,4,5-trimethoxy)phenylcarbamoyloxy}propoxycarbonyl]aminomethylpyridinium iodide

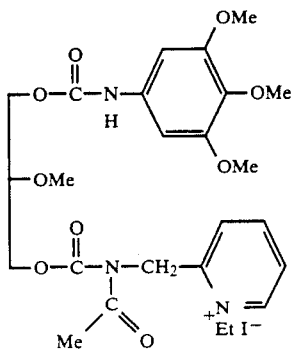

0.67 g of 3-O-{N-acetyl-N-(2-pyridyl)methyl}-carbamoyl-2-O-methyl-1-O-(3,4,5-trimethoxy)phenylcarbamoylglycerol prepared in the above-described step (3) was dissolved in 25 ml of ethyl iodide and the solution was refluxed at 70° C. in a nitrogen atmosphere for 18 h while shielding light. After cooling, precipitates thus formed were recovered and reprecipitated from acetone/ether twice to obtain 0.2 g of the intended product.

¹H—NMR (90 MHz, CDCl₃)δ; 1.65(t, J=8 Hz, 3H), 2.67(s, 3H), 3.43(s, 3H, 3.62–3.88(m, 1H), 3.80(s, 3H), 3.84 (s, 6H), 4.10(m, 2H), 4.52(m, 2H), 4.96 (m, 2H), 5.45(s, 2H), 6.89(s, 2H), 7.72–7.97(m, 3H), 8.28–8.52(m, 1H), 9.07–9.22(m, 1H).

EXAMPLE 2

1-Ethyl-2-[N-{3-(2-fluoreneamino)carbonyloxy-2-methoxypropyloxy}carbonyl-N-(2-methoxy)benzoyl-]aminomethylpyridinium chloride

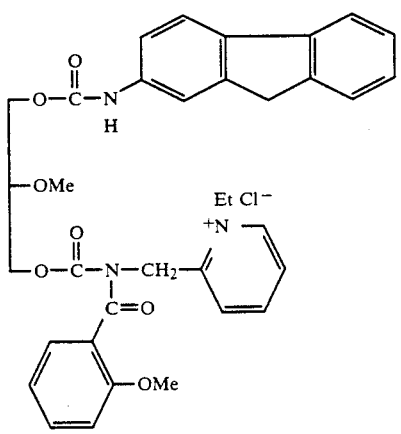

(1) Synthesis of 2-O-methyl-3-O-{N-(2-pyridyl)methyl}carbamoyl-1-O-(tetrahydro-2H-pyran-2-yl)glycerol

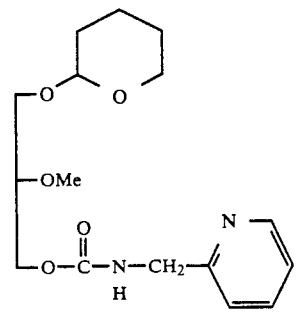

1-O-(Tetrahydro-2H-pyran-2-yl)-2-O-methylglycerol was dissolved in 250 ml of pyridine. Phenyl chloroformate was added dropwise to the solution under stirring and under cooling with ice. After two hours, the mixture was thrown into dilute hydrochloric acid and extracted with 300 ml of ether. The organic layer was washed with a saturated aqueous solution of sodium hydrogencarbonate, dried over anhydrous magnesium sulfate and concentrated under reduced pressure. 60 ml of 2-aminomethylpyridine was added to the residue and the reaction was conducted at room temperature for 1 h. By the purification according to silica gel column chromatography (eluent: ethyl acetate/n-hexane=1/1), 46 g of the intended product was obtained.

¹H—NMR (90 MHz, CDCl₃)δ; 1.30–2.00(m, 6H), 3.26–3.94(m, 5H), 3.40(s, 3H), 4.04–4.26(m, 2H), 4.40(d, J=6 Hz, 2H), 4.55(m, 1H), 5.96(m, 1H), 6.96–7.40(m, 2H), 7.55(m, 1H), 8.42(m, 1H).

(2) Synthesis of 2-O-methyl-3O-[N-(2-pyridyl)methyl]carbamoylglycerol

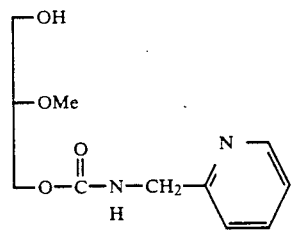

2-O-Methyl-3-O-{N-(2-pyridyl)methyl}carbamoyl-1-O-(tetrahydro-2H-pyran-2-yl)glycerol prepared in the above-described step (1) was dissolved in 200 ml of methanol. 30 g of p-toluenesulfonic acid was added to the solution and the reaction was conducted for 5 h. The reaction solution was concentrated to a volume of 100 ml, added to 200 ml of a saturated aqueous solution of sodium hydrogencarbonate, and extracted with ethyl acetate three times. The organic layers were combined and concentrated under reduced pressure. The aqueous layer was also concentrated under reduced pressure and ethyl acetate was added to the residue. The mixture was filtered and the filtrate was concentrated under reduced pressure. Both the residues were combined together and purified by silica gel column chromatography eluent: methanol/ethyl acetate=5/95) to obtain 27 g of the intended product.

$^1$H—NMR (90 MHz, CDCl$_3$)δ; 3.13(br, 1H) 3.28–3.80(m, 3H), 3.42(s, 3H), 4.20(d, J=5.4 Hz, 2H), 4.43(d, J=5.6 Hz, 2H), 6.16(br, 1H), 7.00–7.30(m, 2H) 7.60(m, 1H), 8.44(m, 1H).

(3) Synthesis of 1-O-(2-fluoreneamino)carbonyl-2-O-methyl-3-O-{N-(2-pyridyl)methyl}carbamoylglycerol

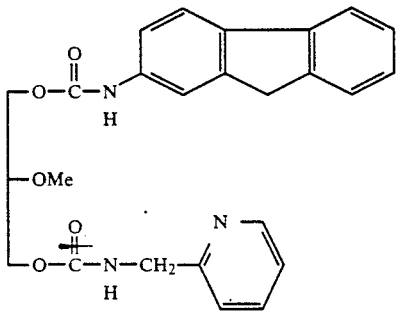

5.7 g (31.2 mmol) of 2-aminofluorene was suspended in 100 ml of toluene. 12.5 g (62.9 mmol) of TCF (trichloromethyl chloroformate) was added to the suspension and the mixture was heated under reflux for 30 min.

Toluene and excess TCF were distilled off. A solution of 5 g (20.8 mmol) of the alcohol prepared in the above-described step (2) in tetrahydrofuran and then 20 ml of pyridine were added to the reaction mixture. The mixture was stirred at room temperature for 1 h and then heated at 50° C. in an oil bath for 30 min. After cooling, 200 ml of ice/water and 100 ml of methylene chloride were added to the reaction solution and an insoluble matter was removed by filtering by suction. The organic layer was washed with water, concentrated and purified by silica gel column chromatography (eluent: methylene chloride/acetone =1/1) to obtain 5.3 g of the intended product.

$^1$H—NMR (90 MHz, CDCl$_3$)δ; 3.46(s, 3H), 3.64(m, 1H), 3.83(s, 2H), 4.00–4.36(m, 4H), 4.46(d, J=5.5 Hz, 2H), 6.98 (br. 1H), 7.00–7.80(m, 11H), 8.46(m, 1H).

(4) Synthesis of 1-O -(2-fluoreneamino)-3-O-{N-(2-methoxy)benzoyl-N-(2-pyridyl)methyl}carbamoyl-2-O-methylglycerol

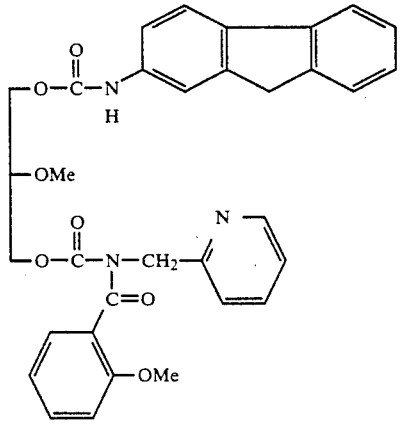

1-O-(2-Fluoreneamino)carbonyl-2-O-methyl-3-O-{N-(2-pyridyl)methyl}carbamoylglycerol prepared in the above-described step (3) was added to 51 ml of pyridine. 2-Methoxybenzoyl chloride was added dropwise to the mixture under stirring at room temperature to conduct the reaction for 1.5 h. The reaction solution was added to 50 ml of a saturated aqueous solution of sodium hydrogencarbonate and extracted with methylene chloride three times. The organic layers were combined, dried over anhydrous magnesium sulfate and concentrated under reduced pressure. The residue was purified according to silica gel column chromatography (eluent: ethyl acetate/n-hexane=2/1) to obtain 7 g of the intended product.

$^1$H—NMR (90 MHz, CDCl$_3$)δ; 1.70(br, 1H), 3.07(s, 3H), 3.10(m, 1H), 3.85(s, 3H), 3.88(bs, 2H), 3.96(m, 2H), 4.13(m, 2H), 5.29(s, 2H), 6.85–7.85(m, 14H), 8.58(m, 1H).

(5) Synthesis of 1-ethyl-2-[N-{3-(2-fluoreneamino)carbonyloxy-2-methoxypropyloxy}carbonyl-N-(2-methoxy)benzoyl-]aminomethylpyridinium chloride

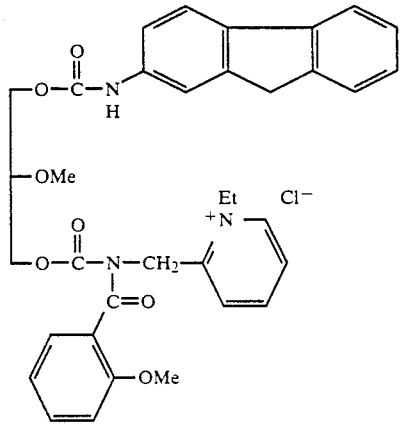

1-O-(2-Fluoreneamino)-3-O-{N-(2-methoxy)benzoil-N-(2-pyridyl)methyl}carbamoyl-2-O-methylglycerol prepared in the above-described step (4) was dissolved in 70 ml of ethyl iodide and the solution was heated under reflux for 24 h. The reaction solution was cooled to room temperature and cencentrated to dryness. The residue was treated with an ion exchange resin [Amberlite IRA-410 of Cl$^-$ type] (eluent methanol/water =7/3) to obtain 8.5 g of the crude chloride. It was purified by silica gel column chromatography (eluent: methanol/methylene chloride=5/95) to obtain 7.1 g of the intended product.

$^1$H—NMR (400 MHz, CDCl$_3$)δ; 1.58(t, J=7 Hz, 3H), 3.15(s, 3H), 3.30(bs, 2H), 3.31(m, 1H), 3.89(s, 3H), 3.91(dd, J =12 Hz, 5 Hz, 1H), 4.07(m, 1H), 4.20(m, 1H), 4.77(q, J=7 Hz, 2H), 5.55(bs, 2H), 7.07(t, J=7 Hz, 1H), 7.13(d, J=8 Hz, 1H, 7.26(t, J=7 Hz, 1H), 7.35(t, J=8 Hz, 1H), 7.42–7.55(m, 4H), 7.71(bs, 1H), 7.79(m, 2H), 8.02(d, J=8 Hz, 1H), 8.10(t, J=6Hz, 1H), 8.67(t, J=8 Hz, 1H), 9.16(d, J=6 Hz, 1H), 9.80(bs, 1H) MS FAB:610(M$^-$).

EXAMPLE 3

1-Ethyl-2-[N-(2-methoxy)benzoyl-N-{2-methoxy-3-(2-tetrahydrofuranyl)methyl}carbamoyloxypropoxycarbonyl]aminomethylpyridinium chloride

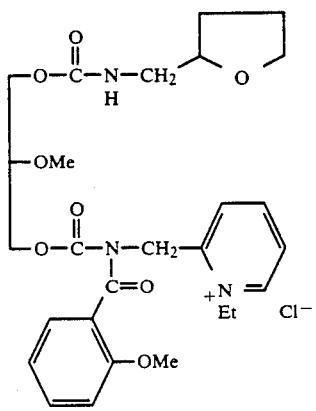

(1) Synthesis of 1,3-O-diphenyloxycarbonyl-2-O-methylglycerol

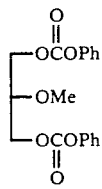

20 g of 2-methoxy-1,3-propanediol was dissolved in 200 ml of pyridine. 52.6 ml of phenyl chlorocarbonate was added dropwise to the solution under stirring and under cooling with ice. After two hours, the reaction solution was added to 1 l of 4N hydrochloric acid/water. After extraction with ether, the organic layer was washed with a saturated aqueous solution of sodium hydrogencarbonate, concentrated and purified according to silica gel column chromatography (eluent: n-hexane/ethyl acetate=1/1) to obtain 52 g of the intended product.

$^1$H—NMR (90 MHz, CDCl$_3$)δ; 3.52(s, 3H, 3.76(m, 1H), 4.34(m, 2H), 4.40 (m, 2H), 7.00–7.50(m, 10H).

(2) Synthesis of 2-O-methyl-1-O-phenoxycarbonyl-3-O-{N-(2-pyridyl)methyl}carbamoylglycerol

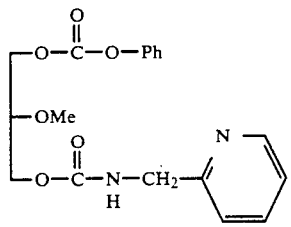

50 g of 1,3-O-diphenyloxycarbonyl-2-O-methylglycerol prepared in the above-described step (1) was dissolved in 50 ml of chloroform. 14.9 ml of 2-(aminomethyl)pyridine was added dropwise to the solution under stirring at room temperature. The reaction solution was heated under reflux for 7 h and concentrated. The concentrate was purified by silica gel column chromatography (eluent: n-hexane/ethyl acetate=1/1) to obtain 29 g of the intended product.

$^1$H—NMR 90 MHz, CDCl$_3$)δ; 3.53(s, 3H), 3.76(m, 1H), 4.20–4.42(m, 4H), 4.51(d, J=5 Hz, 2H), 5.92(br, 1H), 7.16–7.56(m, 7H), 7.70(m, 1H), 8.56(m, 1H).

(3) Synthesis of 3-O-{N-(2-methoxy)benzoyl-N-(2-pyridyl)methyl}carbamoyl-2-O-methyl-1-O-phenoxycarbonylglycerol

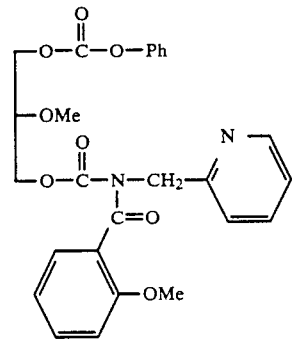

16 g of 2-O-methyl-1-O-phenoxycarbonyl-3-O-{N-(2-pyridyl)methyl}carbamoylglycerol prepared in the above-described step (2) was dissolved in 160 ml of pyridine. 2-Methoxybenzoyl chloride was added dropwise to the solution at room temperature. The mixture was stirred for 1 h. A cold saturated aqueous solution of sodium hydrogencarbonate was added thereto. After extraction with methylene chloride, the organic layer was washed with water and concentrated. The concentrate was purified by silica gel column chromatography (eluent: n-hexane/ethyl acetate=2/1) to obtain 21 g of the intended product.

$^1$H—NMR (90 MHz, CDCl$_3$)δ; 3.24(s, 3H), 3.30(m, 1H), 3.82(s, 3H), 3.70–4.10(m, 4H), 5.20(s, 2H), 6.70–7.50(m, 11H), 7.60(m, 1H), 8.48(m, 1H).

(4) Synthesis of 3-O-{N-(2-methoxy)benzoyl-N-(2-pyridyl)methyl}carbamoyl-2-O-methyl-1-O-(2-tetrahydrofuranyl)methylcarbamoylglycerol

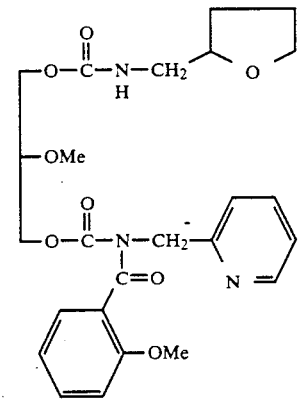

A mixture of 1 g of 3-O-{N-(2-methoxy)benzoyl-N-(2-pyridyl)methyl}carbamoyl-2-O-methyl-1-O-phenoxycarbonylglycerol prepared in the above-described step (3). 0.35 g of tetrahydrofurfurylamine and 30 ml of chloroform was refluxed for 12 h. After cooling, the solvent was distilled off and the residue was purified by silica gel column chromatography (eluent: ethyl acetate/n-hexane=1/1) to obtain 0.40 g of the intended product.

¹H—NMR (90 MHz, CDCl₃)δ; 1.70–2.08(m, 4H), 2.84–4.22(m, 10H), 3.17(s, 3H), 3.82(s, 3H), 4.84–5.28(br, 1H), 5.18(s, 2H), 6.76–7.72(m, 7H), 8.48 (m, 1H).

(5) Synthesis of -ethyl-2-[N-(2-methoxy)benzoyl-N-{2-methoxy-3-(2-tetrahydrofuranylmethyl}carbamoyloxypropoxycarbonyl]aminomethylpyridinium chloride

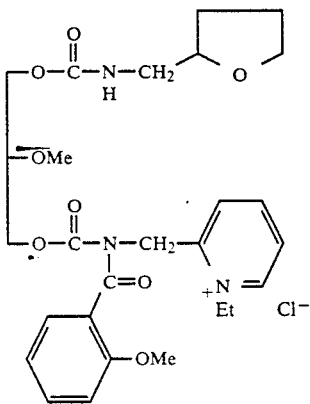

0.4 g of 3-O-{N-(2-methoxy)benzoyl-N-(2-pyridyl)methyl}carbamoyl-2-O-methyl-1-O-(2-tetrahydrofuranyl)methylcarbamoylglycerol prepared in the above-described step (4) was dissolved in 40 ml of ethyl iodide. The solution was refluxed in a nitrogen atmosphere for 24 h while shielding light. After cooling, the solvent was distilled off and the residue was treated with an ion exchange resin [Amberlite IRA-410, Cl⁻ type] (eluent: methanol/water=7/3) and then purified by silica gel column chromatography (eluent: methanol/methylene chloride=1/9) to obtain 0.3 g of the intended product.

¹H—NMR (90 MHz, CDCl₃)δ; 1.28–2.12(m, 7H), 2.64–4.28(m, 10H), 3.18(s, 3H), 3.88(s, 3H), 4.92–5.28(m, 2H), 5.30–5.70(m, 1H), 5.49(s, 2H), 6.76–7.08(m, 2H), 7.25–7.55(m, 2H), 7.80–8.20(m, 2H), 8.30–8.56(m, 1H), 9.88(m, 1H).

EXAMPLE 4

1-Ethyl-2-[N-(2-methoxy)benzoyl-N-(2-methoxy-3-(3-octadecyloxy)propylcarbamoyloxy}propoxycarbonyl-]aminomethylpyridinium chloride

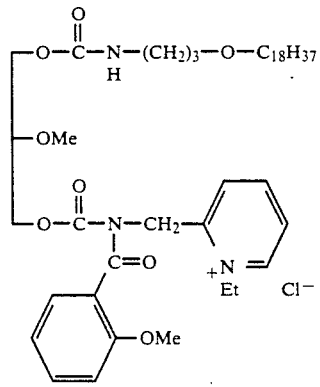

(1) Synthesis of 2-O-methyl-1-O-(3-octadecyloxy)propylcarbamoyl-3-O-(2-pyridyl)methylcarbamoylglycerol

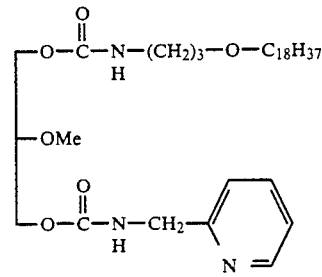

2.86 g of 2-O-methyl-1-O-phenoxycarbonyl-3-O-{N-(2-pyridyl)methyl}carbamoylglycerol prepared in Example 3(2) and 2.6 g of 3-(octadecyloxy)propylamine were dissolved in chloroform to form a homogeneous solution. Then the solvent was distilled off and the residue was stirred at 100° C. overnight. After cooling followed by purification by silica gel chromatography (eluent: ethyl acetate/n-hexane=1/1), 1 g of the intended product was obtained.

¹H—NMR (90 MHz, CDCl₃)δ; 0.87(m, 3H), 1.00–1.86(m, 34H), 3.00–3.74(m, 6H), 3.39(s, 3H), 3.90–4.29(m, 5H), 4.45(d, J=5 Hz, 2H), 4.98–5.26(br, 1H), 5.70–5.96(br, 1H), 6.98–7.28(m, 2H), 7.44–7.70(m, 1H), 8.34–8.52(m, 1H).

(2) Synthesis of 3-O-{N-(2-methoxy)benzoyl-N-(2-pyridyl)methyl}carbamoyl-2-O-methyl-1-O-(3-octadecyloxy)propylcarbamoylglycerol

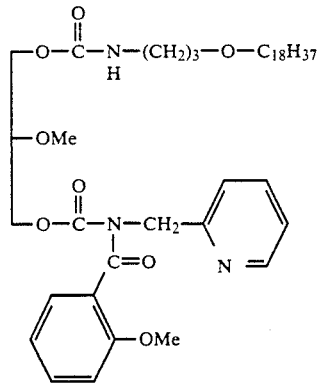

1.0 g of 2-O-methyl-1-O-(3-octadecyloxy)propylcarbamoyl-3-O-(2-pyridyl)methylcarbamoylglycerol prepared in the above-described step (1) was dissolved in 20 ml of tetrahydrofuran. 0.2 g of potassium hydride was added to the solution at room temperature and the mixture was stirred for 30 min. 0.29 g of 2-methoxybenzoyl chloride was added thereto under cooling with ice and the mixture was stirred for 1 h. 0.2 g of acetic acid was added to the reaction solution and the mixture was stirred at room temperature for 30 min. Ethyl acetate was added thereto and the mixture was washed with a saturated aqueous solution of sodium hydrogencarbonate twice and then with water twice and dried over anhydrous magnesium sulfate. The solvent was distilled off and the residue was purified by silica gel column chromatography (eluent: ethyl acetate/n-hexane=1/1) to obtain 0.25 g of the intended product.

$^1$H—NMR (90 MHz, CDCl$_3$)δ; 0.88(m, 3H), 1.05–1.90(m, 34H), 3.06–3.54(m, 7H), 3.18(s, 3H), 3.70–3.90(m, 2H), 3.81(s, 3H), 3.92–4.22(m, 2H), 5.00–5.26(br, 1H), 5.19(s, 2H), 6.74–7.73(m, 7H), 8.48(m, 1H).

(3) Synthesis of 1-ethyl 2-[N-(2-methoxy)benzoyl-N-{2-methoxy-3-(3-octadecyloxy)propylcarbamoyloxy}propoxycarbonyl-]aminomethylpyridinium chloride

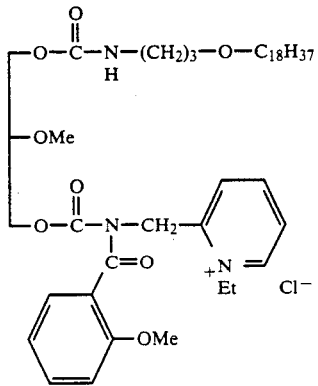

0.25 g of 3-O-[N (2-methoxy)benzoyl-N-(2-pyridyl)-methyl]carbamoyl-2-O-methyl-1-O-(3-octadecyloxy)-propylcarbamoylglycerol prepared in the step (2) was dissolved in 30 ml of ethyl iodide and the solution was refluxed in a nitrogen atmosphere for 48 h while shielding light. After cooling, the solvent was distilled off and the residue was treated with an ion exchange resin [Amberlite IRA-410, Cl$^-$ type] (eluent: methanol/water=7/3), purified by silica gel column chromatography (eluent: methanol/methylene chloride=1/9) and freeze-dried to obtain 0.20 g of the intended product.

$^1$H—NMR (90 MHz, CDCl$_3$)δ; 0.89(m, 3H), 1.09–1.97(m, 34H), 1.84(m, 3H), 3.12–3.62(m, 7H), 3.27(s, 3H), 3.73–3.89(m, 2H), 3.97(s, 3H), 4.03–4.41(m, 2H), 5.31(m, 2H), 5.52(m, 1H), 5.62(s, 2H), 6.90–7.25(M, 2H), 7.45–7.69(m, 2H), 8.03–8.30(m, 2H), 8.41–8.62(m, 1H), 10.29 (m, 1H).

EXAMPLE 5

1-Ethyl-2-[N-{3-(10-N,N-dimethylcarbamylamino)-decylcarbamoyloxy-2-methoxypropyloxy}carbonyl-N-(2)methoxy)benzoyl]aminomethylpyridinium chloride

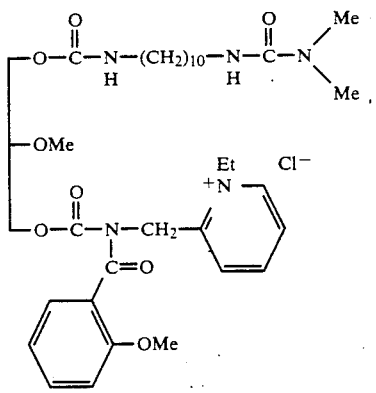

(1) Synthesis of 1-O-(10-N,N-dimethylcarbamylamino)decylcarbamoyl-2-O-methyl-3-O-{N-(2-pyridyl)methyl}carbamoylglycerol

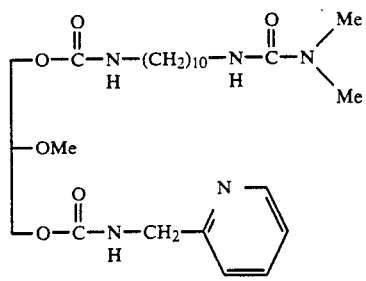

1.5 g of 2-O-methyl-1-O-phenoxycarbonyl-3-O-{N-(2-pyridyl)methyl}carbamoylglycerol prepared in Example 3-(2) was dissolved in 15 ml of chloroform. 1.0 g of 1,10-diaminodecane was added to the solution and the mixture was stirred at 60° C. for 30 min. The reaction solution was left to cool to room temperature. 2 ml of triethylamine and 1.2 ml of N,N-dimethylcarbamyl chloride were added to the solution and the reaction was conducted for 30 min. The reaction solution was added to a saturated aqueous solution of sodium hydrogencarbonate. After extraction with 20 ml of methylene chloride three times, the organic layers were combined, dried over anhydrous magnesium sulfate and concentrated under reduced pressure. The residue was purified by silica gel column chromatography (eluent: methanol/ethyl acetate= 5/95) to obtain 2.0 g of the intended product.

$^1$H—NMR (90 MHz, CDCl$_3$)δ; 1.00–1.72(m, 16H), 2.92(s, 6H), 3.00–3.33(m, 4H), 3.47(s, 3H), 3.64(m, 1H), 4.08–4.29(m, 4H), 4.29–4.50(m, 1H), 4.32(d, J=8 Hz, 2H), 4.92(m, 1H), 6.98(m, 1H), 7.10–7.39(m, 2H), 7.70(t, J=8 Hz, 1H), 8.57 (m, 1H).

(2) Synthesis of 1-O-(N,N-dimethylcarbamylamino)decylcarbamoyl-3-O-{N-(2-methoxy)benzoyl-N-(2-pyridyl)methyl}carbamoyl-2-O-methylglycerol

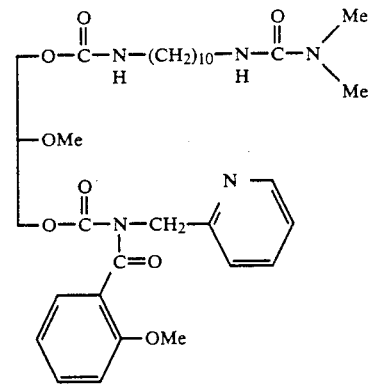

4.2 g of 1-O-(10-N,N-dimethylcarbamylamino)decylcarbamoyl-2-O-methyl-3-O-{N-(2-pyridyl)methyl}carbamoylglycerol prepared in the above-described step (1) was dissolved in 40 ml of pyridine. 1.5 ml of 2-methoxybenzoyl chloride was added to the solution under stirring at room temperature and the reaction was conducted for 30 min. The reaction solution was added to 40 ml of a saturated aqueous solution of sodium hydrogencarbonate. After extraction with 40 ml of methylene chloride three times, the organic layers were combined, dried over anhydrous magnesium sulfate and concentrated under reduced pressure. The residue was purified by silica gel column chromatography (eluent: methanol/ethyl acetate=5/95) to obtain 4.2 g of the intended product.

$^1$H—NMR (90 MHz, CDCl$_3$)δ; 1.04–1.60(m, 16H), 2.80(s, 6H), 2.90–3.05(m, 5H), 3.12(s, 3H), 3.62–3.80(m, 2H), 3.75(s, 3H), 3.87–4.03(m, 2H), 4.20–4.45 (br, 1H), 4.65–4.90(br, 1H), 5.13(s, 2H), 6.70–7.70(m, 7H), 8.43(m, 1H).

(3) Synthesis of 1-ethyl-2-[N-{3-(10-N,N,-dimethylcarbamylamino)-decylcarbamoyloxy-2-methoxypropyloxy}carbonyl-N-(2-methoxy)benzoyl]aminomethylpyridinium chloride

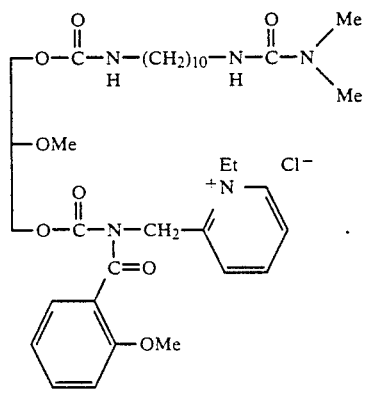

1.2 g of 1-O-(N,N-dimethylcarbamylamino)decylcarbamoyl-3-O-{N-(2-methoxy)benzoyl-N-(2-pyridyl)methyl}carbamoyl-2-O-methylglycerol prepared in the above-described step (2) was dissolved in 20 ml of ethyl iodide and the solution was heated under reflux for two days. The reaction solution was left to cool to room temperature and concentrated under reduced pressure. The residue was treated with an ion exchange resin [Amberlite IRA-410, Cl$^-$ type] (eluent: methanol/water=7/3) to obtain 1.5 g of a crude chloride. This product was purified by silica gel column chromatography (eluent: methanol methylene chloride=5/95) to obtain 1.1 g of the intended product.

$^1$H—NMR (90 MHz, CDCl$_3$)δ; 1.04–1.60(m, 16H), 1.77(t, J=7 Hz, 3H), 2.88(s, 6H), 2.94–3.36(m, 3H), 3.20(s, 3H), 3.52–3.84(m, 4H), 3.90(s, 3H), 3.88–4.26(m, 2H), 4.46(m, 1H), 5.14(q, J =7 Hz, 2H), 5.20(m, 1H), 5.52(br, 2H), 7.00 (m, 2H), 7.44(m, 2H), 8.06(m, 2H), 8.47(m, 1H), 10.1(m, 1H).

EXAMPLE 6

1-Ethyl-2-[N-(2-methoxy)benzoyl-N-{2-methoxy-3-(4-octadecyloxycarbonyl)piperazylcarbonyloxy}propoxycarbonyl]aminomethylpyridinium chloride

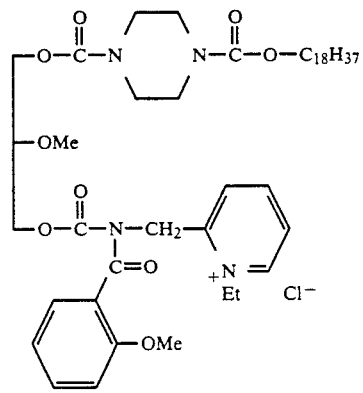

(1) Synthesis of 1-(octadecyloxycarbonyl)piperazine

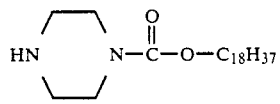

7 g of phenyl chloroformate was added dropwise to a mixture of 10.8 g of 1-octadecanol, 6 g of pyridine and 300 ml of methylene chloride under cooling with ice and the obtained mixture was stirred for 10 min. The reaction solution was washed with a saturated aqueous solution of sodium hydrogencarbonate and then with water and dried over magnesium sulfate. The solvent was distilled off. 13 g of piperazine and 300 ml of tetrahydrofuran were added to the residue to form a homogeneous solution. The solvent was distilled off and the mixture was stirred at 80° C. for 20 min. After cooling, chloroform was added thereto. The obtained mixture was washed with water five times and then dried over magnesium sulfate. The solvent was distilled off to obtain 20.3 g of the intended product.

$^1$H—NMR (90 MHz, CDCl$_3$)δ; 0.88(m, 3H), 1.08–1.75(m, 32H), 2.68–3.02(m, 4H), 3.32–3.77(m, 5H), 4.05(m, 2H).

(2) Synthesis of 2-O-methyl-1-O-(4-octadecyloxycarbonyl)piperazylcarbonyl-3-O-(2-pyridyl)methylcarbamoylglycerol

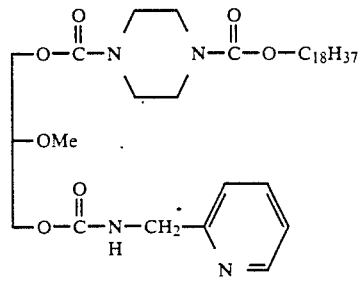

9.5 g of 2-O-methyl-1-O-phenoxycarbonyl-3-O-{N-(2-pyridyl)methyl}carbamoylglycerol prepared in Example 3-(2) and 20 g of 1-(octadecyloxycarbonyl)piperazine prepared in the above-described step (1) were dissolved in methylene chloride to form a homogeneous solution. The solvent was distilled off and the residue was stirred at 100° C. for 3 h. After cooling, the reaction solution was washed with a saturated aqueous solution of sodium hydrogencarbonate and then with water and dried over anhydrous magnesium sulfate. The solvent was distilled off and the residue was purified by silica gel column chromatography (eluent: ethyl acetate/n-hexane=2/1) to obtain 4.61 of the intended product.

$^1$H—NMR (90 MHz, CDCl$_3$)δ; 0.87(m, 3H), 1.08-1.80(m, 32H), 3.18-4.36(m, 7H, 3.40(s, 11H), 4.47(d, J=5 Hz, 2H), 5.80(br, 1H), 6.96-7.32(m, 2H), 7.43-7.72(m, 1H), 8.51(m, 1H).

(3) Synthesis of 3-O-{N-(2-methoxy)benzoyl-N-(2-pyridyl)methyl}carbamoyl-2-O-methyl-1-O-(4-octadecyloxycarbonyl)-piperazylcarbonylglycerol

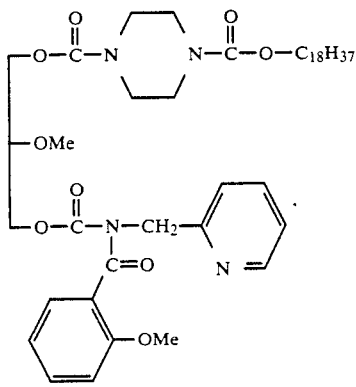

2.4 g of 2-methoxybenzoyl chloride was added to 50 ml of a solution of 4.6 g of 2-O-methyl-1-O-(4-octadecyloxycarbonyl)piperazylcarbonyl-3-O-(2-pyridyl)methylcarbamoylglycerol prepared in the above-described step (2) in pyridine. The mixture was stirred at 90° C. for 1 h. After cooling, the solvent was distilled off and the residue was dissolved in chloroform. The solution was washed with a saturated aqueous solution of sodium hydrogencarbonate and then with water and dried over anhydrous magnesium sulfate. The solvent was distilled off and the residue was purified by silica gel column chromatography (eluent: ethyl acetate/n-hexane=2/1) to obtain 4.6 g of the intended product.

$^1$H—NMR (90 MHz, CDCl$_3$)δ; 0.86(m, 3H), 1.00-1.44(m, 32H), 2.94-3.24(m, 7H), 3.18(s, 3H), 3.37(s, 8H), 3.80(s, 3H), 5.16(s, 2H), 6.70-7.68(m, 7H), 8.46(m, 1H)

(4) Synthesis of 1-ethyl-2-[N-(2-methoxy)benzoyl-N-{2-methoxy-3-(4-octadecyloxycarbonyl)piperazylcarbonyloxy}propoxycarbonyl]aminomethylpyridinium chloride

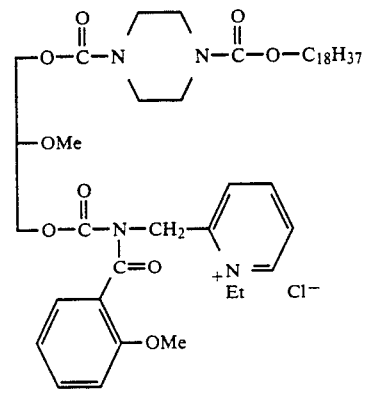

1 g of 3-O-{N-(2-methoxy)benzoyl-N-(2-pyridyl)methyl}carbamoyl-2O-methyl-1-O-(4-octadecyloxycarbonyl)piperazylcarbonylglycerol prepared in the above-described step (3) was dissolved in 30 ml of ethyl iodide and the solution was refluxed in a nitrogen atmosphere for 48 h while shielding light. After cooling, the solvent was distilled off and the residue was treated with an ion exchange resin [Amberlite IRA-410, Cl$^-$ type] (eluent: methanol/water =7/3) and then purified by silica gel column chromatography (elught: methanol/methylene chloride=1/9) to obtain 0.87 g of the intended product.

$^1$H—NMR (90 MHz, CDCl$_3$)δ; 0.86(m, 3H), 1.02-1.63(m, 32H), 1.76(t, d=8 Hz, 3H), 3.00-4.22(m, 7H), 3.20(s, 3H), 3.39(s, 8H), 3.87(s, 3H), 5.18(m, 2H), 5.50(s, 2H), 6.73-7.10(m, 2H), 7.08-7.52(m, 2H), 7.86-8.14(m, 2H), 8.24-8.48(m, 1H), 10.04(m, 1H).

EXAMPLE 7

1-Ethyl-2-[N-{3-(4-ethoxycarbonyl)cyclohexylmethylcarbamoyloxy-2-methoxy}propyloxycarbonyl-N-(2-methoxy)benzoyl]aminomethylpyridinium iodide

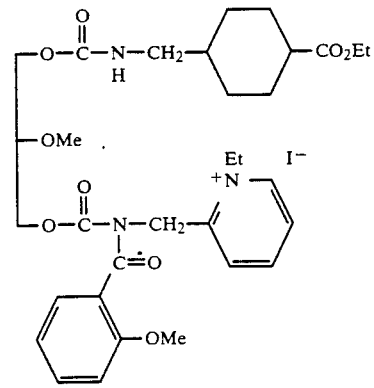

(1) Synthesis of
1-O-(4-ethoxycarbonylcyclohexyl)methylcarbamoyl-3-
O-{N-(2-methoxy)benzoyl-N-(2-pyridyl)methyl}car-
bamoyl-2-O-methylglycerol

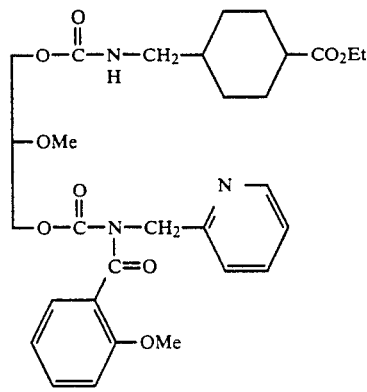

1.0 g of 3-O-{N-(2-methoxy)benzoyl-N-(2-pyridyl)-methyl}carbamoyl-2-O-methyl-1-O-phenoxycarbonyl-glycerol prepared in Example 3-(3) was dissolved in 30 ml of chloroform. 0.5 g of ethyl 4-aminomethylcyclohexanecarboxylate and 0.4 g of triethylamine were added to the solution and the mixture was refluxed for two hours. The reaction solution was washed with a saturated aqueous solution of common salt. Chloroform was distilled off under reduced pressure and the residue was purified by silica gel column chromatography (eluent: ethyl acetate/n-hexane=7.3) to obtain 1.1 g of the intended product.

$^1$H—NMR (90 MHz, CDCl$_3$)δ; 0.64–2.24(m, 10H), 1.25(t, J=8 Hz, 3H), 3.01(t, J=6 Hz, 2H), 3.04–3.28(m, 1H), 3.22(s, 3H), 3.72–4.50(m, 2H), 3.86(s, 3H), 3.96·4.12(m, 2H), 4.11(q, J=8 Hz, 2H), 4.91(m, 1H), 5.25(s, 2H), 6.88–7.80(m, 7H), 8.38(d, J=7 Hz, 1H).

(2) Synthesis of
1-ethyl-2-[N-{3-(4-ethoxycarbonyl)cyclohexylmethyl-carbamoyloxy-2-methoxy}propyloxycarbonyl-N-(2-methoxy)benzoyl]aminomethylpyridinium iodide

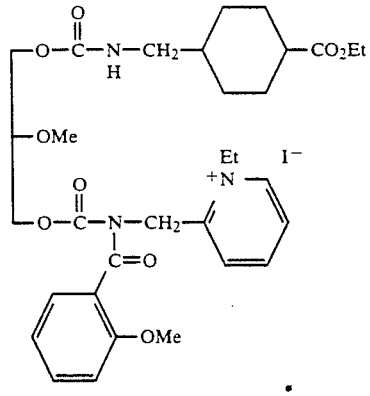

1.1 g of 1-O-(4-ethoxycarbonylcyclohexyl)methyl-carbamoyl-3-O-{N-(2-methoxy)benzoyl-N-(2-pyridyl)-methyl}carbamoyl-2-O-methylglycerol prepared in the above-described step (1) was dissolved in 20 ml of ethyl iodide and the solution was refluxed for 24 h. An insoluble matter was recovered by filtration and dissolved in acetone. Ether was added to the solution to reprecipitate 1.0 g of the intended product.

$^1$H—NMR (90 MHz, CDCl$_3$)δ; 0.64–2.30(m, 10H), 1.24(t, J=8 Hz, 3H), 1.77(t, J=8 Hz, 3H), 2.97(t, J=6 Hz, 2H), 3.08–3.16(m, 1H), 3.20(s, 3H), 3.62–4.24(m, 4H), 3.90(s, 3H), 4.08(q, J=8 Hz, 2H), 4.80–5.20(m, 3H), 5.54(s, 2H), 6.78–7.12(m, 2H), 7.08–7.36(m, 2H), 7.90–8.20(m, 2H), 8.56(t, J=8 Hz, 1H), 9.24(d, J=7 Hz, 1H).

EXAMPLE 8

1-Ethyl-2-[N-(2-methoxy)benzoyl-N-{2-methoxy-3-(2-(4-sulfamoylphenyl)ethylcarbamoyloxy)propyloxy} carbonyl]aminomethylpyridinium iodide

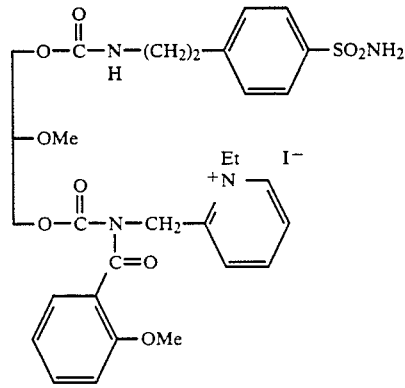

(1) Synthesis of
3-O-{N-(2-methoxy)benzoyl-N-(2-pyridyl)methyl}car-bamoyl-2-O-methyl-1-O-{2-(4-sulfamoyl)phenylethyl} carbamoylglycerol

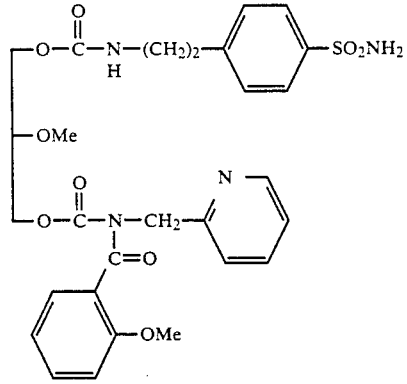

1.0 g of 3-O-{N-(2-methoxy)benzoyl-N-(2-pyridyl)-methyl}carbamoyl-2-O-methyl-1-O-phenoxycarbonyl-glycerol prepared in Example 3-(3) was mixed with 0.5 g of 4-(2-aminoethyl)benzenesulfonamide and the mixture was stirred at 80° C. for 1 h. The reaction mixture was allowed to cool to room temperature and purified by silica gel column chromatography (eluent: chloroform/methanol=95/5) to obtain 0.8 g of the intended product.

$^1$H—NMR (90 MHz, CDCl$_3$)δ; 2.84(t, J=7 Hz, 2H), 3.18(s, 3H), 3.10–3.54(m, 3H), 3.74–3.90(m, 2H), 3.82(s, 3H), 3.92–4.10(m, 2H), 5.08–5.32(m, 3H), 5.57(br, s, 2H), 6.82–7.90(m, 11H), 8.54(d, J=7 Hz, 1H).

(2) Synthesis of 1-ethyl-2-[N-(2-methoxy)benzoyl-N-{2-methoxy-3-(2-(4-sulfamoylphenyl)ethylcarbamoyloxy)propyloxy}carbonyl]aminomethylpyridinium iodide

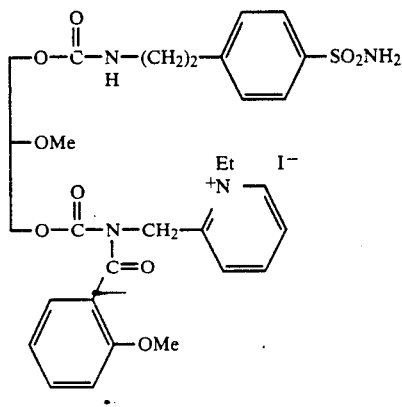

0.8 g of 3-O-{N-(2-methoxy)benzoyl-N-(2-pyridyl)methyl}carbamoyl-2-O-methyl-1-O-{2-(4-sulfamoyl)phenylethyl}carbamoylglycerol prepared in the above-described step (1) was dissolved in 10 ml of ethyl iodide and the solution was refluxed for 24 h. An insoluble matter was recovered by filtration and dissolved in acetone. Ether was added to the solution to reprecipitate 0.7 g of the intended product.

$^1$H—NMR (90 MHz, CDCl$_3$)δ; 1.58(t, J=8 Hz, 3H), 2.60-2.88(m, 2H), 3.04-3.40(m, 3H), 3.33(s, 3H), 3.56-3.76(m, 2H), 3.88(s, 3H), 3.96-4.16(m, 2H), 4.79(q, J=8 Hz, 2H), 5.56(s, 2H), 6.96-7.84(m, 11H), 7.96-7.24(m, 2H), 8.70 (tJ=8 Hz, 1H), 9.18(d, J=7 Hz, 1H).

EXAMPLE 9

1-Ethyl-2-[N-(2-methoxy)benzoyl-N-{3-(3-morpholinocarbonylpropan-1-yl)carbamoyloxy-2-methoxypropyloxy}carbonyl]aminomethylpyridinium chloride

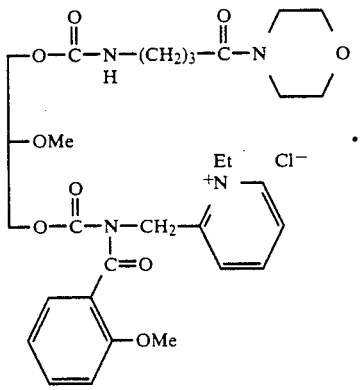

(1) Synthesis of 2-O-methyl-1-O-{3-(morpholinocarbonyl)propyl}carbamoyl-3-O-{N-(2-methoxy)benzoyl-N-(2-pyridyl)methyl}carbamoylglycerol

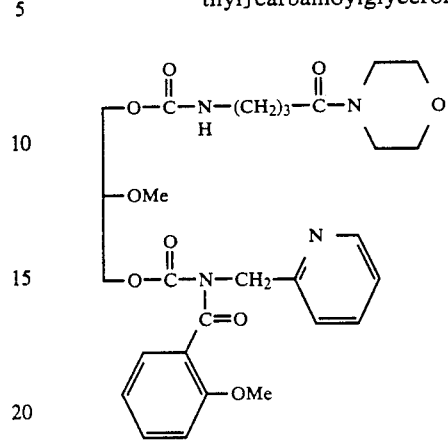

4.7 g of 3-O-{N-(2-methoxy)benzoyl-N-(2-pyridyl)methyl}carbamoyl-2-O-methyl-1-O-phenoxycarbonylglycerol prepared in Example 3-(3) was dissolved in 50 ml of chloroform. 2.4 g of N-(4-aminobutyryl)morpholine was added to the solution and the mixture was refluxed under stirring for 3 h. The solution was concentrated, and the concentrate was purified by silica gel column chromatography (eluent: methylene chloride/methanol=95/5) to obtain 2.9 g of the intended product.

$^1$H—NMR (90 MHz, CDCl$_3$)δ; 1.80(m, 2H), 2.32(t, J=7 Hz, 2H), 3.18(s, 3H), 3.00-3.30(m, 2H), 3.30-3.70(m, 9H), 3.70-4.10(m, 4H), 3.80(s, 3H), 5.12(m, 1H), 5.20(m, 2H), 6.75-7.04(m, 2H), 7.04-7.68(m, 4H), 8.46(m, 1H).

(2) Synthesis of 1ethyl-2-[N-(2-methoxy)benzoyl-N-{3-(3-morpholinocarbonylpropan-1-yl)carbamoyloxy-2-methoxypropyloxy}carbonyl]aminomethylpyridinium chloride

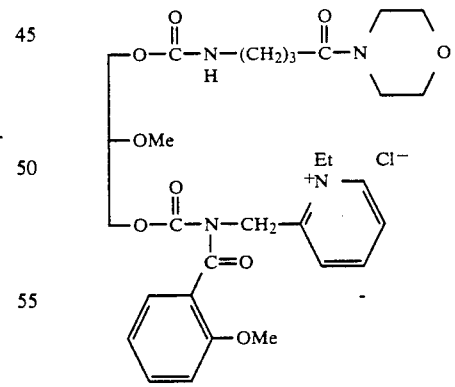

0.9 g of 2-O-methyl-1-O-{3-(morpholinocarbonyl)propyl}carbamoyl-3-O-{N-(2-methoxy)benzoyl-N-(2-pyridyl)methyl}carbamoylglycerol prepared in the above-described step (1) was dissolved in 10 ml of ethyl iodide and the solution was refluxed under stirring in a nitrogen stream for 30 h. After cooling, the reaction solution was concentrated and the residue was treated with an ion exchange resin [Amberlite IRA-410, Cl$^-$ Type] (eluent: methanol/water =7/3) to obtain 0.9 g of a crude chloride. This crude product was purified by silica gel column chromatography (eluent: methylene chloride/methanol =95/5) to obtain 0.9 g of the intended product.

$^1$H—NMR (90 MHz, CDCl$_3$)δ; 1.76(J, J=7 Hz, 3H), 1.82(m, 2H), 3.38(t, J =7 Hz, 2H), 3.20(s, 3H), 3.00–3.30(m, 2H), 3.30–3.70(m, 11H), 3.80–4.30(m, 4H), 5.20(q, J=7 Hz, 2H), 5.52(s, 2H), 5.80(m, 1H), 6.80–7.14(m, 2H), 7.30–7.60(m, 2H), 7.90–8.20(m, 2H), 8.43(m, 1H), 10.63(m, 1H).

EXAMPLE 10

1-Ethyl-2-[N-{3-(6.12-dioxaheptadecyl)carbamoyloxy-2-methoxypropyloxy}carbonyl-N-(2-methoxy)benzoyl-]aminomethylpyridinium iodide

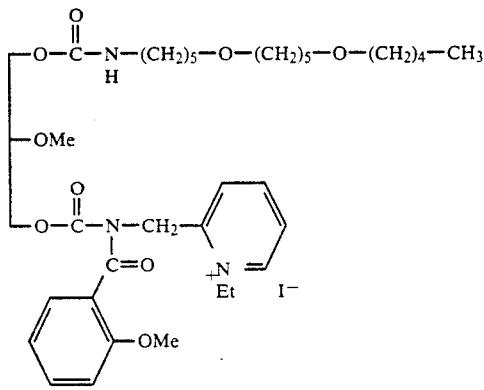

(1) Synthesis of 5-pentyloxy-1-pentanol

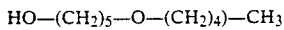

Sodium hydride (60%, 4.2 g) and then 12 ml of 1-bromopentane were added to a solution of 10 g of 1,5-pentanediol in 150 ml of N,N-dimethylformamide. The mixture was stirred at room temperature for 30 min. 3% hydrochloric acid was added to the reaction solution. After extraction with ether, the organic layer was dried and cencentrated. The residue was purified by silica gel column chromatography (eluent: n-hexane/ethyl acetate=8/2) to obtain 6 g of the intended product.

$^1$H—NMR (CDCl$_3$)δ; 0.88(t, J=6 Hz, 3H), 1.00–1.75(m, 12H), 1.90(s, 1H), 3.34(t, J=7 Hz, 4H), 3.58(t, J=6 Hz, 2H).

(2) Synthesis of 6,12-dioxaheptadecanenitrile

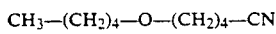

Sodium hydride (60%, 0.75 g) was added to a solution of 3 g of 5-pentyloxy-1-pentanol prepared in the above-described step (1) in 50 ml of N,N-dimetnylformamide. Then 2 ml of 5-bromopentanenitrile was added thereto and the mixture was stirred at 60° C. for 2 h. 3% hydrochloric acid was added to the reaction solution. After extraction with ether, the organic layer was dried and concentrated and the residue was purified by silica gel column chromatography (eluent: n-hexane/ethyl acetate=9/1) to obtain 1 g of the intended product.

$^1$H—NMR (CDCl$_3$)δ; 0.88(T, J=7.2 Hz, 3H), 1.10–2.10(m, 16H), 2.36(t, J=7 Hz, 2H), 3.36(t, J=7.2 Hz, 8H).

(3) Synthesis of 6.12-dioxaheptadecylamine

0.15 g of lithium aluminum hydride was added to a solution of 1 g of 6,12-dioxaheptadecanenitrile prepared in the above-described step (2) in 20 ml of tetrahydrofuran and the mixture was stirred at room temperature for 1.5 h. A saturated aqueous solution of sodium sulfate was added thereto and the obtained mixture was filtered through a Celite filter (eluent: chloroform/methanol=9/1) to obtain 0.3 g of the intended product.

$^1$H—NMR (CDCl$_3$)δ; 0.88(t, J=7 Hz, 3H), 1.10–1.80(m, 18H), 2.68(t, J=7.2 Hz, 2H), 2.92(bs, 2H), 3.34 (t, J=6 Hz, 8H).

(4) Synthesis of 1-O-(6,12-dioxaheptadecyl)carbamoyl-2-O-methyl-3-O-{N-(2-methoxy)benzoyl-N-(2-pyridylmethyl)}carbamoylglycerol

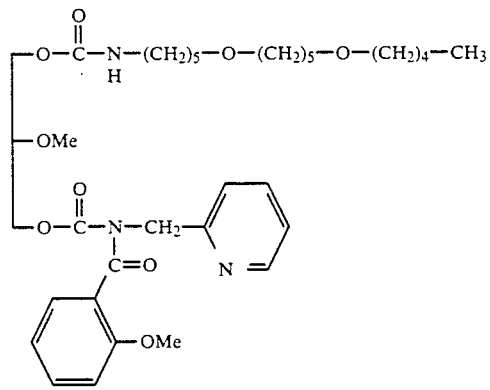

0.28 g of 6,12-dioxaheptadecylamine prepared in the above-described step (3) was added to a solution of 0.53 g of 3-O-{N-(2-methoxy)benzoyl-N-(2-pyridyl)methyl}carbamoyl-2-O-methyl-1-O-phenoxycarbonylglycerol prepared in Example 3-(3) and the mixture was heated under reflux for 4 h. The reaction solution was concentrated and purified by silica gel column chromatography (eluent: benzene/acetone=4/1) to obtain 0.15 g of the intended product.

$^1$H—NMR (CDCl$_3$)δ; 0.85(t, J=6 Hz, 3H), 1.00–1.80(m, 18H), 3.15(s, 3H), 3.14(m, 2H), 3.32(t, J=6 Hz, 8H), 3.75(s, 3H), 3.60–3.85(m, 3H), 3.90–4.05(m, 2H), 4.60–5.00(br, 1H), 5.16(s, 2H), 6.70–7.70(m, 7H), 8.38–8.54(d, J=4 Hz, 1H).

(5) Synthesis of 1-ethyl-2-[N-{3-(6,12-dioxaheptadecyl)carbamoyloxy-2-methoxypropyloxy{carbonyl-N-(2-methoxy)benzoyl-]aminomethylpyridinium iodide

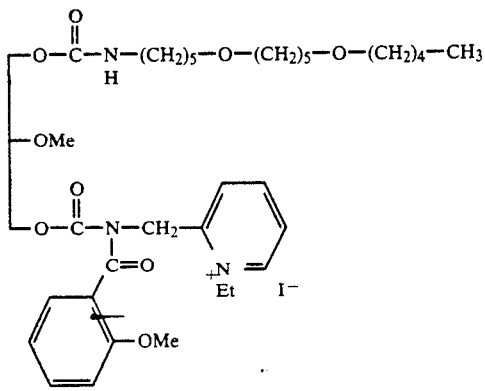

0.15 g of 1-O-(6,12-dioxaheptadecyl)carbamoyl-2-O-methyl-3-O-{N-(2-methoxy)benzoyl-N-(2-pyridylmethyl)}carbamoylglycerol prepared in the above-described step (4) was dissolved in 10 ml of ethyl iodide. The solution was heated under reflux in a nitrogen stream for 48 h while shielding light. The reaction solution was concentrated and the residue was recrystallized from acetone/ether to obtain 0.1 g of the intended product.

$^1$H—NMR (CDCl$_3$)δ; 0.86(t, J=6 Hz, 3H), 1.10–2.00(m, 18H), 1.75(t, J=7.2 Hz, 3H), 3.18(s, 3H), 2.95–3.50(m, 2H), 3.35(t, J=5 Hz, 8H), 3.65–3.80(m, 3H), 3.88(s, 3H), 4.00–4.20(m, 2H), 4.80–5.20(br, 1H), 5.05 (q, J=7.2 Hz, 2H), 5.50(s, 2H), 6.86(d, J=8 Hz, 1H), 7.05(d, J=7.2 Hz, 1H), 7.30–7.52(m, 2H), 7.90–8.20(m, 2H), 8.50(t, J=6 Hz, 1H), 9.65(d, J=6 Hz, 1H).

MS:M/Z 688 (M$^-$-I).

EXAMPLE 11

1-ethyl-2[N-(2-methoxy)benzoyl-N-{2-methoxy-3-(4stearoylpiperazinocarbonyl)oxypropyloxy}carbonyl-]aminomethylpyridinium iodide

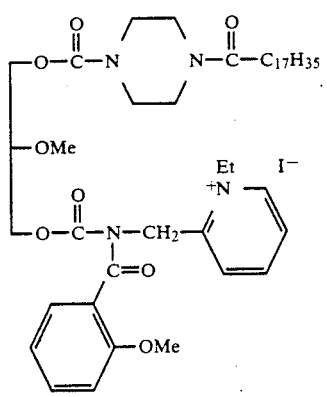

(1) Synthesis of 4-stearoylpiperazine

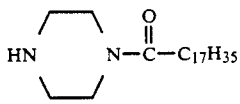

20 g of anhydrous piperazine was dissolved in 1,000 ml of tetrahydrofuran and then 33.6 g of stearoyl chloride was added dropwise thereto under stirring and under cooling with ice. The mixture was stirred under cooling with ice for 1 h and tetrahydrofuran was distilled off under reduced pressure. A saturated aqueous solution of sodium hydrogencarbonate was added to the residue. After extraction with 200 ml of chloroform three times, the extract was washed with a saturated aqueous solution of common salt and the solvent was distilled off under reduced pressure. The residue was purified by silica gel column chromatography (eluent: chloroform/methanol=9/1) to obtain 5.1 g of the intended product.

$^1$H—NMR (90 MHz, CDCl$_3$)δ; 0.84(m, 3H), 1.04–1.80(m, 30H), 2.28(t, J=7 Hz, 2H), 2.52–3.00(m, 4H), 3.36–3.80 (m, 4H), 4.68(br, s, 1H).

(2) Synthesis of 3-O-{N-(2-methoxy)benzoyl-N-(2-pyridyl)methyl}carbamoyl-2-O-methyl-1-O-(4-stearoylpiperazine)carbonylglycerol

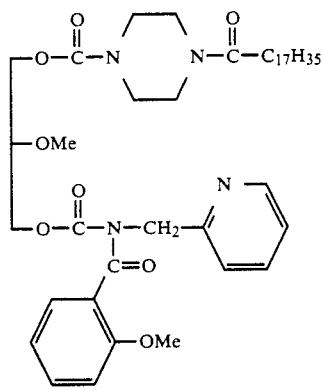

1.0 g of 3-O-{N-(2-methoxy)benzoyl-N-(2-pyridyl)methyl}carbamoyl-2-O-methyl-1-O-phenoxycarbonylglycerol prepared in Example 3-(3) and 1.4 g of 4-stearoylpiperazine prepared in the above-described step (1) dissolved in 10 ml of chloroform. The mixture was stirred at 80° C., chloroform was distilled off and the residue was stirred for additional one hour. The reaction mixture was left to cool to room temperature and purified by silica gel column chromatography (eluent: chloroform/methanol=95/5) to obtain 0.6 g of the intended product.

$^1$H—NMR (90 MHz, CDCl$_3$)δ; 0.90(t, J=7 Hz, 3H), 1.16–1.76(m, 30H), 2.32(t, J=8 Hz, 2H), 3.24(s, 3H), 3.20–3.76 (m, 9H), 3.86(s, 3H), 4.84–5.16(m, 4H), 5.27(s, 2H), 6.88–7.80(m, 7H), 8.58(d, J =6 Hz, 1H).

(3) Synthesis of 1-ethyl-2-[N-(2-methoxy)benzoyl-N-{2-methoxy-3-(4-stearoylpiperazinocarbonyl)oxypropyloxy}carbonyl]aminomethylpyridinium iodide

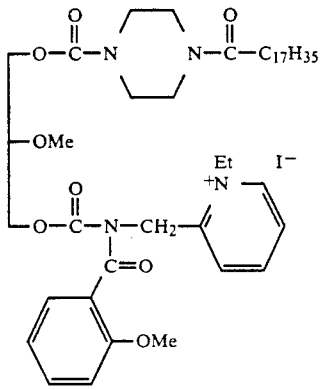

0.6 g of 3-O-{N-(2-methoxy)benzoyl-N-(2-pyridyl)methyl}carbamoyl-2-O-methyl-1-O-(4stearoyl-piperazino)carbonylglycerol prepared in the above-described step (2) was dissolved in 10 ml of ethyl iodide and the solution was refluxed for 24 h. An insoluble matter was recovered by filtration and dissolved in acetone. Ether was added to the solution to form a precipitate. The supernatant liquid was removed to obtain 0.4 g of the intended product.

$^1$H—NMR (90 MHz, CDCl$_3$)δ; 0.88(t, J=6 Hz, 3H), 1.00–1.80(m, 30H), 1.76(t, J=8 Hz, 3H), 2.31(t, J=8 Hz, 2H), 3.22 (s, 3H), 3.10–3.64(m, 9H), 3.90(s, 3H), 3.72–4.20(m, 4H), 5.05(q, J=8 Hz, 2H), 5.55 (s, 2H), 6.72–7.08(m, 2H), 7.24–7.52(m, 2H), 7.88–8.16(m, 2H), 8.55(t, J=8 Hz, 1H), 9.54(d, J=8 Hz, 1H).

EXAMPLE 12

1-Ethyl-2-[N-{3(4-cyclohexylmethylsulfamoyl)benzylcarbamoyloxy-2-methoxypropyloxy}carbonyl-N-(2-methoxy)benzoyl]aminomethylpyridinium chloride

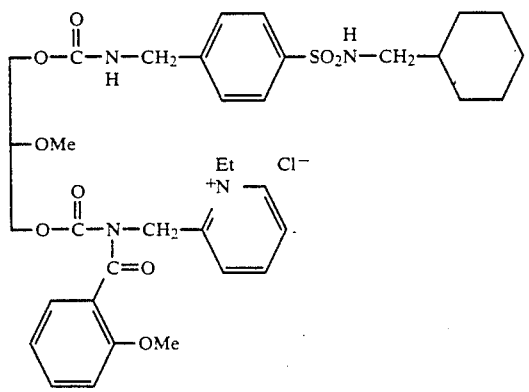

(1) Synthesis of 2-O-methyl-3-O-(2-pyridyl)methylcarbamoyl-1-O-(4-sulfamoyl)benzylcarbamoylglycerol

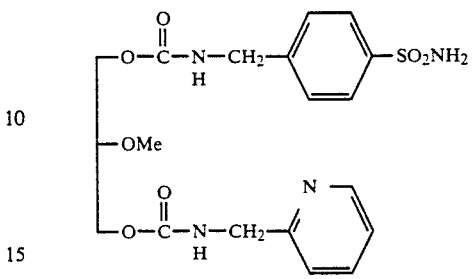

20.0 g of 2-O-methyl-1-O-phenoxycarbonyl-3-O-{N-(2-pyridyl)methyl}carbamoylglycerol prepared in Example 3(2) and 19.0 g of 4-(aminomethyl)benzenesulfonamide hydrochloride hydrate were dissolved in 400 ml of tetrahydrofuran/water (3/1). 17.0 g of triethylamine was added to the solution and the mixture was refluxed for 12 h. Tetrahydrofuran was distilled off under reduced pressure. Water was added to the residue. The mixture was subjected to extraction with 200 ml of ethyl acetate three times. The extract was washed with a saturated aqueous solution of common salt. The solvent was distilled off under reduced pressure and the residue was purified by silica gel column chromatography (eluent: chloroform/methanol=95/5) to obtain 21.0 g of the intended product.

$^1$H—NMR (90 MHz, CDCl$_3$)δ; 3.18(s, 3H), 3.40–3.72(m, 1H), 4.00–4.48(m, 8H), 5.48–6.00(m, 4H), 6.96–7.60(m, 6H), 7.71(d, J=9 Hz, 1H), 8.40(d, J =8 Hz, 1H).

(2) Synthesis of 1-O-(4-cyclohexylmethylsulfamoyl)benzylcarbamoyl-3-O-{N-(2-methoxy)benzoyl-N-(2-pyridyl)methyl}carbamoyl-2-O-methylglycerol

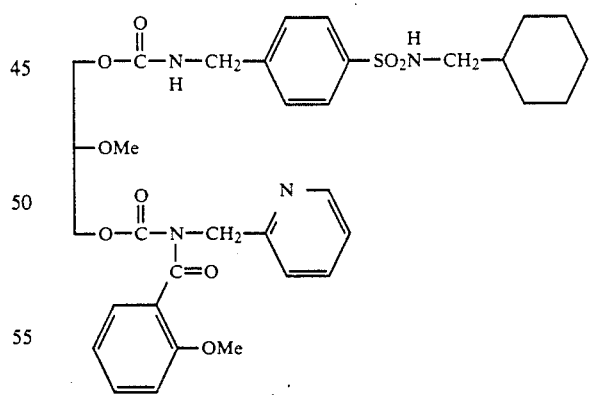

2.0 g of 2-O-methyl-3-O-(2-pyridyl)methylcarbamoyl-1-O-(4-sulfamoyl)benzylcarbamoylglycerol prepared in the above-described step (1), 0.8 g of cyclohexylmethyl bromide and 0.5 g of anhydrous potassium carbonate were dissolved in 50 ml of N,N-dimethylformamide and the solution was stirred at 60° to 70° C. for 2 h. Water was added to the reaction solution, and the aqueous solution was subjected to extraction with 50 ml of ethyl acetate three times. The extract was washed with a saturated aqueous solution of common salt and the solvent was distilled off under reduced pressure. The residue was dissolved in 50 ml of pyridine. 0.86 g of 2-methoxybenzoyl chloride was added dropwise thereto at room temperature and the mixture was stirred at 60° C. for 2 h. Pyridine was distilled off under reduced pressure and the residue was dissolved in ethyl acetate. The organic layer was washed with a saturated aqueous solution of common salt, and the solvent was distilled off under reduced pressure. The residue was purified by silica gel column chromatography (eluent: ethyl acetate/hexane =3/2) to obtain 1.5 g of the intended product.

$^1$H—NMR (90 MHz, CDCl$_3$)δ; 0.60–1.92(m, 11H), 2.72(t, J=6 Hz, 2H), 3.04–3.36(m, 1H), 3.19(s, 3H), 3.80(s, 3H), 3.60–4.20(m, 4H), 4.34(d, J=7 Hz, 2H), 4.52–4.80(m, 1H), 5.15(s, 2H), 5.36–5.60(m, 1H), 6.70–7.64(m, 10H), 7.70(d, J=8 Hz, 1H), 8.41(d, J=7 Hz, 1H).

(3) Synthesis of 1-ethyl-2-{N-3-(4-cyclohexylmethylsulfamoyl)benzyl-carbamoyloxy-2-methoxypropyloxy}carbonyl-N-(2-methoxybenzoyl)aminomethylpyridinium chloride

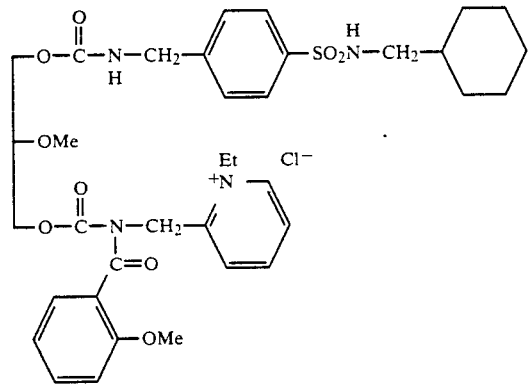

1.5 g of 1-O-(4-cyclohexylmethylsulfamoyl)benzyl-carbamoyl-3-O-{N-(2-methoxy)benzoyl-N-(2-pyridyl)-methyl}-carbamoyl-2-O-methylglycerol prepared in the above-described step (2) was dissolved in 10 ml of ethyl iodide and the solution was refluxed for 24 h. Ethyl iodide was distilled of under reduced pressure and the residue was treated with an ion exchange resin [Amberlite IRA-410, CL$^-$ type ] (eluent: methanol/water =7/3). The solvent was distilled off under reduced pressure and the reside was purified by silica gel column chromatography (eluent: methylene chloride/methanol =9/1) to obtain 1.0 g of the intended product.

$^1$H—NMR (90 MHz, CDCl$_3$)δ; 0.60–1.92(m, 14H), 2.68(t, J=6 Hz, 2H), 3.00–3.40(m, 1H), 3.20(s, 3H), 3.89(s, 3H), 3.60–4.52(m, 6H), 5.08(q, J=8 Hz, 2H), 4.80–5.20(m, 1H), 5.56(s, 2H), 6.20–6.48(m, 1H), 6.80–8.16(m, 10H), 8.44(t, J=8 Hz, 1H), 9.70(d, J=7 Hz, 1H).

EXAMPLE 13

1-Ethyl-2-[N-(2-methoxy)benzoyl-N-{2-methoxy-3-(4-octadecylsulfamoyl)benzylcarbamoyloxypropyloxy{-carbonyl]aminomethylpyridinium chloride

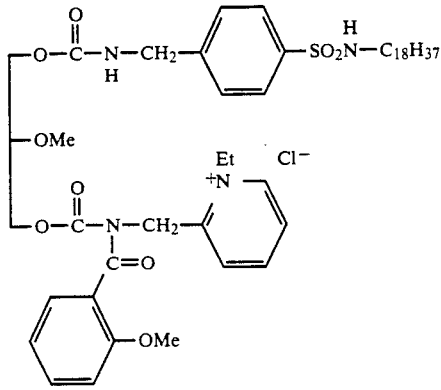

(1) Synthesis of 2-O-methyl-1-O-(4-octadecylsulfamoyl)benzylcarbamoyl-3-O-(2-pyridyl)methylcarbamoylglycerol

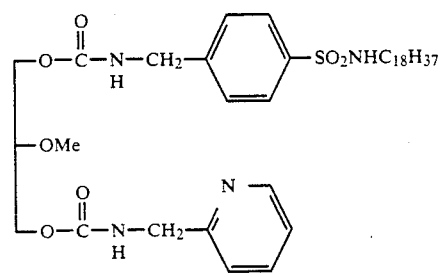

14.0 g of 2-O-methyl-3-O-(2-pyridyl)methylcarbamoyl-1-O-(4-sulfamoyl)benzylcarbamoylglycerol prepared in Example 12-(1), 10.7 g of octadecyl bromide and 3.2 g of anhydrous potassium carbonate were dissolved in 300 ml of N,N-dimethylformamide and the solution was stirred at 60° to 70° C. for 1.5 h. The reaction solution was left to cool to room temperature and water was added thereto. The aqueous solution was extracted with 200 ml of ethyl acetate three times and the extract was washed with a saturated aqueous solution of common salt. The solvent was distilled off under reduced pressure and the residue was purified by silica gel column chromatography (eluent: ethyl acetate/n-hexane=3/2) to obtain 9.1 g of the intended product.

$^1$H—NMR (90 MHz, CDCl$_3$)δ; 0.86(t, J=7 Hz, 3H), 1.00–1.60(m, 32H), 2.68–3.00(m, 2H), 3.40(s, 3H), 3.40–3.68(m, 1H), 4.00–4.48(m, 8H), 5.00–5.24(m, 1H), 5.64–5.84(m, 1H), 5.84–6.12(m, 1H), 8.00–8.60(m, 6H), 8.68(d, J =8 Hz, 1H), 9.40(d, J=7 Hz, 1H).

(2) Synthesis of
3-O-{N-(2-methoxy)benzoyl-N-(2-pyridyl)methyl}carbamoyl-2-O-methyl-1-O-(4-octadecylsulfamoyl)benzylcarbamoylglycerol

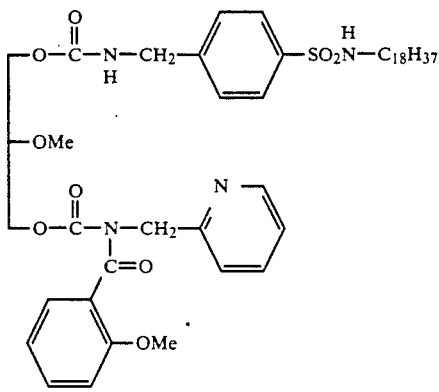

9.1 g of 2-O-methyl-1-O-(4-octadecylsulfamoyl)benzylcarbamoyl-3-O-(2-pyridyl)methylcarbamoylglycerol prepared in the above-described step (1) was dissolved in 100 ml of pyridine. 2.2 g of 2-methoxybenzoyl chloride was added dropwise thereto. The mixture was stirred at room temperature for 12 h. Pyridine was distilled of under reduced pressure and the residue was dissolved in 200 ml of ethyl acetate. The organic layer was washed with a saturated aqueous solution of common salt. The solvent was distilled off under reduced pressure and the residue was purified by silica gel column chromatography (eluent: ethyl acetate/hexane=6/4) to obtain 4.4 g of the intended product.

$^1$H—NMR (90 MHz, CDCl$_3$)δ; 0.88(t, J=6 Hz, 3H), 1.00–1.60(m, 32H), 2.90(q, J=8 Hz, 2H), 3.06–3.32(m, 1H), 3.20(s, 3H), 3.82(s, 3H), 3.75–4.20(m, 4H), 4.40(d, J=7 Hz, 2H), 4.78–4.92(m, 1H), 5.22(s, 2H), 5.56–5.72(m, 1H), 6.84–7.76 (m, 10H), 7.80(d, J=8 Hz, 1H), 8.53(d, J=7 Hz, 1H).

(3) Synthesis of
1-ethyl-2-[N-(2-methoxy)benzoyl-N-{2-methoxy-3-(4-octadecylsulfamoyl)benzylcarbamoyloxypropyloxy}carbonyl]aminomethylpyridinium chloride

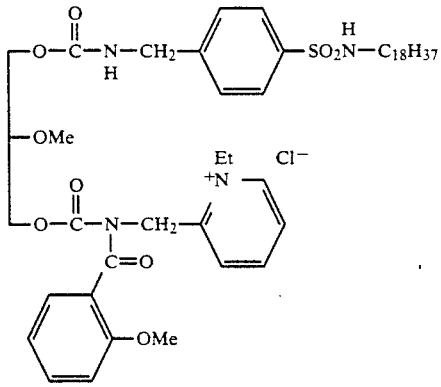

1.9 g of 3-O-{N-(2-methoxy)benzoyl-N-(2-pyridyl)methyl}carbamoyl-2-O-methyl-1-O-(4-octadecylsulfamoyl)benzylcarbamoylglycerol prepared in the above-described step (2) was dissolved in 50 ml of ethyl iodide and the solution was refluxed for 24 h. Ethyl iodide was distilled off under reduced pressure and the residue was treated with an ion exchange resin [Amberlite IRA-410, Cl$^-$ type] (eluent: methanol/water=7/3). The solvent was distilled off under reduced pressure and the residue was purified by silica gel column chromatography (eluent: methylene chloride/methanol =9/1) to obtain 1.3 g of the intended product.

$^1$H—NMR (90 MHz, CDCl$_3$)δ; 0.85(t, J=7 Hz, 3H), 1.10–1.38(m, 32H), 1.57(t, J=7 Hz, 3H), 2.67(q, J=7 Hz, 2H), 3.09(s, 3H), 3.10–3.20(m, 1H), 3.60–3.68 (m, 1H), 3.71–3.79(m, 1H), 3.85(s, 3H), 4.10–4.20(m, 1H), 3.95–4.02(m, 1H), 4.20–4.25(m, 2H), 4.75(q, J=7 Hz, 2H), 5.53(s, 2H), 7.01–7.21(m, 2H), 7.38–7.53(m, 5H) 7.73(d, J=9 Hz, 2H), 7.82(t, J=6 Hz, 1H), 7.99(d, J=8 Hz, 1H), 8.07(t, J=7 Hz, 1H), 8.64 (t, J=7 Hz, 1H), 9.12(d, J=7 Hz, 1H).

EXAMPLE 14

1-Ethyl-2-[N-(2-methoxy)benzoyl-N-{2-methoxy-3-(3-octadecylcarbamoyloxy)propylcarbamoyloxy}propoxycarbonyl]aminomethylpyridinium chloride

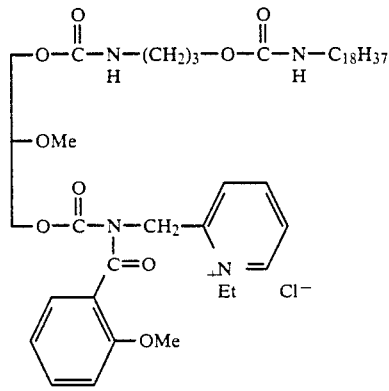

(1) Synthesis of
1-O-(3-hydroxy)propylcarbamoyl-2-O-methyl-3-O-(2-pyridyl)methylcarbamoylglycerol

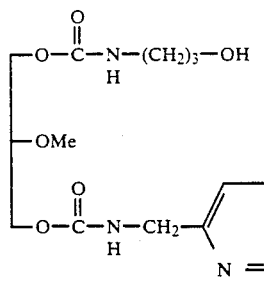

10 g of 2-O-methyl-1-O-phenoxycarbonyl-3-O-{N-(2-pyridyl)methyl}carbamoylglycerol prepared in Example 3-(2) and 3.75 g of 3-amino-1-propanol were dissolved in 10 ml of chloroform and the solution was stirred at room temperature for 1 h. The solvent was distilled off and the residue was purified by silica gel column chromatography (eluent: ethyl acetate) to obtain 8 g of the intended product.

$^1$H—NMR (90 MHz, CDCl$_3$)δ; 1.69(m, 2H), 2.68–3.76(m, 6H), 3.43(s, 3H), 3.94–4.32(m, 4H), 4.46(d, J=5 Hz, 2H), 5.21(b, 1H), 5.95(b, 1H), 6.98–7.36 (m, 2H), 7.48–7.74(m, 1H), 8.48(m, 1H).

(2) Synthesis of
2-O-methyl-1-O-(3-octadecylcarbamoyloxy)propylcarbamoyl-3-O-(2-pyridyl)methylcarbamoylglycerol

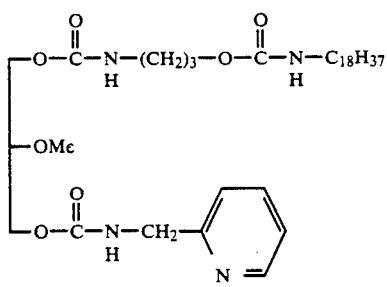

1.56 g of phenyl chloroformate was added dropwise to 50 ml of a solution of 2.9 g of 1-O-(3-hydroxy)propylcarbamoyl-2-O-methyl-3-O-(2-pyridyl)methylcarbamoylglycerol and 1.3 g of pyridine in methylene chloride under cooling with ice and the mixture was stirred for 15 min. The reaction solution was washed with a saturated aqueous solution of sodium hydrogen-carbonate and then with water and dried over anhydrous magnesium sulfate. The solvent was removed and a residue thus formed was mixed with 3 g of octadecylamine. The mixture was stirred at 80° C. for 1 h. After cooling, the product was purified by silica gel column chromatography (eluent: ethyl acetate/n-hexane = 1/1) to obtain 3 g of the intended product.

$^1$H—NMR (90 MHz, CDCl$_3$)δ; 0.87(m, 3H), 0.98-1.87(m, 34H), 2.86-3.71(m, 5H), 3.43(s, 3H), 3.95-4.25(m, 6H), 4.43(d, J=5 Hz, 2H), 4.76(b, 1H), 5.11(b, 1H), 5.87(b, 1H), 6.98-7.29(m, 2H), 7.47-7.72(m, 1H), 8.47(m, 1H).

(3)
3-O-{N-(2-Methoxy)benzoyl-N-(2-pyridyl)methyl}carbamoyl-2-O-methyl-1-O-(3-octadecylcarbamoyloxy)-propylcarbamoylglycerol

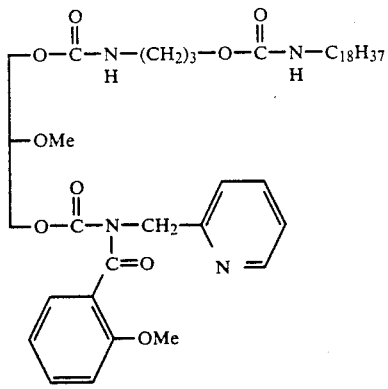

3 g of 2-O-methyl-1-O-(3-octadecylcarbamoyloxy)-propylcarbamoyl-3-O-(2-pyridyl)methylcarbamoylglycerol prepared in the above-described step (2) was dissolved in 50 ml of pyridine. 1.3 g of 2-methoxybenzoyl chloride was added to the solution at room temperature and the mixture was stirred at 50° C. for 2 h. After cooling, the solvent was distilled off and the residue was dissolved in chloroform. The solution was washed with a saturated aqueous solution of sodium hydrogen-carbonate and then with water and dried over anhydrous magnesium sulfate. The solvent was distilled off and the residue was purified by silica gel column chromatography (eluent: ethyl acetate/n-hexane = 1/1) to obtain 3 g of the intended product.

$^1$H—NMR (90 MHz, CDCl$_3$)δ; 0.85(m, 3H), 1.04-1.92(m, 34H), 2.88-3.86(m, 7H), 3.16(s, 3H), 3.80(s, 3H), 3.90-4.18(m, 4H), 4.68(b, 1H), 4.88-5.30(b, 1H), 5.16(s, 2H), 6.68-7.68(m, 7H), 8.44(m, 1H).

(4)
1-Ethyl-2-[N-(2-methoxy)benzoyl-N-{2-methoxy-3-(3-octadecylcarbamoyloxy)propylcarbamoyloxy}propoxycarbonyl]aminomethylpyridinium chloride

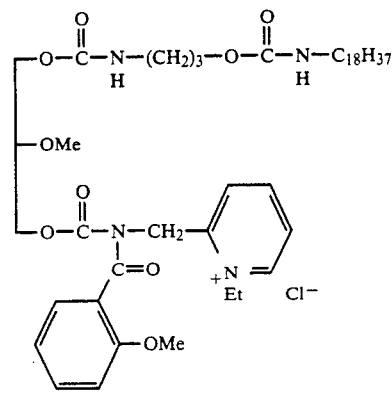

3.0 g of 3-O-{N-(2-methoxy)benzoyl-N-(2-pyridyl)methyl}carbamoyl-2-O-methyl-1-O-(3-octadecylcarbamoyloxy)propylcarbamoylglycerol prepared in the above-described step (3) was dissolved in 60 ml of ethyl iodide. The solution was refluxed in a nitrogen atmosphere for 48 h while shielding light. After cooling, the solvent was distilled off and the residue was treated with an ion exchange resin [Amberlite IRA-410, Cl$^-$ type] (eluent: methanol/water=7/3) and then purified by silica gel column chromatography (eluent: methanol/methylene chloride=1/9) to obtain 2.8 g of the intended product.

$^1$H—NMR (90 MHz, CDCl$_3$)δ; 0.88(m, 3H), 1.02-1.42(m, 34H), 1.78(t, J=7 Hz, 3H), 3.04-3.90(m, 7H), 3.23(s, 3H), 3.92(s, 3H), 4.00-4.24(m, 4H), 4.88-5.10(b, 1H), 5.30(m, 2H), 5.48-5.76(b, 1H), 5.59(s, 2H), 6.92-7.20(m, 2H), 7.40-7.65(m, 2H), 8.01-8.26(m, 2H), 8.36-8.64(m, 1H), 10.20-10.40(m, 1H).

EXAMPLE 15

1-Ethyl-2-[N-(2-methoxy)benzoyl-N-{2-methoxy-3-(4-octadecylcarbamoyloxy)piperidinocarbonyloxypropyloxy}carbonyl]aminomethylpyridinium chloride

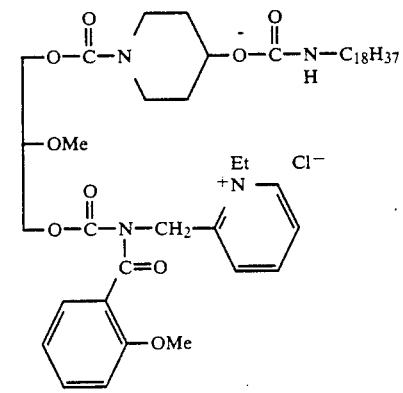

(1) Synthesis of 1-O-(4-hydroxy)piperidinocarbonyl-2-O-methyl-3-O-{N-(2-pyridyl)methyl}carbamoylglycerol

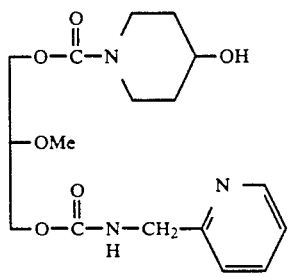

10 g of 2-O-methyl-1-O-phenoxycarbonyl-3-O-{N-(2-pyridyl)methyl}carbamoylglycerol prepared in Example 3-(2) was dissolved in 20 ml of chloroform. 5.6 g of 4-hydroxypiperidine was added to the solution and the mixture was heated under reflux for 30 min. The reaction solution was concentrated to dryness at room temperature under reduced pressure and the residue was purified by silica gel column chromatography (eluent: ethyl acetate/methanol=95/5) to obtain 10.3 g of the intended product.

$^1$H—NMR (90 MHz, CDCl$_3$)δ; 1.40–2.10(m, 4H), 3.13(m, 2H), 3.55(s, 3H), 2.53–4.12(m, 5H), 4.13–4.29(m, 4H), 4.48(d, 2H), 5.93(m, 1H), 8.13–8.36(m, 2H), 8.69(m, 1H), 8.55(m, 1H).

(2) Synthesis of 2-O-methyl-1-O-{4-(phenoxycarbonyl)oxypiperidino}carbonyl-3-O-{N-(2-pyridyl)methyl}carbamoylglycerol

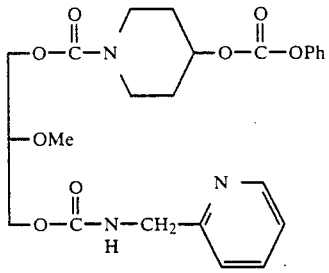

9 g of 1-O-(4-hydroxy)piperidinocarbonyl-2-O-methyl-3-O-{N-(2-pyridyl)methyl}carbamoylglycerol prepared in the above-described step (1) was dissolved in 90 g of pyridine. 3.8 g of phenyl chloroformate was added dropwise to the solution under stirring and under cooling with ice. After 30 min, the reaction solution was added to 90 ml of a saturated aqueous solution of sodium hydrogencarbonate. The mixture was subjected to extraction with 50 ml of methylene chloride three times. The organic layers were combined, dired over anhydrous magnesium sulfate and concentrated under reduced pressure. The residue was purified by silica gel column chromatography (eluent: ethyl acetate/n-hexane=2/1) to obtain 10 g of the intended product.

$^1$H—NMR (90 MHz, CDCl$_3$)δ; 1.68–2.20(m, 4H), 3.23–4.00(m, 5H), 3.50(s, 3H), 4.10–4.42(m, 4H), 4.52(d, J =7 Hz, 2H), 4.95(m, 1H), 6.10(m, 1H), 7.15–7.86(m, 8H), 8.58(m, 1H).

(3) (a) Synthesis of 2-O-methyl-3-O-{N-(2-pyridyl)methyl}carbamoyl-1-O-(4-octadecylcarbamoyloxy)piperidinocarbonylglycerol

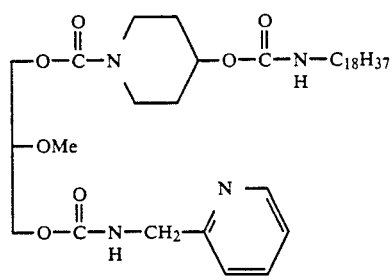

6.27 g of 2-O-methyl-1-O-{4-(phenoxycarbonyl)oxypiperidino}carbonyl-3-O-{N-(2-pyridyl)methyl}carbamoylglycerol prepared in the above-described step (2) was dissolved in 15 ml of methylene chloride. Octadecylamine was added to the solution to form a homogeneous solution. The solvent was distilled of and the residue was heated at 100° C. for 10 min. The reaction solution was left to cool to room temperature and the product was purified by silica gel column chromatography (eluent: acetone/hexane=1/2) to obtain 7.9 g of the intended product.

(b) (an alternate method)

1.1 g of 1-O-(4-hydroxy)piperidinocarbonyl-2-O-methyl-3-O-{N-(2-pyridyl)methyl}carbamoylglycerol prepared in the above-described step (1) was dissolved in 20 ml of pyridine. 900 mg of octadecyl isocyanate was added to the solution and the mixture was stirred at 100° C. for 12 h. The reaction solution was left to cool to room temperature and concentrated under reduced pressure. The residue was purified by silica gel column chromatography (eluent: ethyl acetate/n-hexane =2/1) to obtain 900 mg of the intended product.

$^1$H—NMR (90 MHz, CDCl$_3$)δ; 0.72–1.00(m, 3H), 1.04–2.08(m, 36H), 3.00–3.94(m, 7H), 3.44(s, 3H), 4.03–4.40(m, 4H), 4.50(d, J=7 Hz, 2H), 4.87(m, 2H), 6.10(m, 1H), 7.10–7.40(m, 2H), 7.70(m, 1H), 8.55(m, 1H).

(5) Synthesis of 3-O-{N-(2-methoxy)benzoyl-N-(2-pyridyl)methyl}carbamoyl-2-O-methyl-1-O-(4-octadecylcarbamoyloxy)piperidinocarbonylglycerol

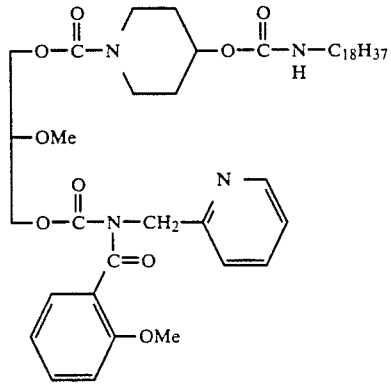

7.85 g of 2-O-methyl-3-O-{N-)2-pyridyl)methyl}carbamoyl-1-O-(4-octadecylcarbamoyloxy)piperidinocarbonylglycerol prepared in the above-described step (3) was dissolved in 78 ml of pyridine. 2.1 ml of 2-methoxybenzoyl chloride was added dropwise to the solution under stirring at room temperature and the reaction was conducted for 1 h. The reaction solution was added to 80 ml of a saturated aqueous solution of sodium hydrogencarbonate and the mixture was extracted with 100 ml of methylene chloride three times. The organic layer were combined, dried over anhydrous magnesium sulfate and concentrated to dryness under reduced pressure. The residue was purified by silica gel column chromatography (eluent: ethyl acetate/n-hexane =2/1) to obtain 7.8 g of the intended product.

$^1$H—NMR (90 MHz, CDCl$_3$)δ; 0.73–1.02(m, 3H), 1.09–1.45(m, 32H), 1.50–1.90(m, 4H), 3.02–3.39(m, 5H), 3.21(s, 3H), 3.52–3.80(m, 5H), 3.85(s, 3H), 4.00–4.13(m, 2H), 4.53–4.93(m, 1H), 5.25(s, 2H), 6.84–7.80(m, 7H), 8.58(m, 1H).

(5) Synthesis of 1-ethyl-2-[N-(2-methoxy)benzoyl-N-{2-methoxy-3-(4-octadecylcarbamoyloxy)piperidinocarbonyloxypropyloxy}carbonyl]aminomethylpyridinium chloride

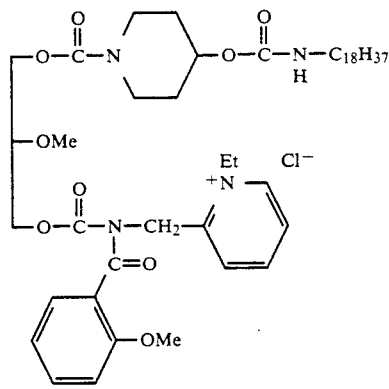

60 ml of ethyl iodide was added to 6.2 g of 3-O-{N-(2-methoxy)benzoyl-N-(2-pyridyl)methyl}carbamoyl-2-O-methyl-1-O-(4-octadecylcarbamoyloxy)-piperidinocarbonylglycerol prepared in the above-described step (4) and the mixture was refluxed in a nitrogen atmosphere for 48 h. The reaction solution was left to cool to room temperature and concentrated to dryness. The residue was treated with an ion exchange resin [Amberlite IRA-410, Cl$^-$ type] (eluent: methanol/water=7/3) to obtain 7.5 g of a crude chloride. It was purified by silica gel column chromatography (eluent: methanol/methylene chloride =5/95) to obtain 7 g of the intended product.

$^1$H—NMR (400 MHz, CDCl$_3$)δ; 0.87(t, 3H), 1.18–1.35(m, 32H), 1.42–2.25(m, 5H), 1.80(t, 3H), 3.15(m, 2H), 3.23(s, 3H), 3.23–3.35(m, 3H), 3.65(m, 2H), 3.78(m, 1H), 3.85(m, 1H), 3.90(s, 3), 4.05(m, 1h), 4.15(m, 1H), 4.82(m, 1H), 5.25(q, 2H), 5.52(br, 2H), 6.94(d, J=9 Hz, 1H), 7.07(dd, J=8 Hz, 7 Hz, 1H), 7.49(m, 2H), 8.05(m, 2H), 8.36(m, 1H), 10.34(m, 1H) FAB 8.25(M$^-$).

WORKING EXAMPLE 16

1-ethyl-2-(((N-acetyl-N-((C2-methoxy-3-((2-(3,4,5-trimethoxy)phenylethyl))oxypropyl)))oxycarbonyl)-))aminomethyl pyridinium iodide

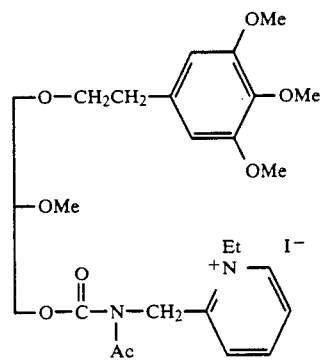

(1) Synthesis of (3,4,5-trimethoxy)phenylacetonitrile

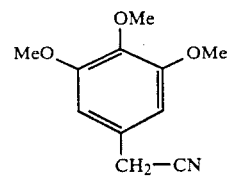

3,4,5-trimethoxy benzyl chloride 7.0 g and sodium cyanide 6.3 g were dissolved into 50 ml of N,N-dimethylformamide and they were then stirred at 80° C. for 45 minutes. The temperature of the reactive liquid was then lowered down to the room temperature, 200 ml of water was added thereto and then extraction was made thrice by means of 100 of ethyl acetate.

The liquids thus extracted was washed by saturated saline solution, then the solvent was distilled under reduced pressure to have 5.5 g of captioned compound.

(2) Synthesis of (3,4,5)trimethoxy)phenylacetic acid

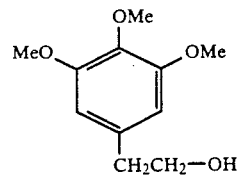

3,4,5-trimethoxyphenyl acetonitrile 5.5 g was dissolved into 50 ml of methanol/water (9:1). To this 1.5 g of sodium hydroxide was added and they were then stirred and refluxed for 5.5 hours. The temperature of the reactive liquid was lowered down to room temperature and neutralized with 2N hydrochloric acid, and the methanol was distilled off under reduced pressure. Extraction was performed thrice by means of 100 of chloroform. After distilling off the solvent under reduced pressure, 5.8 g of captioned compound was obtained.

(3) Synthesis of 2-(3,4,5-trimethoxy)phenyl ethanol

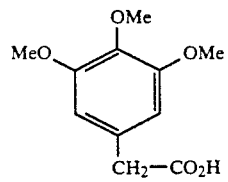

1.0 g of lithium aluminum hydride was suspended into 50 ml of tetrahydrofuran, into which was dropped under incubation on ice 5.8 g of phenylacetate. The temperature of reactive liquid was lowered down to room temperature.

The liquid was stirred for 30 minutes. This reactive liquid was incubated on ice to which water first and then concentrated hydrochloric acid was dropped to make the liquid acidic and extraction was performed thrice by means of 50 ml of ethylacetate. The liquid thus extracted was washed in saturated saline water and the solvent was distilled off under reduced pressure. Then the residue was purified by silica gel column chromatography (eluate solvent; ethylacetate: hexane=1:1) to obtain the captioned compound.

$^1$H—NMR (90 MHz, CDCl$_3$)δ; 2.02(br, s, 1H), 2.86(t, J=6 Hz, 2H), 3.80-4.00(m, 2H), 3.87(s, 3H), 3.90 (s, 6H), 6.47(s, 2H).

(4) Synthesis of 2-O-methyl-1-O-((2-(3,4,5-trimethoxy)phenyl))ethyl glycerin

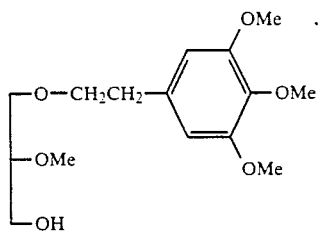

2.7 g of 2-(3,4,5-trimethoxy)phenyl ethanol was dissolved into 50 ml of N,N-dimethylformamide, to which 0.9 g of sodium hydride (60%) was added, and all these were stirred at room temperature for 30 minutes. To this was added 3.8 g of 1-O-methanesulfonyl-2-O-methyl-3-tetrahydropyran-2-ylglycerin and these were stirred for 1 hour. The reactive liquid was brought to room temperature and water was added. Extraction was then performed thrice by means of 50 ml of ethylacetate. The liquid thus extracted was washed with saturated saline water, the solvent was distilled off under reduced pressure and the residue was ressolved into 50 ml of methanol/water (9:1), to which 100 mg of paratoluenesulfonate was added. These were stirred for 1 hour. The methanol was distilled off under reduced pressure and water was added. Then extraction was performed thrice by means of 50 ml of ethyacetate. The organic layer was washed by saturated aqueous solution of sodium bicarbonate and saturated saline water. After distilling off the solvent under reduced pressure, the residue was purified by means of silica gel column chromatography (eluate solvent; ethylacetate:hexane=2:3) to get 2.1 g of the captioned compound.

$^1$H—NMR (90 MHz, CDCl$_3$)δ; 2.42(br, s, 1H), 2.83(t, J=7 Hz, 2H), 3.44(s, 3H), 3.28-3.88(m, 7H), 3.82 (s, 3H), 3.85(s, 6.H), 6.43(s, 2H).

(5) Synthesis of 2-O-methyl-3-O-(2-pyridyl)methylcarbamoyl-1-O-((2-(3,4,5-trimethoxy)phenyl))etthyl glycerin

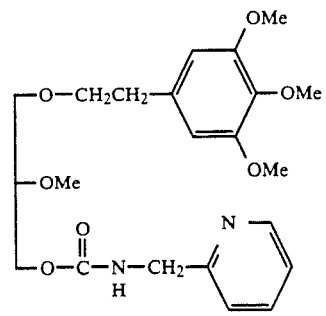

2.1 g of the compound as obtained under (4) above was dissolved into 20 ml of pyridine, to which 1.2 g of phenyl chloroformate was dropped stirring the whole under room temperature. After stirring these at room temperature for 15 minutes, the pyridine was distilled off under reduced pressure and the residue was dissolved into 200 ml of ethylacetate. This was washed with saturated saline water, the solvent was distilled off under reduced pressure and the residue was dissolved into 100 ml of chloroform. To this 2.3 g of 2-aminomethyl pyridine was added and the mixture was heated and refluxed for 5 hours. After distilling off the chloroform under reduced pressure, the residue was purified by silica gel column chromatography (eluate solvent; ethylacetate:hexane=2:1) to finally obtain 1.7 g of the captioned compound.

$^1$H—NMR (90 MHz, CDCl$_3$)δ; 2.82(t, J=8 Hz, 2H), 3.40-3.80(m, 5H), 3.80(s, 3H), 3.83(s, 6H), 4.16-4.32 (m, 2H), 4.50(d, J=6 Hz, 2H), 5.68-5.96 (m, 1H), 6.42(s, 2H), 7.04-7.30(m, 2H), 7.65(dt, J=8 Hz, 2 Hz, 1H), 8.90(d, J=8 Hz, 1H).

(6) Synthesis of 3-O-(((N-acetyl-N-(2-pyridyl)methylcarbamoyl)))-2-O-methyl-1-O-(((2-(((3,4,5-trimethoxy) phenyl)) ethyl))) glycerin

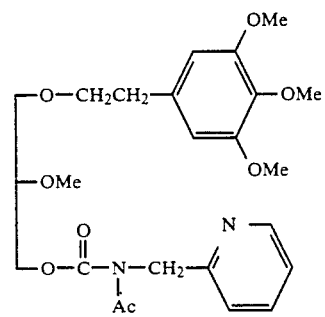

1.7 g of the compound as obtained by (5) was dissolved into 10 ml of pyridine, to which 10 ml of acetic anhydride was added. These were then stirred at 100° C. for 2 days. Pyridine and acetic anhydride were distilled off under reduced pressure and the residue was purified by silica gel column chromatography (eluate solvent; ethylacetate: hexane=2:1) to obtain 1.1 g of the captioned compound).

¹H—NMR (90 MHz, CDCl₃)δ; 2.64(s, 3H), 2.76(t, J=8 Hz, 3H), 3.29 (s, 3H), 3.30–3.44(m, 4H), 3.55(t, J=8 Hz), 3.83(s, 3H), 3.84(6H), 4.24 (t, J=5 Hz, 2H), 5.08(s, 2H), 6.40(s, 2H), 7.00–7.20(m, 2H), 7.59(dt, J=8 Hz, 2 Hz, 1H), 8.47(dd, J=8 Hz, 2 Hz, 1H).

(7) Synthesis of
1-ethyl-2-(((N-acetyl-N-(((2-methoxy-3-((2-(3,4,5-trimethoxy) phenylethyl)) oxypropyl)) oxycarbonyl))) aminomethyl pyridium iodide

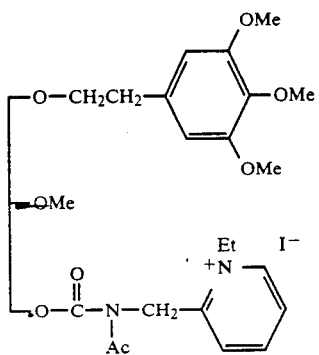

1.1 if the compound as obtained by (6) was dissolved into 20 ml of ethyl iodide and these were heated and refluxed for 24 hours. The reactive liquid was brought to room temperature, and the insoluble matter was filtered out and dissolved into acetone. By adding ether it was then precipitated again. Removal of the supernatant gave the captioned compound.

¹H—NMR (90 MHz, CDCl₃)δ; 1.72(t, J=8 Hz, 3H), 2.62(s, 3H), 2.80 (t, J=8 Hz, 2H), 3.36(s, 3H), 3.06–3.32 (m, 1H), 3.44–3.80(m, 4H), 3.79(s, 3H), 3.84(s, 6H), 4.28–4.44(m, 2H), 5.02 (q, J=8 Hz, 2H), 5.38(s, 2H), 6.42(s, 2H), 7.75(d, J=8 Hz, 1H), 8.03(t, J=8 Hz, 1H), 8.48(t, J=8 Hz, 1H), 9.57(d, J=8 Hz, 1H)

WORKING EXAMPLE 17

1-ethyl-2-(((N-acetyl-N-((2-methoxy-3-(3,4,5-trimethoxy) phenoxypropyloxy)) carbonyl))) aminomethyl pyridium iodide

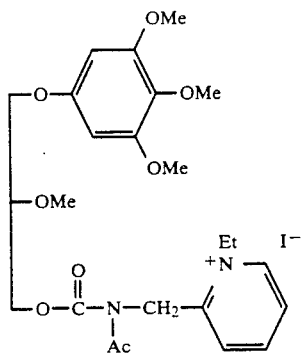

(1) Synthesis of
3-O-(tetrahydro-2H)-pyran-2-yl)-2-O-methyl glycerin

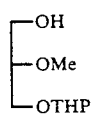

26.7 g of glycerin-2-methylether was dissolved into 260 ml of methylene chloride. Stirring this solution under incubation on ice, 10.6 g of dihydropyran and 2.7 g of p-toluenesulfonic acid were added. These were reacted for 1.5 hour under room temperature. The reactive liquid was added to saturated aqueous solution of sodium bicarbonate, and extraction was twice made by means of 100 of methylene chloride. Organic layers were gathered, dried by magnesium sulfate and concentrated under reduced pressure.

The residue was purified by the silica gel column chromatography (eluate solvent; ethylacetate:hexane=1:2) and the captioned compound was obtained in 13.6 g.

¹H—NMR (90 MHz, CDCl₃)δ; 1.36–1.96(m, 6H), 2.54(bs, 1H), 2.32–3.00(m, 7H), 3.28(s, 3H), 4.58(m, 1H)

(2) Synthesis of
1-O-methanesulfonyl-3-O-(tetrahydro-2H-pyran-2-yl)-2O-methyl glycerin

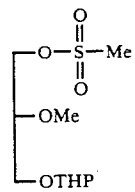

0.9 g of the compound as obtained by (1) was dissolved into 10 ml of pyridine and 0.7 ml of methanesulfonyl chloride was added thereto stirring under room temperature to react for 30 minutes. The reactive liquid was then added to saturated aqueous solution of sodium bicarbonate and extraction was made twice by means of 20 ml of chloroform. The organic layers were gathered, dried by magnesium anhydride and then concentrated under reduced pressure. The residue was purified by the silica gel column chromatography (eluate solvent; ethylacetate:n-hexane=1:2) and the captioned compound was obtained in 1.1 g.

¹H—NMR (90 MHz, CDCl₃)δ; 1.36–2.96(m, 6H), 3.02(s, 3H), 3.30–3.97(m, 5H), 3.24(s, 3H), 4.20–4.38 (m, 2H), 4.35(m, 1H).

(3) Synthesis of
1-O-(3,4,5-trimethoxyphenyl)-3-O-(tetrahydro2H-pyran-2-yl)-2-O-methyl glycerin

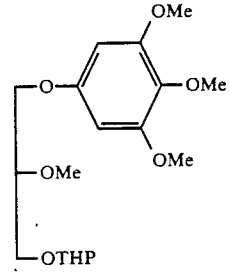

1.0 g of 3,4,5-trimethoxyphenol was dissolved into 20 ml of N,N-dimethylformamide and 280 mg of sodium hydroxide (60%) was added thereto stirring the whole under room temperature. After one hour, 5 ml of N,N-dimethylformamide solution (1.0 g/5 ml) of the compound as obtained by (2) was dropped to react at 60° C. for 1 hour. The reactive liquid was then brought to room temperature and added to saturated aqueous solution of sodium bicarbonate and extraction was made twice by means of 20 ml of chloroform. The organic layers were gathered, dried by magnesium anhydride and then concentrated under reduced pressure. The residue was purified by the silica gel column chromatography (eluate solvent; ethylacetate:n-hexane=1:2) and the captioned compound was obtained in 1.3 g.

$^1$H—NMR (90 MHz, CDCl$_3$)δ; 1.40–1.92(m, 6H), 3.32–4.24(m, 7H), 3.52(s, 3H), 3.78(s, 3H), 3.84(s, 6H), 4.62(m, 1H), 6.18(s, 2H).

(4) Synthesis of 2-O-methyl-1-O-(3,4,5-trimethoxyphenyl) glycerin

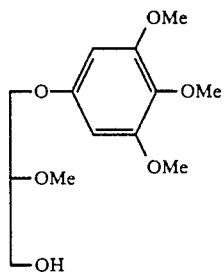

1.3 g of the compound as obtained by (3) was dissolved into 26 ml of methanol and 0.4 g of p-toluenesulfonic acid was added thereto stirring the whole under room temperature to react for 3 hours. The reactive liquid was then added to saturated aqueous solution of sodium bicarbonate and extraction was made thrice by means of 20 ml of chloroform. The organic layers were gathered, dried by magnesium anhydride and then concentrated under reduced pressure. The residue was purified by the silica gel column chromatography (eluate solvent; ethylacetate:n-hexane=1:1) and the captioned compound was obtained in 1.0 g.

$^1$H—NMR (90 MHz, CDCl$_3$)δ; 1.20(bs, 1H), 3.54(s, 3H), 3.60–3.82 (m, 3H), 3.78(s, 3H), 3.84(s, 6H), 3.82–4.16(m, 2H), 6.16(s, 2H).

(5) Synthesis of 2-O-methyl-3-O-((N-(2-pyridyl) methyl))) carbamoyl-1-O-(3,4,5-trimethoxy) phenyl glycerin

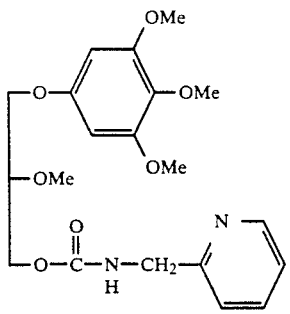

970 mg of the compound as obtained by (4) was dissolved into 20 ml of pyridine and 0.72 ml of phenyl chloroformate was dropped thereinto stirring the whole under incubation on ice. After 1 hour, the reactive liquid was added to saturated aqueous solution of sodium bicarnbonate and extraction was performed thrice with 20 ml of chloroform. Organic layers were gathered, concentrated under reduced pressure and coarse carbonate was obtained. 1.5 g of the coarse carbonate thus obtained was dissolved into 25 ml of chloroform, 1.5 ml of 2-aminomethyl pyridine was added thereto to heat and reflux for 3 hours. The reactive liquid was brought to room temperature and concentrated under reduced pressure. The residue was purified by silica gel column chromatography (eluate solvent; ethylacetate:n-hexane =2:1) and the captioned compound was given in 1.4 g.

$^1$H—NMR (90MHz, CDCl$_3$)δ; 3.50(s, 3H), 3.78(s, 3H), 3.82(s, 6H), 3.80–3.90(m, 1H), 3.87–4.20(m, 2H), 4,33(m, 2H), 4.50(d, J=7 Hz, 2H), 6.00 (br, 1H), 6.15(s, 2H), 7.03–7.40(m, 2H), 7.63(m, 1H), 7.50(m, 1H).

(6) Synthesis of 3-O-(((N-acetyl-N-(2-pyridyl) methyl))) carbamoyl-2-O-methyl-1-O-(3,4,5-trimethoxy) phenyl glycerin

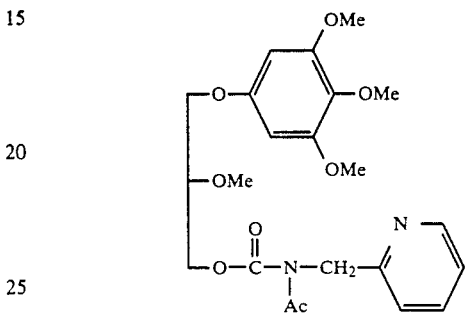

1.3 g of the compound as obtained by (5) was dissolved into 13 ml of acetic anhydride and 13 ml of pyridine to react under 110° C. for 12 hours. The reactive liquid was lowered down to room temperature, concentrated under reduced pressure, and purified by silica gel column chromatography (eluate solvent; ethylacetate:n-hexane=1:1). 1.0 g of the captioned compound was obtained.

$^1$H—NMR (90MHz, CDCl$_3$)δ; 2.60(s, 3H), 3.18(s, 3H), 3.30–3.82 (M, 3H), 3.79(s, 3H), 3.82(s, 6H), 4.36 (m, 2H), 5.08(bs, 2H), 6.06(s, 2H), 6.96–7.14(m, 2H), 7.52(m, 1H), 8.40(m, 1H)

(7) Synthesis of 1-ethyl-2-(((N-acetyl-N-((2-methoxy-3-(3,4,5-trimethoxy) phenoxypropyloxy)) carbonyl))) aminomethylpyridinium iodide

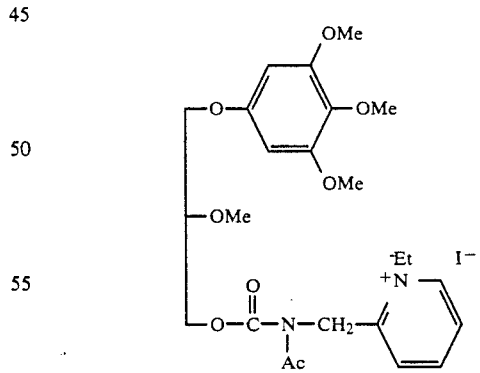

0.95 g of the compound as obtained by (6) was dissolved into 20 ml of ethyl iodide to react at 50° C. for a day. The reactive liquid was lowered down to room temperature, ether was added thereto and the supernatant was removed by decantation. The residue was dissolved into acetone added, to which ether was added again. The supernatant was removed by decantation, concentrated and evaporated into dryness. 300 mg of the captioned compound was thus obtained.

$^1$H—NMR (90MHz, CDCl$_3$)δ; 1.68(t, J=7 Hz, 3H), 2.66(s, 3H), 3.47 (s, 3H), 3.77(s, 3H), 3.66–3.88(m, 1H), 3.85(s, 6H), 4.04(m, 2H), 4.74(m, 2H), 5.00(q, J=7 Hz, 2H), 5.47(s, 2H), 6.14 (s, 2H), 7.66(m, 1H), 7.92(m, 1H), 8.26 (m, 1H), 9.34(m, 1H).

WORKING EXAMPLE 18

1-ethyl-2-(((N-((3,5-dimethoxy-4-octadecyloxy) benzyloxy-2-methoxypropyloxy)) carbonyl-N-(2-methoxy) benzoyl))) aminomethyl pyridinium chloride

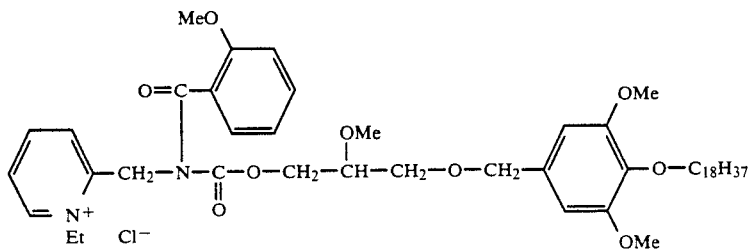

(1) Synthesis of 3,5-dimethoxy-4-octadecyloxy benzyl alcohol

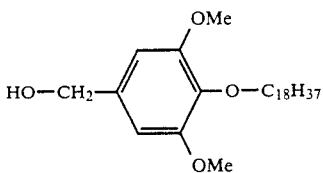

54 g of 1-octadecanol was dissolved into 500 ml of methylene chloride and 40 g of triethylamine. Under incubation on ice 45.8 g of methanesulfonyl chloride was dropped thereon and these were stirred under from temperature. The reactive liquid was washed by diluted hydrochloric acid, water and saturated aqueous solution of sodium bicarbonate in this order, and dried up by magnesium sulfur trioxide. This was then filtered off, the solvent was distilled off and the corresponding mesyl ester material was obtained quantitatively.

ii) 19 g of syringaldehyde was dissolved into 150 ml of N,N-dimethylformamide, to which 6.8 g of hydrogenated sodium (55%) was added under room temperature. These were then stirred at 80° C. for 40 minutes. Then this was incubated on ice. To this 13.5 g of potassium iodide and 47.27 g of mesyl ester material obtained by i) were added as suspended into 400 ml of N,N-dimethylformamide, and the whole was stirred again at 90° C. for 13.5 hours. After cooling down, water and chloroform were added, the insoluble was filtered off, chloroform layer was dispensed. After washing with saturated saline water, it was dried up by magnesium sulfur trioxide. After this was fileterd and the solvent was distilled off, the residue was treated by the silica gel column chromatography (eluate solvent; ethylacetate:n-hexane =5:95). 24.26 g of 3,5-dimethoxy-4-octadecyloxybenzaldehyde was thus obtained.

iii) 24.26 g of aldehyde material obtained by ii) was dissolved into 850 ml of dioxan, to which 3.15 g of hydrogenated boron sodium was added. These were then stirred at 60° C. for 2 hours. Water was added, extraction was performed with chloroform. After washing with saturated saline water, it was dried up with magnesium sulfur trioxide. This was filtered, the solvent was distilled off and the residue was treated by the silica gel column chromatography (eluate solvent; ethylacetate:n-hexane=1:4). The captioned compound was thus obtained in 18.35 g.

Aldehyde Material $^1$H—NMR (90 MHz, CDCl$_3$)δ; 0.7–1.05(m, 3H), 1.05–1.9(m, 32H), 3.91(s, 6H), 4.07(t, J=7 Hz, 2), 7.11 (s, 2H), 9.85(s, 1).

Alcohol Material $^1$H—NMR (90 MHz, CDCl$_3$)δ; 0.75–1.0(m, 3H), 1.05–1.9(m, 33H), 3.84(s, 6H), 3.94(t, J=7 Hz, 2H), 4.5–4.7(m, 2H), 6.59(s, 2H).

(2) Synthesis of 2-methoxy-3-(3,5-dimethoxy-4-octadecyloxy) bezyloxy-1-propanol

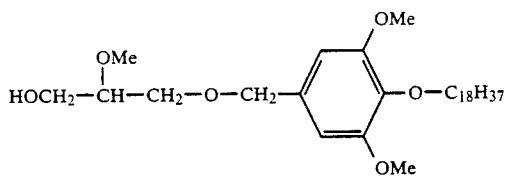

18.8 g of 3,5-dimethoxy-4-octadecyloxy benzylalcohol, 21.5 g of glycerol and 1.2 g of 1 hydrate of p-toluenesulfonic acid were dissolved into 150 ml of chloroform and these were heated and refluxed for 4 hours. Chloroform was added and the whole was washed by saturated aqueous solution of sodium bicarbonate, water and saturated saline water, in this order, and then dried up by magnesium sulfur trioxide. This was filtered and the solvent was distilled off. Then the residue was treated by silica gel column chromatography (eluate solvent; ethylacetate: n-hexane =1:9). 12.34 g of the captioned compound was thus obtained.

$^1$H—NMR (90 MHz, CDCl$_3$)δ;
0.7–1.0(m, 3H), 1.1–1.9(m, 32H), 1.9–2.2(m, 1H), 3.44(s, 3H), 3.3–3.85(m, 5), 3.80(s, 6H), 3.90(t, J=7 Hz, 2H), 4.44(s, 2H), 6.48(s, 2H).

(3) Synthesis of 1-O-(3,5-dimethoxy-4-octadecyloxy) bezyl-2-O-methyl-3-O-(2-pyridyl) methylcarbamoyl glycerin

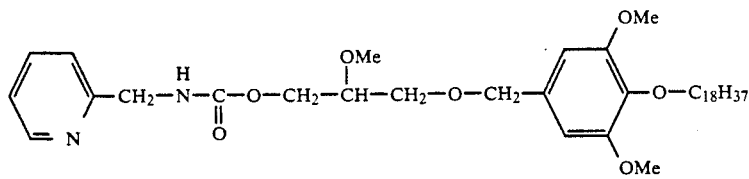

12.34 g of the alcohol material as obtained by (2) was dissolved into 250 ml of methylene chloride and 5.58 g of pyridine, onto which 7.36 g of phenyl chloroformate was dropped under incubation on ice and these were stirred as such for 30 minutes. To this was added saturated aqueous solution of sodium bicarbonate, the layer of methylene chloride was dispensed, and water layer was extracted with chloroform. This, together with the layer of methylene chloride, was dried up by magnesium sulfur trioxide. This was filtered and the solvent was distilled off. Then the residue with 7.63 g of 2-aminomethylpyridine was stirred at 80° C. for 1 hour. Then the reactive mixture was treated by silica gel column chromatography (eluate solvent; ethylacetate: n-hexane=3:2). 9.45 g of the captioned compound was thus obtained.

$^1$H—NMR (90 MHz, CDCl$_3$)δ; 0.7–1.0(m, 3H), 1.05–1.9(m, 32H), 3.48(s, 3H), 3.5–3.65(m, 3H), 3.85 (s, 6H), 3.94(t, J=7 Hz, 2H), 4.15–4.35 (m, 2H), 4.35–4.55(m, 4H), 5.65–6.0 (m, 1H), 6.57(s, 2), 7.05–7.35(m, 2H), 7.66(td, J=8 Hz, 2 Hz, 1H), 8.52(bd, J=5 Hz).

(4) Synthesis of 3-O-(3,5-dimethoxy-4-octadecyloxy) bezyl-1-O-(((N-(2-methoxy) benzoyl-N-(2-pyridyl) methylcarbamoyl))) 2-O-methylglycerin

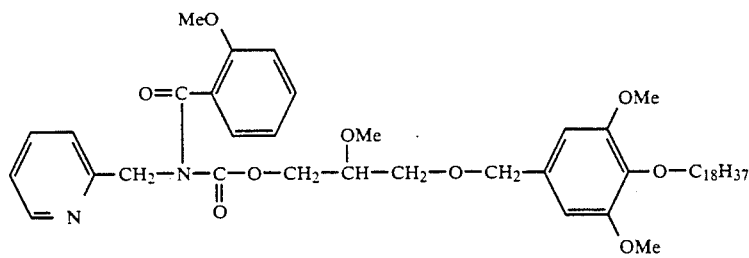

9.45 g of the pyridine material as obtained by (3) was dissolved into 200 ml of pyridine, onto which 7.40 g of 2-methoxy benzoate chloride was dropped and these were stirred at 50° C. for 1 hour. After distilling off the solvent, ethylacetate was added and these were eashed by water, saturated aqueous solution of sodium bicarbonate, and saturated saline water, in this order and then dried up by magnesium sulfur trioxide. This was filtered and the solvent was distilled off, then treated by silica gel column chromatography (eluate solvent; ethylacetate: n-hexane =35:65). 10.52 g of the captioned compound was thus obtained.

$^1$H—NMR (90 MHz, CDCl$_3$)δ; 0.65–1.0(m, 3H), 1.0–1.9(m, 32H), 3.17(s, 3H), 3.05–3.6(m, 3h), 3.78(s, 9H), 3.89(t, J=7 Hz, 2H), 3.95–4.2(m, 2H), 4.28(s, 2H), 5.17(s, 2H), 6.40(s, 2H), 6.65–7.7(m, 7H), 8.43(bd, J=5 Hz, 1H).

(5) Synthesis of 1-ethyl-2-(((N-((3-(3,5-dimethoxy-4-octadecyloxy) bezyloxy-2-methoxypropyloxy)) carbonyl-N-(2-methoxy) benzoyl))) aminomethyl pyridinium chloride

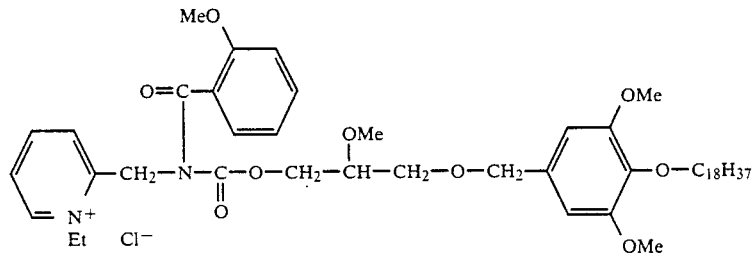

6.00 g of the 2-methoxy benzoyl material as obtained by (4) was dissolved into 120 ml of ethyl iodide and these were heated and refluxed under nitrogen current for 61 hours. After distilling off the solvent, the residue was treated by IRA-410 (Cl type, eluate solvent; methanol:water =7:3) to have chlorate. Further this was then treated by silica gel column chromatography (eluate solvent; methanol:methylene chloride=5:95). 2.80 g of the captioned compound was thus obtained.

$^1$H—NMR (90 MHz, CDCl$_3$)δ; 0.65–1.0(m, 3H), 1.0–1.9(m, 32H), 1.76(bt, J=7 Hz, 3H), 3.16(s, 3H), 2.9–3.3(m, 3H), 3.79(s, 6H), 3.84(s, 3H), 3.90(t, J=7 Hz, 2H), 4.0–4.25(m, 2H), 4.30(s, 2H), 5.15(bq, J=7 Hz, 2H), 5.39 (bs, 2H), 6.42(s, 2H), 6.65–7.1(m, 2H), 7.2–7.5(m, 2H), 7.8–8.1(m, 2H), 8.15–8.25(m, 1H), 10.15(bd, J=7 Hz, 1H).

MS m/z (FAB, Pos.); 821(M$^+$).

WORKING EXAMPLE 19

1-ethyl-2-(((N-((3-(4-biphenyl)
methyloxy-2-methoxypropyloxy))
carbonyl-N-(2-methoxy) benzoyl))) aminomethyl
pyridinium chloride

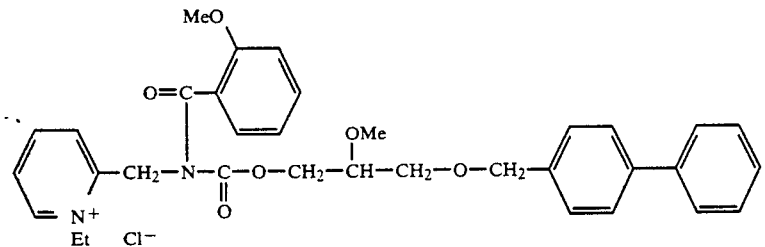

(1) Synthesis of 3-(4-biphenyl) methyloxy-2-methoxy-1-propanol

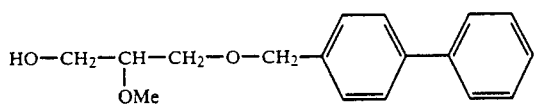

58.4 g of glycerin-2-methylether was dissolved into 420 ml of dimethylformamide and 26.3 g of hydrogenated sodium (55%) was added under incubation on ice and these were stirred at 80° C. for 50 minutes. They were then again incubated on ice, onto which 180 ml solution of N,N-dimethylformamide of 55.56 g of 4-(chloromethyl) byphenyl was dropped and stirred as such for 1 hour. Then they were stirred again at 80° C. for 2.5 hours. The reactive liquid was distilled off, water was added thereto and extraction was performed with chloroform. The chloroform layer was washed by saturated saline water, and dried up by magnesium sulfur trioxide. This was then filtered off, the solvent was distilled off. Then it was treated by silica gel column chromatography (eluate solvent; ethylacetate:n-hexane =4:6). Thus the captioned compound was obtained in 16.8 g.

$^1$H—NMR (90 MHz, CDCl$_3$)δ; 1.84(bs, 1H), 3.3-3.9(m, 5H), 3.45(s, 3H), 4.56(s, 2H), 7.1-7.7(m, 9H).

(2) Synthesis of 1-O-(4-biphenyl) methyl-2-O-methyl-3-O-(2-pyridyl) methylcarbamoyl glycerin

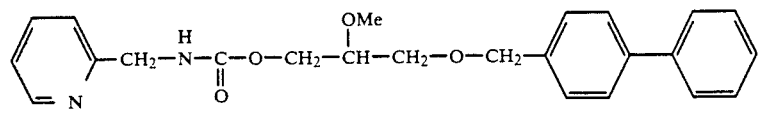

16.76 g of the alcohol material as obtained by (1) was dissolved into 300 ml of methylene chloride. to which was added 14.6 g of pyridine. To these 19.3 g of phenyl chloroformate was dropped under incubation on ice and these were stirred as such for 30 minutes. To the reactive liquid was added saturated aqueous solution of sodium bicarbonate, and they were vigorously stirred. The layer of methylene chloride was dispensed with which was matched what was extracted, by chloroform, from the water layer. These were washed with saturated saline water, dried up with magnesium sulfur trioxide, then filtered, and the solvent was distilled off. To the residue thus obtained was added 9.98 g of 2-aminomethyl pyridine, and they were stirred at 80° C. for 30 minutes. The reactive liquid was purified by the silica gel column chromatography (eluate solvent; ethylacetate:n-hexane=4:6). Thus 23.11 g of the captioned compound could be obtained.

$^1$H—NMR (90 MHz, CDCl$_3$)δ; 3.3-3.8(m, 3H), 3.44(s, 3H), 4.1-;4.4 (m, 2H), 4.45(d, J=6 Hz, 2H), 4.56(s, 2), 5.6-5.9(m, 1H), 6.95-7.7(m, 12H), 8.44(d, J=5 Hz, 1H).

(3) Synthesis of 1-O-(4-biphenyl) methyl-3-O-(((N-(2-methoxy) benzoyl-N-(2-pyridyl) methylcarbamoyl)))-2-O-methyl glycerin

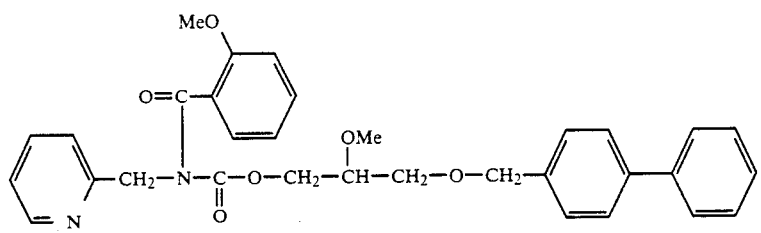

10.2 g of the pyridine material as obtained by (2) was dissolved into 100 ml of pyridine, to which was dropped 6.42 g of 2-methoxy benzoate chloride under room temperature, and they were stirred at 50° C. for 2 hours. After distilling off the solvent, ethylacetate was added, and they were washed with water, saturated aqueous solution of sodium bicarbonate, and water, in this order, then dried up with magnesium sulfur trioxide, then filtered, and the solvent was distilled off. The residue thus obtained was purified by the silica gel column chromatography (eluate solvent; ethylacetate:n-hexane=3:7). Thus 10.93 g of the captioned compound could be obtained.

¹H—NMR (90 MHz, CDCl₃)δ; 3.05-3.4(m, 3H), 3.22(s, 3H), 3.78(s, 3H), 3.95-4.2(m, 2H), 4.40(s, 2H), 5.18(s, 2H), 6.7-7.7(m, 16H), 8.4-8.55(m, 1H).

(4) Synthesis of 1-ethyl-2-(((N-((3-(4-biphenyl) methyloxy-2-methoxypropyloxy)) carbonyl-N-(2-methoxy) benzoyl))) aminomethyl pyridinium chloride

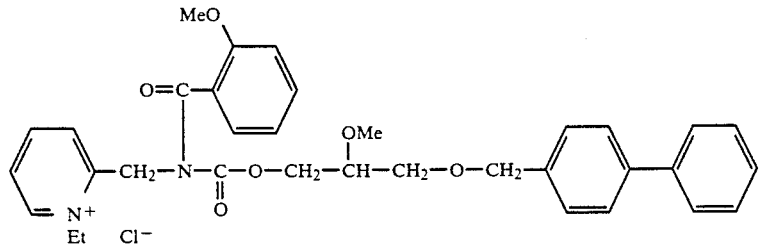

9.4 g of the 2-methoxy benzoyl material as obtained by (3) was dissolved into 100 ml of ethyl iodide and these were heated and refluxed under nitrogen current for 57 hours. The reactive liquid was distilled off, and the residue was treated with IRA-410 (Cl type, eluate solvent; methanol:water=7:3), and chlor material was given. This was further purified by silica gel column chromatography (eluate solvent; methanol:methylene chloride=5:95). Thus 8.32 g of the captioned compound was obtained.

¹H—NMR (90 MHz, CDCl₃)δ; 1.72(t, J=7 Hz, 3H), 3.1-3.4(m, 3H), 3.20(s, 3h), 3.85(s, 3), 3.95-4.4(m, 2h), 4.43(s, 2H), 5.00(q, J=7 Hz, 2H), 5.34(bs, 2H), 6.7-7.15(m, 2H), 7.15-7.75(m, 11H), 7.85-8.2(m, 2H), 8.25-8.6(m, 1H), 9.65(d, J=6 Hz, 1H).

MS m/z (FAB, Pos.); 569(m+).

WORKING EXAMPLE 20

1-ethyl-2(((N-((3-(4-cyclohexylmethoxy-3,5-dimethoxy) benzyloxy-2-methoxy)) propyloxycarbonyl-N-(2-methoxy) benzoyl))) aminomethylpyridinium chloride

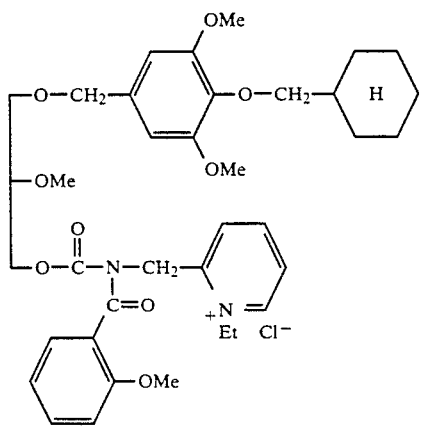

(1) Synthesis of 4-cyclohexylmethoxy-3,5-dimethoxybenzaldehyde

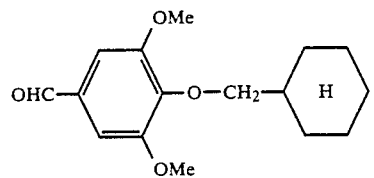

49 g hydrogenated sodium was added to 1.8 lit. of N,N-dimethylformamide solution of 171.6 g of syringaldehyde, and these were stirred at 60° C. for 30 minutes. Under incubation on ice 200 g of cyclohexylbromide and 92 g of potassium iodide were further added, and the whole was stirred again at 80° C. for 1 hour. After cooling down, 1.5 lit. of water was poured to extract with ethylacetate. Then this was dried up with magnesium sulfate.

The solvent was distilled off and the residue was purified by silica gel column chromatography (eluate solvent; ethylacetate:n-hexane=1:9). This gave 250 g of the captioned compound.

¹H—NMR (90 MHz, CDCl₃)δ; 0.70-1.04(m, 11H), 3.91(s, 6H), 3.76-3.96(m, 2H), 7.11(s, 2H), 9.85(s, 1H).

(2) Synthesis of 4-cyclohexylmethoxy-3,5-dimethoxybenzyl alcohol

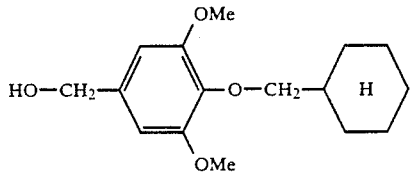

Into 60 ml of ethanol solution containing 2.3 g of the compound as obtained by (1), 0.45 g of hydrogenated sodium bromide was added, and they were stirred at 60° C. for 1 hour. After cooling down, the solvent was distilled off, water was poured thereinto to extract with chloroform and the extracted was dried up with magnesium sulfate. Distilling off the solvent thereof could give 2.3 g of the captioned compound.

¹H—NMR (90 MHz, CDCl₃)δ; 0.72-2.04(m, 11H), 3.64-3.88(m, 2H), 3.84(s, 6H), 4.52-4.66(m, 2H), 6.57(s, 2H).

(3) Synthesis of 4-cyclohexylmethoxy-3,5-dimethoxybenzyl chloride

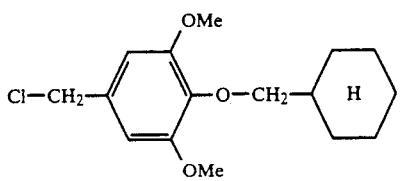

Into 100 ml of chloroform solution containing 10.6 g of the compound as obtained by (2), was dropped, under incubation on ice, 25 ml of concentrated hydrochloric acid, and these were stirred at room temperature for 2.5 hours. After taking out the chloroform layer, water washing, then washing with saturated aqueous solution of sodium bicarbonate, and with water were conducted in this order. Then this was dried up with magnesium sulfate. Then solvent was distilled off. Thus 11.3 g of the captioned compound could be obtained.

$^1$H—NMR (90 MHz, CDCl$_3$)δ; 0.68-2.04(m, 11H), 3.64-3.92(m, 2H), 3.85(s, 6H), 4.53(s, 2H), 6.61(s, 2H).

(4) Synthesis of 3-(4-cyclohexymethoxy-3,5-domethoxy)benzyloxy-2-methoxypropanol

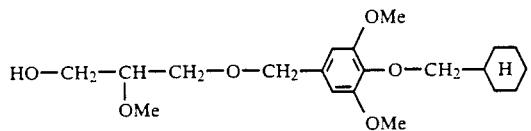

Into 250 ml of N,N-dimethylformaldehyde solution containing 21 g of 2-methoxy-1,3-propanediol, was gradually added 5.6 g of sodium iodide under incubation on ice. Then these were brought to 80° C. and stirred for 1 hour. To these was added, also under incubation on ice, 19.4 g of the compound obtained by (3) above and brought again to 80° C. to be stirred for another 1 hour. After cooling down, 1.5 lit. of water was added thereto. Extraction was conducted with 1 lit. of ethylacetate and the extracted was dried up with magnesium sulfate. The residue obtained by distilling of the solvent was purified by silica gel column chromatography (eluate solvent; ethylacetate:n-hexane =1:1), which could give 10.0 g of the captioned compound.

$^1$H—NMR (90 MHz, CDCl$_3$)δ; 0.66-2.22(m, 12H), 3.08-3.94(m, 7H), 3.44(s, 3H), 3.80(s, 6H), 4.43(s, 2H), 6.49(s, 2H).

(5) Synthesis of 1-O-(4-cyclohexylmethoxy-3,5-dimethoxy)benzyl-2-O-methyl-3-O-(2-pyridyl) methylcarbamoyl glycerin

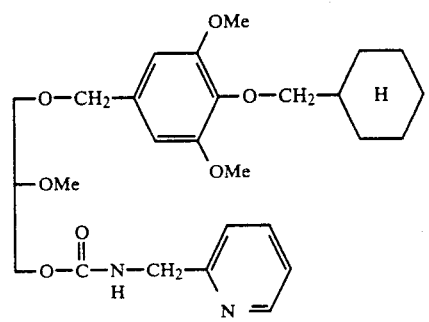

Into a mixture composed of 10.0 g of the compound obtained by (4) above, 200 ml of methylene chloride and 4.7 g of pyridine, was dropped 5 g of phenyl chloroformate under incubation on ice. Then these were stirred for 10 minutes. These were washed with saturated aqueous solution of sodium bicarbonate, then the water, and dried up with magnesium sulfate. The oily residue obtained by distilling off the solvent was dissolved into 4.3 g of 2-(aminomethyl) pyridine and stirred in hot chamber for 0.5 hour, and then purified by silica gel column chromatography (eluate solvent; ethylacetate:n-hexane=1:1). Thus 10.0 g of the captioned compound could be had.

$^1$H—NMR (90 MHz, CDCl$_3$)δ; 0.83-1.06(m, 11H), 3.36-3.94(m, 5H), 3.44(s, 3H), 3.80(s, 6H), 4.22(m, 2H), 4.32-4.52(m, 2H), 4.43(s, 2H), 5.60-5.90(br, s, 1H), 6.49(s, 2H), 7.02-7.26 (m, 2H), 7.44-7.70(m, 1H), 8.39-8.51 (m, 1H).

(6) Synthesis of 1-O-(4-cyclohexylmethoxy-3,5-dimethoxy)benzyl-3-O-(((N-(2-methoxy) benzoyl-N-(2-pyridyl) methyl))) carbamoyl-2-O-methylglycerin

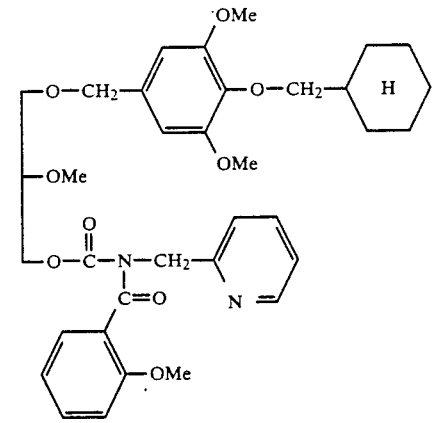

Into 200 ml of pyridine solution containing 10.0 g of the compound obtained by (5) above, was added 5.1 g of 2-methoxybenzoyl chloride under room temperature, and these were stirred at 50° C. for 2 hours. After cooling down, 300 ml of ethylacetate was added thereto, water washing and washing with saturated aqueous solution of sodium bicarbonate were performed each twice. They were then dried up with magnesium sulfate. The residue after distilling off the solvent was purified by silica gel column chromatography (eluate solvent; ethylacetate:n-hexane=1:1). Thus 9.0 g of the captioned compound was obtained.

$^1$H—NMR (90 MHz, CDCl$_3$)δ; 0.72–2.03(m, 11H), 3.18(s, 5H), 3.58–4.16(m, 5H), 3.78(s, 9H), 4.29(s, 2H), 5.19(s, 2H), 6.43(s, 2H), 6.70–7.70(m, 7H), 8.38–8.54(m, 1H).

(7) Synthesis of 1-ethyl-2-(((N-((4-cyclohexylmethoxy-3,5-dimethoxy) benzyloxy-2-methoxy) propyloxycarbonyl-N-(2-methoxy) benzoyl))) aminomethylpyridinium chloride

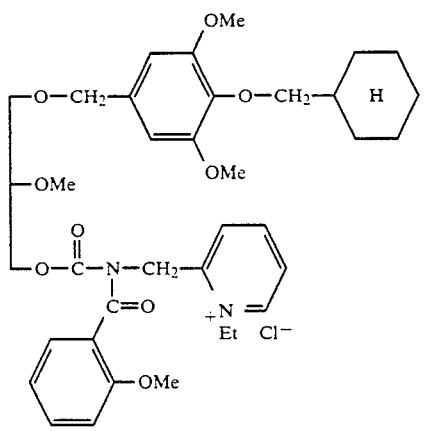

100 ml of ethyl iodide solution containing 9.0 g of the compound obtained by (6) above was stirred for 2.5 days at 80° C. in nitrogen gas with glare protection. After cooling down, the reactive liquid was concentrated and dried up to solidify, and the residue was treated by IRA-410 (Cl type, eluate solvent; methanol:water=7:3). This was then purified by silica gel column chromatography (eluate solvent; ethylene:methanol=9:1) and then freeze-dried. Thus 6.9 g of the captioned compound was obtained.

$^1$H—NMR (90 MHz, CDCl$_3$)δ; 0.95–1.07(m, 2H), 1.12–1.32(m, 3H), 1.62–1.80(m, 7H), 1.90(m, 2H), 3.18(s, 5H), 3.73(d, J=7 Hz, 2H), 3.81(s, 6H), 3.85(s, 3H), 4.06(m, 1H), 4.23(m, 1), 4.33(s, 2H), 5.20(m, 2H), 5.42(s, 2H), 6.47(s, 2H), 6.90(d, J=8 Hz, 1H), 7.05(m, 1H), 7.46(m, 2H), 7.97–8.12(m, 2H), 8.36(m, 1H), 10.27(m, 1H).

WORKING EXAMPLE 21

N,N,N-trimethyl-2(((N-((3-(4-cyclohexylmethoxy-3,5-dimethoxy) benzyloxy-2-methoxy)) propyloxycarbonyl-N-((2-(methoxy) benzoylamino))) ethylammonium iodide

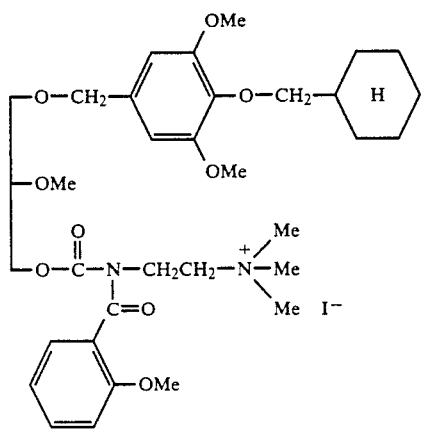

(1) Synthesis of 1-O-(4-cyclohexylmethoxy-3,5-dimethoxy) benzyl-3-O-(((2-dimethylamino) ethyl))) carbamoyl-2-O-methyl glycerin

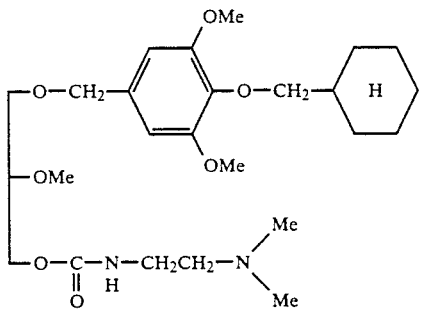

Onto a mixture composed of 8.5 g of the compound obtained by (4) of the Working Example 5 above, 4 g of pyridine and 100 ml of methylene chloride, was dropped 4.2 g of phynyl chloroformate under cooling and these were stirred for 10 minutes. They were then washed with saturated aqueous solution of sodium bicarbonate and with water. Then they were dried up with magnesium sulfate. The residue obtained by distilling off the solvent was dissolved into 8.1 g of N,N-dimethylenediamine and stirred under room temperature for 1 hour. This was then purified by silica gel column chromatography (eluate solvent; ethylacetate). Thus 10 g of the captioned compound was obtained.

$^1$H—NMR (90 MHz, CDCl$_3$)δ; 0.84–1.12(m, 11H), 2.20(s, 6), 1.36 (m, 2H), 3.21(m, 2H), 3.44(s, 3H), 3.46–3.88(m, 5H), 3.80(s, 6H), 4.17(m, 2H), 4.44(s, 2H), 5.08–5.32(m, 1H), 6.50(s, 2H).

(2) 1-O-(4-cyclohexylmethoxy-3,5-dimethoxy) benzyl-3-O-(((2-(di,ethylamino) ethyl-2-(methoxy) benzoyl))) carbamoyl-2O-methyl glycerin

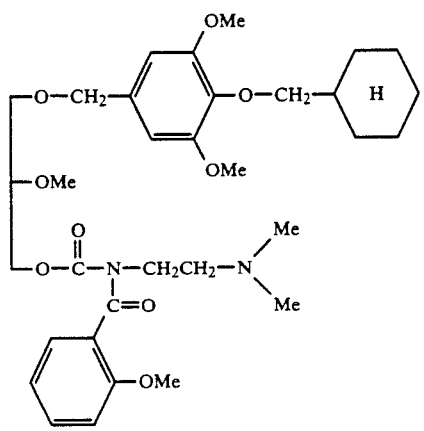

0.52 g of hydrogenated potassium (35%) was added under room temperature to 30 ml of tetrahydrofuran solution containing 1.5 g of the compound obtained by (1) above, and the whole was stirred for 30 minutes. Under incubation on ice 0.80 g of 2-methoxybenzoyl chloride was then added thereto to be stirred for 30 minutes. To these 0.56 g of acetate was added further. After stirring them under room temperature for 30 minutes, saturated aqueous solution of sodium bicarbonate was added thereto, extraction was performed with ethylacetate. After water washing, it was dried up by magnesium sulfate. The residue obtained after removal of the solvent was purified by silica gel column chromatography (eluate solvent; ethylacetate:n-hexane=4:1). Thus 0.24 of the captioned compound was obtained.

$^1$H—NMR (90 MHz, CDCl$_3$)δ; 0.76–2.03(m, 11H), 2.28(s, 6H), 2.40–2.66(m, 2H), 3.24(s, 5H), 3.60–4.13 (m, 7H), 3.73(s, 3H), 3.78(s, 6H), 4.33 (s, 2H), 6.44(s, 2H), 6.60–7.01(m, 2H), 7.18–7.42(m, 2H).

(3) Synthesis of N,N,N-trimethyl-2-(((N-((3-(4-cyclohexylmethoxy-3,5,-dimethoxy)benzyloxy-2-methoxy)) propyloxycarbonyl-N-((2(methoxy) benzoyl)) amino))) ethylammonium iodide

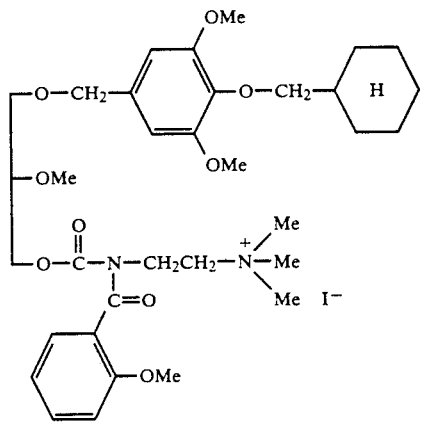

A mixture composed of 0.24 g of the compound obtained by (2), 0.11 g of methyl iodide and 10 ml of diethylether was sirred under room temperature in nitrogen atmosphere without light for 4 days. The sediment thus produced was washed with diethylether. 0.25 of the captioned compound was obtained.

$^1$H—NMR (90 MHz, CDCl$_3$)δ; 0.84–2.10(m, 11H), 3.23(s, 5H), 3.36–4.47(m, 9H), 3.51(s, 9H), 3.77(s, 3H), 3.80(s, 6H), 4.35(s, 2H), 6.46(s, 2H), 6.70–7.06(m, 2H), 7.26–7.47(m, 2H).

WORKING EXAMPLE 22

1-ethyl-2-(((N-(N,N-dimethyl) carbamyl-N-((2-methoxy-3-(3,4,5-trimethoxy) benzyloxypropyloxy)) carbonyl))) aminomethylpyridinium iodide

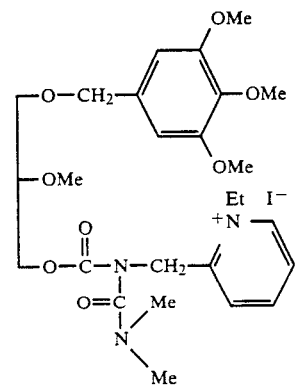

(1) Synthesis of 2-O-methyl-1-O-(3,4,5-trimethoxy) benzyl glycerin

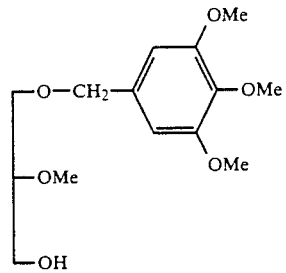

10 g of glycerin-2-methylether was dissolved into 100 ml of N,N-dimethylformamide, to which 3.8 g of hydrogenated sodium (60%) was added, and these were stirred for 1 hour at 60° C. The reactive liquid was lowered down to room temperature to which &b 8.3 g of 3,4,5-trimethoxybenzyl chloride was added to react for 1 hour. The reactive liquid was then added to 100 ml of water, and extraction was performed with 100 ml of benzene. The organic layer was gathered, dried up by magnesium sulfur trioxide and concentrated under reduced pressure. The residue was purified by silica gel column chromatography (eluate solvent; ethylacetate:n-hexane =1:1). Thus 7.5 g of the captioned compound was obtained.

$^1$H—NMR (90 MHz, CDCl$_3$)δ; 3.28–3.85(m, 6H), 3.45(s, 3H), 3.81 (s, 3H), 3.84(s, 6H), 4.25(s, 2H), 6.50 (s, 2H).

(2) Synthesis of 2-O-methyl-3-O-(((N-(2-pyridylmethyl))) carbamoyl-1-O-(3,4,5-trimethoxy) benzyl glycerin

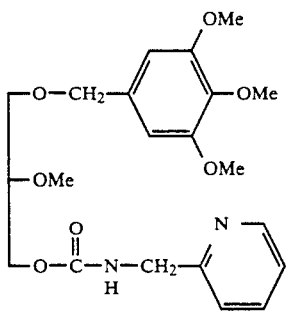

6.7 g of the compound obtained by (1) above was dissolved into 67 ml of pyridine, to which 3.5 ml of phenyl chloroformate was dropped in stirring the whole under incubation on ice to react for 1 hour. The reactive liquid was then added to saturated aqueous solution of sodium bicarbonate, and extraction was performed twice with 50 ml of dichloromethane. The organic layer was gathered, dried up by magnesium sulfur trioxide and concentrated under reduced pressure. Coarse carbonate 7.5 g was given. The coarse carbonate was dissolved into 70 ml of chloroform, to which 7 ml of 2-aminomethylpyridine was added to heat and reflux for 3 hours. The reactive liquid was brought to room temperature, and concentrated under reduced pressure. The residue was purified by silica gel column chromatography (eluate solvent; ethylacetate:n-hexane =1:1). Thus 8.8 g of the captioned compound was obtained.

$^1$H—NMR (90 MHz, CDCl$_3$)δ; 3.45(s, 3H), 3.48-3.68(m, 3H), 3.80 (s, 3H), 3.84(s, 6H), 4.14-4.30(m, 2H), 4.45(d, J=7.5 Hz, 2H), 4.46(s, 2H), 5.85(br, 1H), 6.52(s, 2H), 7.02-7.28(m, 2H), 7.60(m, 1H), 8.45(m, 1H).

(3) Synthesis of 3-O-(((N-(N,N-dimethylcarbamoyl)-N-(2-pyridyl) methyl))) carbamoyl-2-O-methyl-1-O-(3,4,5-trimethoxy) benzyl glyserin

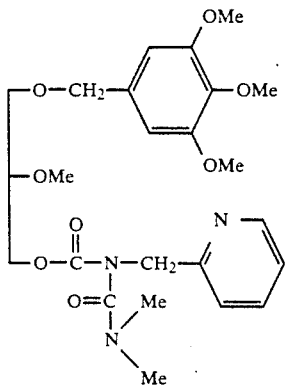

0.56 g of the compound obtained by (2) above was dissolved into 15 ml of N,N-dimethylformamide, to which 80 mg of hydrogenated sodium (60%) was added. After stirring these under room temperature, 0.18 ml of N,N-dimethylcarbamyl chloride was added to react for 1 hour. The reactive liquid was then added to saturated aqueous solution of sodium bicarbonate, and extraction was performed thrice with 20 ml of methylene chloride. The organic layer was gathered, dried up by magnesium sulfur trioxide and concentrated under reduced pressure. The residue was purified by silica gel column chromatography (eluate solvent; ethylacetate:n-hexane=2:1). Thus 0.58 g of the captioned compound was obtained.

$^1$H—NMR (90 MHz, CDCl$_3$)δ; 2.96(s, 6H), 3.38(s, 3H), 3.40-3.62 (m, 3H), 3.82(s, 3H), 3.85(s, 6H), 4.14-4.35(m, 2H), 4.43(s, 2H), 4.62 (s, 2H), 6.53(s, 2H), 7.04-7.36(m, 2H), 7.62(m, 1H), 8.50(m, 1H).

(4) Synthesis of 1-ethyl-2-(((N-(N,N-dimethyl) carbamyl-N-((2-methoxy-3-(3,4,5-trimethoxy) benzyloxypropyloxy)) carbonyl))) aminomethylpyridinium iodide

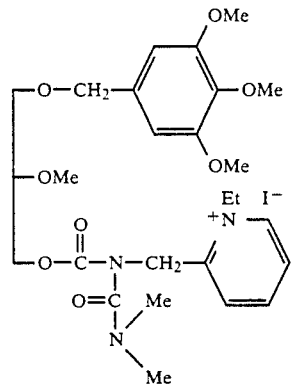

Into 15 ml of ethyl iodide was dissolved the compound obtained by (3) to react for 3 days at 50° C. The reactive liquid was brought to room temperature, ether was added thereto and supernatant was removed by decantation. The sediment was dissolved into acetone, ether was added and the supernatant was removed by decantation. Drying up the sediment to solidify could give the captioned compound in $^1$H—NMR (90 MHz, CDCl$_3$)δ; 1.71(t, J=7 Hz, 3H), 3.04(s, 6H), 3.39 (s, 3H), 3.40-3.66(m, 3H), 3.83(s, 3H), 3.86(s, 6H), 4.24-4.44(m, 2H), 4.46(s, 2H), 5.04(q, J=7 Hz, 2H), 5.25 (s, 2H), 6.56(s, 2H), 7.92-8.54(m, 3H), 9.52(m, 1H).

WORKING EXAMPLE 23

1-(((2-methoxy-3-(3,4,5-trimethoxybenzyloxy)))propyl-3-(1-ethyl-2-pyridinium) methylhydantoin iodide

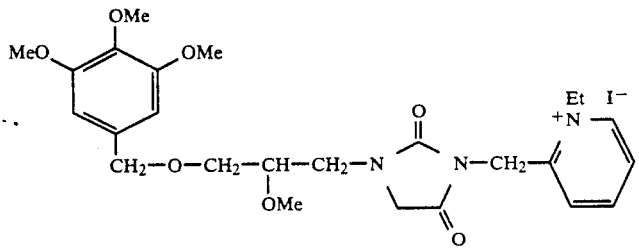

(1) Synthesis of 3-O-methanesulfonyl-2-O-methyl-1-O-(3,4,5-trimethoxy) benzyl glycerin

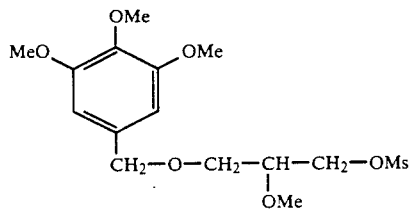

3.0 g of the compound obtained by (1) in the Working Example 7 above and 2.2 g of triethylamine were dissolved into 100 ml of tetrahydrofuran, to which 1.5 g of methanesulfonyl chloride was dropped under incubation on ice. These were stirred under room temperature for 1 hour, poured into icy water and then extraction was conducted thrice with 50 ml of ethylacetate. The liquid thus extracted was washed with saturated saline water. After distilling off the solvent under reduced pressure, the residue was purified by silica gel column chromatography (eluate solvent; ethylacetate:hexane=1:5). 2.8 g of the captioned compound was thus obtained.

$^1$H—NMR (90 MHz, CDCl$_3$)δ; 3.04(s, 3H), 3.48(s, 3H), 3.60(m, 2H), 3.24–3.68(m, 1h), 3.84(s, 3H), 3.88 (s, 6H), 4.28–4.40(m, 2H), 4.49(s, 2H), 6.58(s, 2H).

(2) Synthesis of 3-(2-pyridyl) methylhydantoin

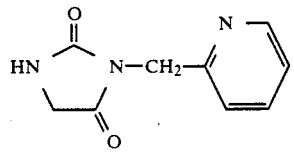

5.0 g of hydantoin, 8.2 g of 2-chloromethylpyridine and 6.9 g of potassium carbonate anhydride were dissolved into 100 ml of N,N-dimethylformamide and these were stirred under room temperature for 1 hour and at 80° C. for 30 minutes. The N,N-dimethylformamide was distilled off under reduced pressure and the residue was purified by silica gel column chromatography (eluate solvent; chloroform:methanol =9:1). Thus 4.8 g of the captioned compound was thus obtained.

$^1$H—NMR (90 MHz, CDCl$_3$)δ; 4.03(s, 2H), 4.81(s, 2H), 6.54(brs, 1H), 7.08–7.36(m, 2H), 7.65(t, J=8 Hz, 1H), 8.54(d, J=8 Hz, 1H).

(3) Synthesis of 1-(((2-methoxy-3-(3,4,5-trimethoxy)benzyloxy))) propyl-3-(2-pyridyl) methylhydantoin

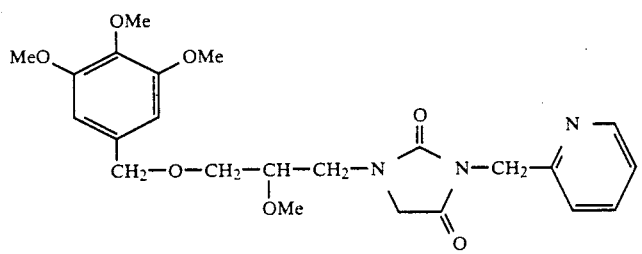

0.9 g of the 3-(2-pyridyl) methylhydantoin was dissolved into 50 ml of N,N-dimethylformamide, to which 0.2 g of hydrogenated sodium (60%) was added under room temperature. To these the compound obtained by (1) was further added and the whole was stirred under room temperature for 30 minutes, then at 80° C. for 1 hour. The reactive liquid was brought to room temperature and poured into icy water. Extraction was then performed thrice with 100 ml of ethylacetate. The liquid thus extracted was washed with saturated saline water. After the solvent was distilled off under reduced pressure the residue was purified by silica gel column chromatography (eluate solvent; ethylacetate:hexane =4:1). Thus 0.66 g of the captioned compound was obtained.

$^1$H—NMR (90 MHz, CDCl$_3$)δ; 3.42(s, 3H), 3.48–3.64(m, 5H), 3.84 (s, 9H), 4.12(s, 2H), 4.45(s, 2H), 4.80 (s, 2H), 6.54(s, 2H), 7.04–7.32(m, 2H), 7.62(t, J=8 Hz, 1H), 8.49(d, J=7 Hz, 1H).

(4) Synthesis of 1-(((2-methoxy-3-(3,4,5-trimethoxy) benzyloxy))) propyl-3-(1-ethyl-2-pyridinium) methylhydantoin iodide

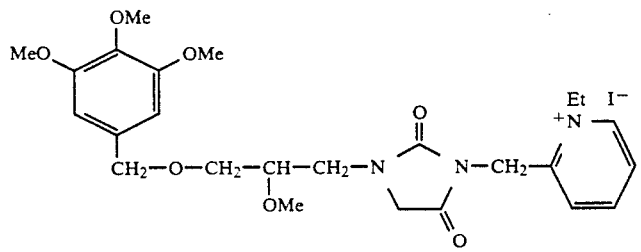

The compound obtained by (3) was dissolved into 10 ml of ethyl iodide to reflux for 24 hours. The insoluble was filtered out, dissolved into acetone and then sedimented by adding ether thereto. Removing the supernatant could give 0.6 g of the captioned compound.

$^1$H—NMR (90 MHz, CDCl$_3$)δ; 1.68(t, J=8 Hz, 3H), 3.44(s, 3H), 3.52–3.68(m, 5H), 3.82(s, 3H), 3.86(s, 6H), 4.26(s, 2H), 4.46(s, 2H), 5.00(q, J=8 Hz, 2H), 5.06(s, 2H), 6.56(s, 2H), 7.98–8.21(m, 2H), 8.47(t, J=8 Hz, 1H), 9.39 (d, J=8 Hz, 1H).

WORKING EXAMPLE 24

1-ethyl-2-(((N-acetyl-N-((2-(2-methoxy-3-(3,4,5-trimethoxybenzyloxy) propyloxy) ethyl))) aminomethylpyridinium iodide

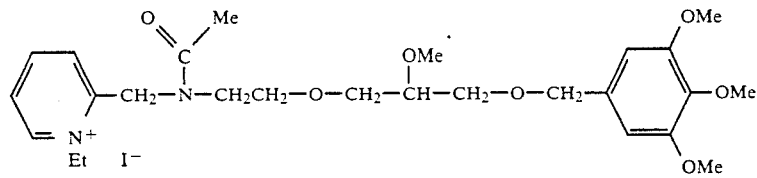

(1) Synthesis of 2-methoxy-3-(3,4,5-trimethoxybenzyloxy) propyloxymethylacetate

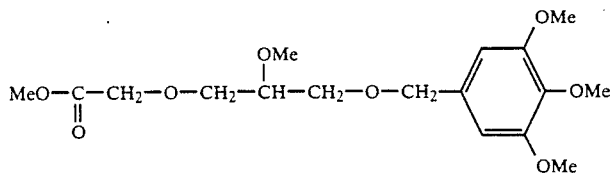

Into 50 ml of N,N-dimethylformamide was dissolved 4.43 g of 2-methoxy-3-(3,4,5-trimethoxybenzyloxy)-1-propanol to which 1.2 g of hydrogenated sodium (60%) was added under room temperature. These were then heated at 60° C. for 1 hour. Under incubation on ice 11.83 g of bromomethyl acetate was dropped thereto and the whole was stirred as such for a while. After distilling off the solvent, icy water was added and extraction was performed with chloroform. They were then washed with saturated saline water and dried up with magnesium sulfur trioxide. After this was filtered out and the solvent distilled off, the residue thereof was purified by silica gel column chromatography (eluate solvent; ethylacetate-hexane=1:3). Thus 1.79 g of the captioned compound was given.

$^1$H—NMR (90 MHz, CDCl$_3$)δ; 3.49(s, 3H), 3.4–3.8(m, 5H), 3.75(s, 3H), 3.85(s, 3H), 3.88(s, 6H), 4.14(s, 2H), 4.49(s, 2), 6.58(s, 2H).

(2) Synthesis of 2-(((2-methoxy-3-(3,4,5-trimethoxybenzyloxy) propyloxy))) ethanol

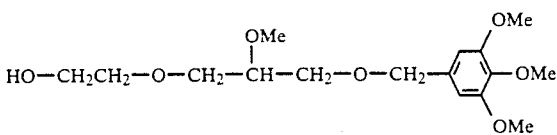

140 mg of hydrogenated lithium aluminum was suspended into 10 ml of tetrahydrofuran, to which was dropped under incubation on ice 1.79 g of ester material obtained by (1). These were brought to room temperature and the hydrogenated lithium aluminum was added until bubbling was ceased. They were thus stirred for 30 minutes. After re-incubation on ice, 0.5 ml of water, 1 ml of aqueous solution of 20% sodium hydroxide and 1 ml of water were dropped thereonto in this order. The insoluble was filtered out and the solvent distilled off. Then the residue was purified by silica gel column chromatography (eluate solvent; ethylacetate:hexane=7:3). Thus 1.01 g of the captioned compound was obtained.

$^1$H—NMR (90 MHz, CDCl$_3$)δ; 2.3(bs, 1H), 3.3–3.8(m, 9H), 3.44(s, 3H), 3.80(s, 3H), 3.83(s, 6H), 4.45(s, 2H), 6.51(s, 2H).

(3) Synthesis of methane sulfonic acid 2-2(((2-methoxy-3-(3,4,5-trimethoxybenzyloxy) propyloxy)))ethyl

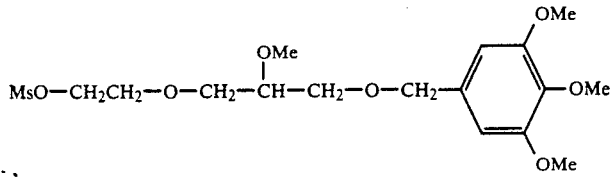

1.0 g of the alcohol material obtained by (2) was dissolved into 20 ml of methylene chloride and 920 mg of triethylamine, onto which 870 mg of methanesulfonyl chloride was dropped at −15° C. After stirring for about 30 minutes, water was added and extraction was conducted with chloroform. The chloroform layer was then washed with 1N-hydrochloric acid, saturated aqueous solution of sodium bicarbonate and with saturated saline water in this order, then dried up with magnesium sulfur trioxide. This was filtered and the solvent distilled off. This could give 1.38 g of the captioned compound.

$^1$H—NMR (90 MHz, CDCl$_3$)δ; 3.02(s, 3H), 3.3–3.95(m, 7H), 3.44 (s, 3H), 3.81(s, 3H), 3.84(s, 6H), 4.15–4.5(m, 2H), 4.45(s, 2H), 6.51(s, 2H).

(4) Synthesis of N-(((2-((2-methoxy-3-(3,4,5-trimethoxybenzyloxy) propyloxy)) ethyl)))-2-pyridylmethylamine

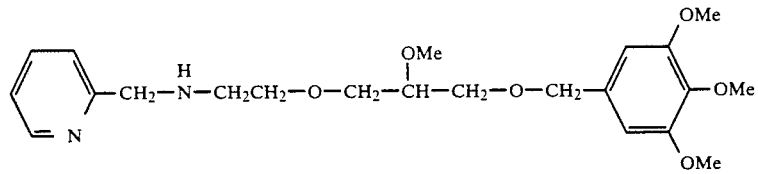

650 mg of aminomethylpyridine was dissolved into 5 ml of N,N-dimethyhormaldehyde, to which wa added 290 mg of hydrogenated sodium (60%) under room temperature. After stirring at 60° C. for 20 minutes, these were incubated on ice. Thereto was added 10ml of the N,N-dimethylformamide solution in the mesyl-ester material as obtained by (3) above. These were then stirred at 80° C. for 2 hours. After distilling off the solvent, water was added, and extraction was performed with chloroform. The chloroform layer was washed with saturated saline water and dried up with magnesium sulfur trioxide. This was filtered, and the solvent was distilled off. Then the residue was purified by silica gel column chromatography (eluate solvent; methanol:chloroform=5:95). Thus 330 mg of the captioned compound was obtained.

$^1$H—NMR (90 MHz, CDCl$_3$)δ; 2.82(t, J=5 Hz, 2H), 3.3–3.8(m, 5H), 3.44(s, 3H), 3.59(t, J=5 Hz, 2H), 3.79 (s, 3H), 3.81(s, 6H), 3.89(s, 2H), 4.44 (s, 2H), 6.51(s, 2H), 6.9–7.35(m, 2H), 7.4–7.7(m, 1H), 8.3–8.55(m, 1H).

(5) Synthesis of N-acetyl-N-(((2-((2-methoxy-3-(3,4,5-trimethoxybenzyloxy) propyloxy)) ethyl)))-2-pyridylmethyamine

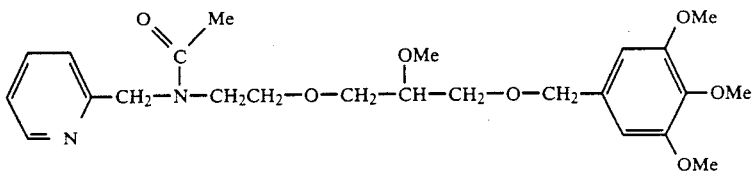

330 g of amine material obtained by (4) was dissolved into 10 ml of pyridine, to which was dropped 400 mg of acetic anhydride under room temperature, and these were stirred as such for 30 minutes. After distilling off the solvent, the residue was treated by silica gel column chromatography (eluate solvent; methanol:chloroform=1:99). Thus 280 g of the captioned compound could be had.

$^1$H—NMR (90 MHz, CDCl$_3$)δ; 2.06 and 2.18(each s, 3H), 3.3–3.75 (m, 9H), 3.40(s, 3H), 3.79(s, 3H), 3.82 (s, 6H), 4.42(s, 2H), 4.67(s, 2H), 6.50 (s, 2H), 6.9–7.35(m, 2H), 7.4–7.7 (m, 1), 8.3–8.6(m, 1H).

(6) 1-ethyl-2-(((N-acetyl-N-((2-(2-methoxy-3-(3,4,5-trimethoxybenzyloxy) propyloxy) ethyl))) aminiomethylpyridinium iodide

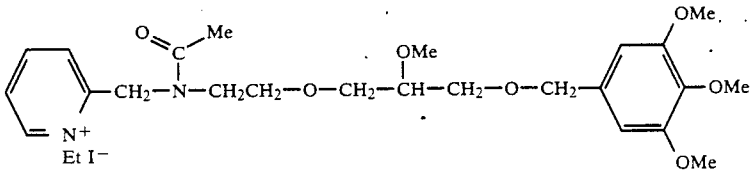

280 g of acetyl material obtained by (5) was dissolved into 10 ml of ethyl iodide and these were stirred at 60° C. under nitrogen current for 87 hours. There existed floating oily matter. The solvent was therefore removed by decantation. Then it was dissolved by adding acetone and ether was added thereto to sediment it again. The solvent was repeatedly removed by decantation and ether was repeatedly added. Thus 230 g of the captioned compound was obtained.

$^1$H—NMR (90 MHz, CDCl$_3$)δ; 1.69(t, J=7 Hz, 3H), 2.24(s, 3H), 3.3–4.0(m, 9H), 3.44(s, 3h), 3.80(s, 3H), 3.82(s, 6H), 4.43(s, 2H), 4.79(q, J=7 Hz, 2H), 5.26(s, 2H), 6.51(s, 2h), 7.5–8.3(m, 3h), 8.70(d, J=5 Hz, 1H).
MS m/a (FAB, Pos.); Null (M+).

EXAMPLE 25

Processes for synthesizing optically active substances of the glycerine derivatives obtained in Example 15 will be described in detail in the present example.

(1) (S)-1-o-benzyl-2,3-o-isopropylidene glycerine

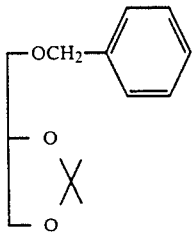

490 g of merketal was dissolved in DMF, followed by addition of 163 g of 60% sodium hydroxide, under cooling with ice, over 15 minutes. After the conclusion of the addition, reaction solution was brought back to room temperature, followed by stirring for 1 hour. Hereafter, 530 ml of benzyl bromide was added dropwise to the reaction solution, followed by stirring for 30 minutes. The reaction solution was then poured into ice water, followed by addition of 3 l of water. The resulting reaction solution was extracted twice with 3 l of ethyl acetate. After washing the extract twice with water, the solvent was distilled off under reduced pressure, and the residue was purified by silica gel column chromatography (eluting solvent; hexane→10% ethyl acetate-hexane →20% ethyl acetate-hexane), thereby obtaining 366 g of the object substance. Incidentally, the optically active merketal used as a starting material in the present synthesizing process can be synthesized in conformity with, for example, the literature D. E. McCjure et al., J. Org. Chem. 43 (25) 4876 (1978).

$^1$H—NMR (90 MHz, CDCl$_3$)δ; 1.34 (S, 3H), 1.40 (S, 3H), 3.32–4.40 (m,5H), 4.73 (S, 2H), 7.28 (S, 5H).

(2) (S)-3-o-bezyl-1-o-triphenylmethyl glycerine

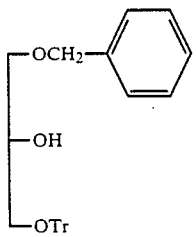

274 g of the compound obtained in (1), 503 g of trimethyl chloride, and 181 g of triethylamine were dissolved in 1.5 l of toluene, followed by refluxing with heating for 1 hour. After cooling, crystals precipitated were filtered off, and washed with successive, 1 l of benzene and 0.5 l of hexane, followed by concentration of mother liquor. The crude product (734 g) was not purified, and used for the subsequent reaction.

$^1$H—NMR (90 MHz, CDCl$_3$)δ; 2.20–2.46 (br, 1H), 3.12–3.26 (m, 2H), 3.40–3.65 (m, 2H), 3.77–4.08 (m, 1H), 4.49 (S, 2H), 7.05–7.60 (m, 20H).

(3) (R)-1-o-benzyl glycerine

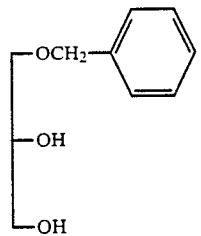

366 g of the compound obtained in (2) was dissolved in 3 l of tetrahydrofuran, followed by addition of 500 ml of 3 N—HCl and stirring for 3 hours at room temperature. Then, reaction solution was adjusted to pH 7–8 by addition of sodium hydrogencarbonate, followed by separation of an organic layer. After addition of anhydrous magnesium sulfate, the organic layer was filtered by the use of silica gel. The solvent was distilled off under reduced pressure to obtain 274 g of the object substance.

$^1$H—NMR (90 MHz, CDCl$_3$)δ; 3.32–3.64 (m, 4h), 3.66–3.93 (m, 1H), 4.10 (S, 2H), 4.47 (S, 2H), 7.30 (S, 5H).

(4) (S)-3-o-benzyl-2-o-methyl-3-o-triphenylmethyl glycerine

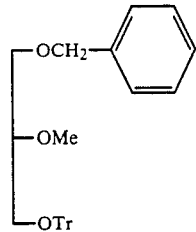

734 g of the product obtained in (2) was dissolved in 1 l of tetrahydrofuran, followed by addition of 429 g of methyl iodide. Under cooling with ice, 72 g of 60% sodium hydride was added. After stirring for 30 minutes at room temperature, 0.5 l of DMF was added dropwise. After stirring for 30 minutes, 3 l of ice water was added, followed by extraction with 4 l of ethyl acetate. After washing with water and saline solution, concentration was performed, thereby obtaining 750 g of the object substance as a crude product.

$^1$H—NMR (90 MHz, CDCl$_3$)δ; 3.10–3.30 (m, 2H), 3.37 (S, 3H), 3.37–3.57 (m, 3H), 4.50 (S, 2H), 6.93–7.53 (m, 20H).

(5) (R)-1-o-benzyl-2-o-methyl glycerine

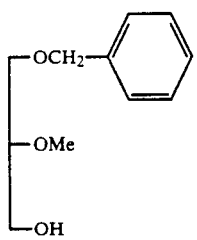

750 g of the product obtained in (4), and 97 g of p-toluenesulfonic acid were dissolved in 750 ml of methanol and 750 ml of tetrahydrofuran, followed by refluxing with heating for 4 hours. After cooling, 1 l of 5% sodium hydrogencarbonate was added, followed by extraction with 1 l of ethyl acetate for three times. After washing and concentration, 4 l of isopropyl ether was added, the solid matter formed was filtered off, and mother liquor was concentrated. The solid matter newly formed was filtered off, followed by washing with isopropyl ether. The resulting mother liquor and washing were concentrated. The residue was purified by column chromatography (eluting solvent; hexane-ethyl acetate), thereby obtaining 170 g of the object substance.

$^1$H—NMR (90 MHz, CDCl$_3$)$\delta$; 1.26 (br, 1H), 3.40 (S, 3H), 3.40–3.80 (m, 5H), 4.50 (S, 2H), 7.26 (S, 5H).

(6) (S)-3-o-benzyl-1-o-(4-hydroxy)piperidinocarbonyl-2-o-methyl glycerine

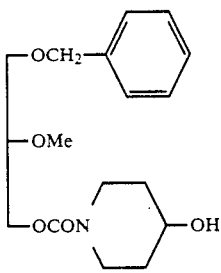

85 g of the compound obtained in (5) was dissolved in 350 ml of pyridine, followed by dropping of 81.5 g of phenyl chlorocarbonate under cooling with ice. After stirring for 30 minutes at room temperature, 200 ml of aqueous saturated sodium hydrogencarbonate solution was added, followed by extraction with 0.5 l of ethyl acetate. After washing with successive, water, 1 N—HCl, water, and aqueous saturated sodium hydrogencarbonate solution, the solvent was distilled off under reduced pressure. Then, 88 g of 4-hydroxypiperidine was added to the residue, followed by stirring for 30 minutes at 100° C. After cooling, reaction mixture was purified by column chromatography (eluting solvent; hexane-ethyl acetate), thereby obtaining 136 g of the object substance.

$^1$H—NMR (90 MHz, CDCl$_3$)$\delta$; 1.12–2.04 (m, 5H), 2.92–3.24 (m, 2H), 3.46 (S, 3H), 3.48–3.62 (m, 2H), 3.64–4.00 (m, 4H), 4.14–4.28 (m, 2H), 4.56 (S, 2H), 7.34 (S, 5H).

(7) (S)-3-o-benzyl-1-o-(4-octadecylcarbamoyloxy)piperidinocarbonyl-2-o-methyl glycerine

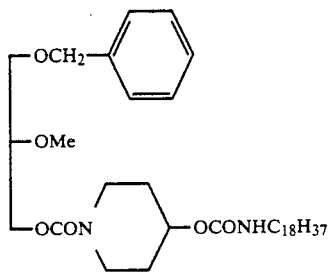

135 g of the compound obtained in (6), and 309 g of octadecyl isocyanate were dissolved in 300 ml of xylene and 100 ml of pyridine, followed by stirring with heating for 9 hours at 120° C. After the solvent was distilled off, reaction mixture was purified by silica gel column chromatography (eluting solvent; benzene-ethyl acetate), thereby obtaining 190 g of the object substance.

$^1$H—NMR (90 MHz, CDCl$_3$)$\delta$; 0.72–0.96 (m, 3H), 1.03–1.90 (m, 36H), 2.96–3.28 (m, 4H), 3.44 S, 3H), 3.45–3.72 (m, 3H), 4.12–4.28 (m, 3H), 4.52 (S, 2H), 4.64–4.82 (m ,2H), 7.28 (S, 5H).

(8) (S)-1-o-(4-octadecylcarbamoyloxy)piperidinocarbonyl-2-o-methyl glycerine

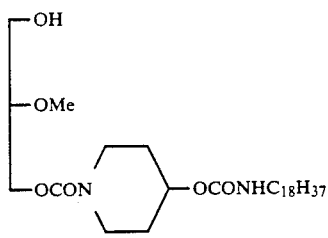

187 g of the compound obtained in (7) was dissolved in 500 ml of methanol and 500 ml of tetrahydrofuran. After addition of 25 g of 5% Pd-C, deprotection was performed in a stream of hydrogen at ordinary temperature and atmospheric pressure. The catalyst was filtered off, followed by distilling off the solvent, thereby obtaining 152 g of the object substance.

$^1$H—NMR (90 MHz, CDCl$_3$)$\delta$; 1.74–2.06 (m, 3H), 1.08–2.04 (m, 36H), 2.50 t, J=7.0 Hz, 1H), 2.94–3.78 (m, 9H), 3.68 (S, 3H), 4.24 (d, J=5.4 Hz, 2H), 4.56–5.00 (m, 2H).

(9) (S)-2-o-methyl-1-o-(4-octadecylcarbamoyloxy)piperidinocarbonyl-3-o-[N-(2-pyridyl)methyl] carbamoyl glycerine

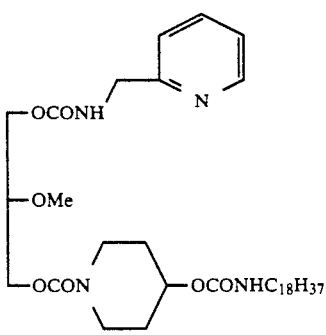

154 g of the compound obtained in (8) was dissolved in 500 ml of pyridine, followed by dropping of 68 g of phenyl chlorocarbonate under cooling with ice. After stirring for 2 hours at room temperature, 500 ml of aqueous saturated sodium hydrogencarbonate solution was added, followed by extraction with ethyl acetate. The resulting extract was washed with successive, 2 N—HCl, water, aqueous saturated sodium hydrogencarbonate solution, and saline solution, and concentrated. Then, 63 g of 2-aminomethylpyridine was added to the concentrate, followed by stirring with heating for 1 hour at 100° C. After cooling, reaction mixture was purified by silica gel column chromatography (eluting solvent; hexane-ethyl acetate). The compound thus obtained was crystallized from a mixed solvent of 0.5 l of benzene and 1.0 l of hexane to obtain 172 g of the object substance.

$^1$H—NMR (90 MHz, CDCl$_3$)δ; 0.72–1.00 (m, 3H), 1.04–2.08 (m, 36H), 3.00–3.94 (m, 7H), 3.44 (S, 3H), 4.03–4.40 (m, 4H), 4.50 (d, J=7.0 Hz, 2H), 4.87 (m, 2H), 6.10 (m, 1H), 7.10–7.40 (m, 2H), 7.70 (m, 1H), 8.55 (m, 1H).

(10) (R)-1-o-[N-(2-methoxy)benzoyl-N-(2-pyridyl)methyl]carbamoyl-2-o-methyl-3-o-(4-octadecylcarbamoyloxy)piperidinocarbonyl glycerine

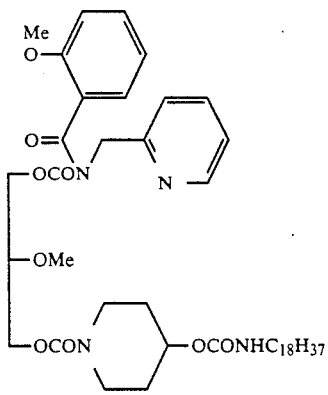

171 g of the compound obtained in (9) was dissolved in 500 ml of pyridine, followed by dropping of 66 g of o-anisoyl chloride at room temperature. After stirring for 2 hours, 50 ml of methanol was added. Then, 500 ml of aqueous saturated sodium hydrogencarbonate was added, followed by extraction with ethyl acetate. The resulting extract was washed with water and saline solution, followed by concentration under reduced pressure. The residue was purified by silica gel column chromatography (eluting solvent; hexane-ethyl acetate) to obtain 203 g of the object substance.

$^1$H—NMR (90 MHz, CDCl$_3$)δ; 0.73–1.02 (m, 3H), 1.09–1.45 (m, 32H), 1.50–1.90 (m, 4h), 3.02–3.39 (m, 5H), 3.21 (S, 3H), 3.52–3.80 (m, 5H), 3.85 (S, 3H), 4.00–4.13 (m, 2H), 4.53–4.93 (m, 1H), 5.25 (S, 2H), 6.84–7.80 (m, 7H), 8.58 (m, 1H).

(11) 1-Ethyl-2-[N-(2-methoxy)benzoyl-N-{(R)-2-methoxy-3-(4-octadecylcarbamoyloxy)piperidinocarbonyloxy-propyloxy}carbonyl]aminomethylpyridinium chloride

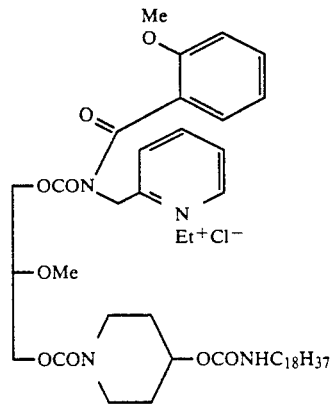

100 g of the compound obtained in (10) was dissolved in 1 kg of ethyl iodide, followed by refluxing with heating in a stream of nitrogen while shading for 2 days. After ethyl iodide was distilled off, reaction mixture was treated by the use of ion exchange resin IRA-410 (Cl$^-$ type, eluting solvent; methanol:water=7:3), followed by concentration. The residue thus obtained was purified by silica gel column chromatography (eluting solvent; dichloromethane-methanol) to obtain 57 g of the object substance.

$^1$H—NMR (90 MHz, CDCl$_3$)δ; 0.87 t, 3H), 1.18–1.35 (m, 32H), 1.42–2.25 (m, 5H), 1.80 (t,3H), 3.15 (m, 2H), 3.23(S, 3H), 3.23–3.35 (m, 3H), 3.65 (m, 2H), 3.78 (m, 1), 3.85 (m, 1H), 3.90 (S, 3H), 4.05 (m, 1H), 4.15 (m, 1H), 4.82 (m, 1H), 5.25 (q, 2H), 5.52 (br, 2H), 6.94 (d, J=9 Hz, 1H), 7.07 (dd, J=8 Hz, 7 Hz, 1H), 7.49 (m ,2H), 8.05 (m, 2H), 8.36 (m, 1H), 10.34 (m, 1H).

FAB 825 (M+).

$[\alpha]_{405\ nm}^{20°\ C.}$ −3.30 (C=10, CHCl$_3$).

We claim:

1. A glycerin derivative having the following formula (I) or a pharmacologically acceptable salt thereof:

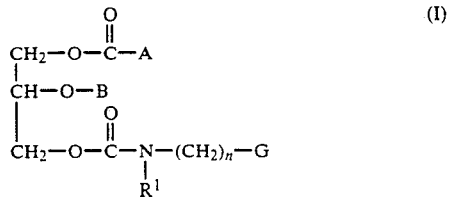

wherein in formula (I): A represents:
(1) a nitrogen or nitrogen and oxygen containing ring selected from the group consisting of

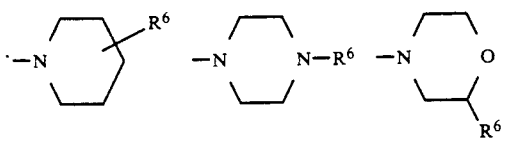

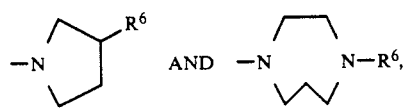

$R^6$ represents a hydrogen atom or a hydroxyl group, an alkyl group, an alkoxy group, an aryl group, a group of the formula: —$COR^7$ wherein $R^7$ is an alkyl group, an alkoxy group or a group of the formula:

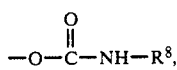

and wherein $R^8$ is a hydrogen atom or an alkyl group;

(2) a group of the formula:

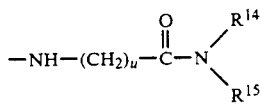

in which u represents an integer of 0 to 6 and $R^{14}$ and $R^{15}$ combine to form a ring which may contain an oxygen atom, (3) a group of the formula:

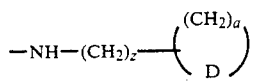

in which z represents an integer of 0 to 6, a represents an integer of 3 or 4 and D represents and oxygen atom, a sulfur atom or a nitrogen atom, B represents a lower alkyl or an arylalkyl group, $R^1$ represents an acyl group derived from a carboxylic acid, n represents an integer of 0 to 3, and G represents a group of the formula:

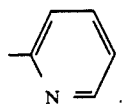

2. The glycerin derivative or a pharmacologically acceptable salt thereof as claimed in claim 1, in which the glycerin derivative has the formula (I), A is (1), B is a lower alkyl, R1 is an acyl group, n is 1 and G is 2-pyridyl.

3. The glycerin derivative or a pharmacologically acceptable salt thereof as claimed in any of claims 1 or 2, in which the formula is (I), G is a pyridinium salt in which the nitrogen of the pyridyl for G in the formula (I) is quaternized.

4. The glycerin derivative or a pharmacologically acceptable salt thereof as claimed in claim 1, wherein and G is a pyridinium salt having the formula:

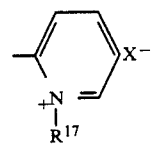

in which R17 is a lower alkyl and X is a pharmacologically acceptable anion.

5. The glycerin derivative or a pharmacologically acceptable salt thereof as claimed in claim 1, wherein X is a halogen.

6. The glycerin derivative or a pharmacologically acceptable salt thereof as claimed in claim 1, wherein A is (1), R6 is —OCO—NHR8, R8 is hydrogen or an alkyl, B is a lower alkyl, R1 is an acyl group and n is 1.

7. The glycerin derivative or a pharmacologically acceptable salt thereof as claimed in claim 1, wherein A is (1) and a is pyperidiene, R6 is —OCO—NHR8, R8 is hydrogen or an alkyl, B is methyl, R1 is an acyl group and n is 1.

8. The glycerin derivative or a pharmacologically acceptable salt thereof as claimed in claim 7, in which R8 is an alkyl having 14 to 22 carbon atoms.

9. The glycerin derivative or a pharmacologically acceptable salt thereof as claimed in claim 7, in which R8 is an alkyl having 16 to 20 carbon atoms.

10. The glycerin derivative or a pharmacologically acceptable salt thereof as claimed in claim 7, in which R8 is an alkyl having 18 carbon atom.

11. The glycerin derivative or a pharmacologically acceptable salt thereof as claimed in claim 7, in which R1 is acetyl.

12. The glycerin derivative or a pharmacologically acceptable salt thereof as claimed in claim 7, in which R1 is acetyl.

13. The glycerin derivative or a pharmacologically acceptable salt thereof as claimed in claim 7, in which R1 is benzoyl or a substituted benzoyl.

14. The glycerin derivative or a pharmacologically acceptable salt thereof as claimed in claim 7, in which R1 is o-, m- or p-alkoxybenzoyl.

15. The glycerin derivative or a pharmacologically acceptable salt thereof as claimed in claim 7, in which R1 is o-, m- or p-methoxybenzoyl.

16. The glycerin derivative or a pharmacologically acceptable salt thereof as claimed in claim 7, in which R1 is o-methoxybenzoyl.

17. The glycerin derivative or a pharmacologically acceptable salt thereof as claimed in claim 7, in which R1 is o-methoxybenzoyl and R8 is an alkyl having 16 to 20 carbon atoms.

18. The glycerin derivative or a pharmacologically acceptable salt thereof as claimed in claim 4, wherein R17 is ethyl and X is chlorine.

19. The compound according to claim 1 which is:

20. The compound according to claim 1 which is

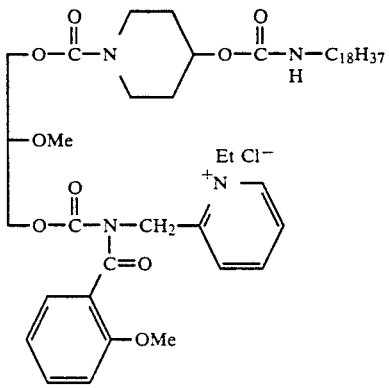

21. The compound according to claim 1 which is

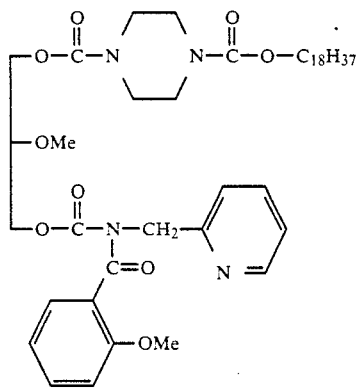

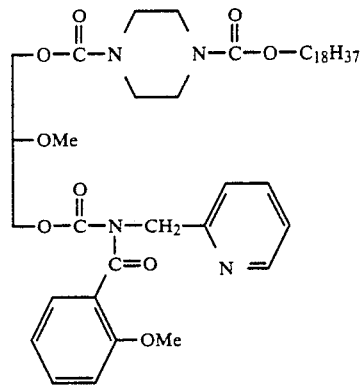

22. The compound according to claim 1 wherein said acyl group derived from a carboxylic acid is selected from an aliphatic saturated carboxylic acid, an aliphatic unsaturated carboxylic acid, a carbocyclic carboxylic acid, or a heterocarboxylic acid.

23. The compound according to claim 1 wherein in A(2) $R^{14}$ and $R^{15}$ form

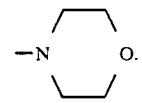

24. A pharmaceutical composition which comprises a therapeutically effective amount of the glycerin derivative or a pharmacologically acceptable salt thereof as defined in claim 1 and a pharmacologically acceptable carrier.

25. A method for treating a disease caused by platelet activating factors (PAF), which comprises administering a therapeutically effective amount of the glycerin derivative or a pharmacologically acceptable salt thereof as defined in claim 1 to a human being suffering from said disease.

26. The method as claimed in claim 25, in which the disease is one against which a PAF receptor antagonist is effective.

27. The method as claimed in claim 25, wherein said disease is DIC.

28. The method as claimed in claim 25, in which the disease is a shock.

29. The method as claimed in claim 28, in which the shock is anaphylactic shock or hemoribatic shock.

30. The method as claimed in claim 25, in which the disease is allergic diseases.

* * * * *